US011207393B2

(12) United States Patent
Sharpe et al.

(10) Patent No.: US 11,207,393 B2
(45) Date of Patent: Dec. 28, 2021

(54) REGULATORY T CELL PD-1 MODULATION FOR REGULATING T CELL EFFECTOR IMMUNE RESPONSES

(71) Applicants: President and Fellows of Harvard College, Cambridge, MA (US); The Brigham and Women's Hospital, Inc., Boston, MA (US); Dana-Farber Cancer Institute, Inc., Boston, MA (US)

(72) Inventors: Arlene H. Sharpe, Brookline, MA (US); Gordon J. Freeman, Brookline, MA (US); Loise M. Francisco, Belmont, MA (US); Peter T. Sage, Brookline, MA (US); Sun J. Lee, Statesboro, GA (US); Scott B. Lovitch, Somerville, MA (US); Vikram R. Juneja, Boston, MA (US); Catherine L. Tan, Boston, MA (US)

(73) Assignees: President and Fellows of Harvard College, Cambridge, MA (US); The Brigham and Women's Hospital, Inc., Boston, MA (US); Dana-Farber Cancer Institute, Inc., Boston, MA (US)

( * ) Notice: Subject to any disclaimer, the term of this patent is extended or adjusted under 35 U.S.C. 154(b) by 514 days.

(21) Appl. No.: 15/768,077

(22) PCT Filed: Oct. 14, 2016

(86) PCT No.: PCT/US2016/057031
§ 371 (c)(1),
(2) Date: Apr. 13, 2018

(87) PCT Pub. No.: WO2017/066561
PCT Pub. Date: Apr. 20, 2017

(65) Prior Publication Data
US 2018/0303922 A1 Oct. 25, 2018

Related U.S. Application Data

(60) Provisional application No. 62/242,509, filed on Oct. 16, 2015.

(51) Int. Cl.
| C07K 14/705 | (2006.01) |
| A61K 35/17 | (2015.01) |
| A61K 39/395 | (2006.01) |
| A61P 37/02 | (2006.01) |
| A61K 38/17 | (2006.01) |
| A61K 39/00 | (2006.01) |
| C07K 14/00 | (2006.01) |
| A61P 35/00 | (2006.01) |
| A61K 9/00 | (2006.01) |
| A61K 39/008 | (2006.01) |
| A61K 45/06 | (2006.01) |

(52) U.S. Cl.
CPC .... *A61K 39/001129* (2018.08); *A61K 9/0019* (2013.01); *A61K 35/17* (2013.01); *A61K 38/1774* (2013.01); *A61K 39/008* (2013.01); *A61K 39/39541* (2013.01); *A61P 35/00* (2018.01); *A61P 37/02* (2018.01); *C07K 14/00* (2013.01); *C07K 14/70503* (2013.01); *A01K 2227/105* (2013.01); *A01K 2267/0325* (2013.01); *A01K 2267/0331* (2013.01); *A61K 45/06* (2013.01); *A61K 2039/5158* (2013.01); *A61K 2300/00* (2013.01)

(58) Field of Classification Search
None
See application file for complete search history.

(56) References Cited

U.S. PATENT DOCUMENTS

| 9,644,179 B2* | 5/2017 | Riley | C12N 5/0637 |
| 9,701,749 B2* | 7/2017 | Shibayama | A61K 39/395 |
| 9,895,440 B2* | 2/2018 | Weiner | A61K 31/135 |
| 10,493,148 B2* | 12/2019 | Yachi | C07K 2317/565 |
| 2007/0166307 A1* | 7/2007 | Bushell | C07K 16/2812 424/144.1 |
| 2009/0217401 A1* | 8/2009 | Korman | C07K 16/2818 800/18 |
| 2009/0257988 A1* | 10/2009 | Horwitz | C12N 5/0636 424/93.7 |
| 2010/0135974 A1* | 6/2010 | Eshhar | C12N 5/0636 424/93.71 |
| 2010/0196406 A1* | 8/2010 | Karin | A61P 25/00 424/184.1 |
| 2012/0076805 A1* | 3/2012 | Sharpe | A61K 35/17 424/184.1 |
| 2013/0156774 A1* | 6/2013 | Kuchroo | A61P 35/00 424/136.1 |
| 2014/0377240 A1* | 12/2014 | Sitkovsky | C12N 5/0637 424/93.71 |
| 2016/0272708 A1* | 9/2016 | Chen | A61P 13/12 |
| 2019/0256599 A1* | 8/2019 | Bhattacharya | A61P 35/00 |

FOREIGN PATENT DOCUMENTS

WO WO-2006/121168 A1 11/2006

OTHER PUBLICATIONS

Woods et al. (2016) Cancer Immunol Res; 4(11 Suppl): Abstract A067 (5 pages).*
Lowther et al. (2016) JCI Insight. 1(5): e85935, p. 1-15.*
Baksh et al. (2015) Semin Oncol 42: 363-377.*
Chinai et al. (2015) Trends in Pharmacological Sciences 36: 587-595.*
Okazaki et al. (2006) Trends in Immunology 27: 195-201.*

(Continued)

*Primary Examiner* — Ilia I Ouspenski
(74) *Attorney, Agent, or Firm* — Foley Hoag LLP

(57) ABSTRACT

The present invention is based, in part, on the identification of methods of modulating PD-1 expression and/or activity in regulatory T cells (Tregs) to thereby regulate effector immune responses in effector T cells (Teffs).

7 Claims, 22 Drawing Sheets
Specification includes a Sequence Listing.

(56) References Cited

OTHER PUBLICATIONS

Francisco et al., "PD-L1 regulates the development, maintenance, and function of induced regulatory T cells," J Exp Med, 206(13): 3015-3019 (2009).
International Search Report and Written Opinion for International Application No. PCT/US2016/057031 dated Apr. 18, 2017.
Iwamura et al., "siRNA-mediated silencing of PD-1 ligands enhances tumor-specific human T-cell effector functions," Gene Ther, 19(10): 959-966 (2012).
Sage et al., "The receptor PD-1 controls follicular regulatory T cells in the lymph nodes and blood," Nat Immunol, 14(2): 152-161 (2013).
Wong et al., "Blockade of programmed death-1 in young (New Zealand Black x New Zealand White)F1 mice promotes the suppressive capacity of CD4+ regulatory T cells protecting from lupus-like disease," J Immunol, 190(11): 5402-5410 (2013).
Li et al., "A naturally occurring CD8+CD122+T-cell subset as a memory-like Treg family," Cell Mol Immunol, 11(4): 326-331 (2014).
Safinia et al., "Regulatory T cells: serious contenders in the promise for immunological tolerance in transplantation," Front Immunol 6: 438 (16 pages) (2015).
Simeone et al., "Anti-PD1 and anti-PD-L1 in the treatment of metastatic melanoma," Melanoma Management, 2(1): 41-50 (2015).
Singer et al., "Regulatory T Cells as Immunotherapy," Front Immunol, 5:46 (10 pages) (2014).

* cited by examiner

D

E CNS

F cLN

SEQUENCE LISTING

```
<160> NUMBER OF SEQ ID NOS: 20

<210> SEQ ID NO 1
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 1
cactctggtg gggctgctcc aggc atg cag atc cca cag gcg ccc tgg cca        51
                         Met Gln Ile Pro Gln Ala Pro Trp Pro
                           1               5 gtc gtc tgg gcg gtg cta caa ctg ggc tgg cgg cca gga tgg ttc tta       99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg      147
Asp Ser Pro Asp Arg Pro Trp Asn Pro Pro Thr Phe Ser Pro Ala Leu
             30                  35                  40 ctc gtg gtg acc gaa ggg gac aac gcc acc ttc acc tgc agc ttc tcc      195
Leu Val Val Thr Glu Gly Asp Asn Ala Thr Phe Thr Cys Ser Phe Ser
         45                  50                  55 aac aca tcg gag agc ttc gtg cta aac tgg tac cgc atg agc ccc agc      243
Asn Thr Ser Glu Ser Phe Val Leu Asn Trp Tyr Arg Met Ser Pro Ser
     60                  65                  70 aac cag acg gac aag ctg gcc gcc ttc ccc gag gac cgc agc cag ccc      291
Asn Gln Thr Asp Lys Leu Ala Ala Phe Pro Glu Asp Arg Ser Gln Pro
 75                  80                  85 ggc cag gac tgc cgc ttc cgt gtc aca caa ctg ccc aac ggg cgt gac      339
Gly Gln Asp Cys Arg Phe Arg Val Thr Gln Leu Pro Asn Gly Arg Asp
             90                  95                 100                 105 ttc cac atg agc gtg gtc agg gcc cgg cgc aat gac agc ggc acc tac      387
```

```
Phe His Met Ser Val Val Arg Ala Arg Arg Asn Asp Ser Gly Thr Tyr
            110                 115                 120 ctc tgt ggg gcc atc tcc ctg gcc ccc aag gcg cag atc aaa gag agc       435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca       483
Leu Arg Ala Glu Leu Arg Val Thr Glu Arg Arg Ala Glu Val Pro Thr
            140                 145                 150 gcc cac ccc agc ccc tca ccc agg tca gcc ggc cag ttc caa acc ctg       531
Ala His Pro Ser Pro Ser Pro Arg Ser Ala Gly Gln Phe Gln Thr Leu
            155                 160                 165 gtg gtt ggt gtc gtg ggc ggc ctg ctg ggc agc ctg gtg ctg cta gtc       579
Val Val Gly Val Val Gly Gly Leu Leu Gly Ser Leu Val Leu Leu Val
170             175                 180                 185 tgg gtc ctg gcc gtc atc tgc tcc cgg gcc gca cga ggg aca ata gga       627
Trp Val Leu Ala Val Ile Cys Ser Arg Ala Ala Arg Gly Thr Ile Gly
                190                 195                 200 gcc agg cgc acc ggc cag ccc ctg aag gag gac ccc tca gcc gtg cct       675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag       723
Val Phe Ser Val Asp Tyr Gly Glu Leu Asp Phe Gln Trp Arg Glu Lys
            220                 225                 230 acc ccg gag ccc ccc gtg ccc tgt gtc cct gag cag acg gag tat gcc       771
Thr Pro Glu Pro Pro Val Pro Cys Val Pro Glu Gln Thr Glu Tyr Ala
235             240                 245 acc att gtc ttt cct agc gga atg ggc acc tca tcc ccc gcc cgc agg       819
Thr Ile Val Phe Pro Ser Gly Met Gly Thr Ser Ser Pro Ala Arg Arg
250             255                 260                 265 ggc tca gct gac ggc cct cgg agt gcc cag cca ctg agg cct gag gat       867
Gly Ser Ala Asp Gly Pro Arg Ser Ala Gln Pro Leu Arg Pro Glu Asp
                270                 275                 280 gga cac tgc tct tgg ccc ctc tgaccggctt ccttggccac cagtgttctg cag      921
Gly His Cys Ser Trp Pro Leu
                285

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125
```

```
Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 3
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 3
gcttcccgag gctccgcacc agccgcgctt ctgtccgcct gcagggcatt ccagaaag        58 atg agg ata ttt gct gtc ttt ata ttc atg acc tac tgg cat ttg ctg      106
Met Arg Ile Phe Ala Val Phe Ile Phe Met Thr Tyr Trp His Leu Leu
1               5                   10                  15 aac gca ttt act gtc acg gtt ccc aag gac cta tat gtg gta gag tat      154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta      202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att      250
Asp Leu Ala Ala Leu Ile Val Tyr Trp Glu Met Glu Asp Lys Asn Ile
    50                  55                  60 att caa ttt gtg cat gga gag gaa gac ctg aag gtt cag cat agt agc      298
Ile Gln Phe Val His Gly Glu Glu Asp Leu Lys Val Gln His Ser Ser
65                  70                  75                  80 tac aga cag agg gcc cgg ctg ttg aag gac cag ctc tcc ctg gga aat      346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac      394
Ala Ala Leu Gln Ile Thr Asp Val Lys Leu Gln Asp Ala Gly Val Tyr
                100                 105                 110 cgc tgc atg atc agc tat ggt ggt gcc gac tac aag cga att act gtg      442
Arg Cys Met Ile Ser Tyr Gly Gly Ala Asp Tyr Lys Arg Ile Thr Val
            115                 120                 125 aaa gtc aat gcc cca tac aac aaa atc aac caa aga att ttg gtt gtg      490
Lys Val Asn Ala Pro Tyr Asn Lys Ile Asn Gln Arg Ile Leu Val Val
    130                 135                 140
```

```
gat cca gtc acc tct gaa cat gaa ctg aca tgt cag gct gag ggc tac      538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt      586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat      634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac      682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg      730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca      778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt      833
Leu Ser Pro Ser Thr
                245 gaataaatga atgaatgaat aacactatgt ttacaaaata tatcctaatt cctcacctcc      893 attcatccaa accatattgt tacttaataa acattcagca gatatttatg gaataaaaaa      953 aaaaaaaaaa aaaaa                                                        968

<210> SEQ ID NO 4
<211> LENGTH: 245
<212> TYPE: PRT
<213> ORGANISM: Homo sapiens

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
```

```
              195                 200                 205
Cys Thr Phe Arg Arg Leu Asp Pro Glu Glu Asn His Thr Ala Glu Leu
        210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 5
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 5
cgaggctccg caccagccgc gcttctgtcc gcctgcaggg cattccagaa ag atg agg      58
                                                         Met Arg
                                                         1 ata ttt gct gtc ttt ata ttc atg acc tac tgg cat ttg ctg aac gca      106
Ile Phe Ala Val Phe Ile Phe Met Thr Tyr Trp His Leu Leu Asn Ala
        5                  10                  15 ttt act gtc acg gtt ccc aag gac cta tat gtg gta gag tat ggt agc      154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg      202
Asn Met Thr Ile Glu Cys Lys Phe Pro Val Glu Lys Gln Leu Asp Leu
35                  40                  45                  50 gct gca cta att gtc tat tgg gaa atg gag gat aag aac att att caa      250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga      298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca      346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc      394
Leu Gln Ile Thr Asp Val Lys Leu Gln Asp Ala Gly Val Tyr Arg Cys
     100                 105                 110 atg atc agc tat ggt ggt gcc gac tac aag cga att act gtg aaa gtc      442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca      490
Asn Ala Pro Tyr Asn Lys Ile Asn Gln Arg Ile Leu Val Val Asp Pro
                 135                 140                 145 gtc acc tct gaa cat gaa ctg aca tgt cag gct gag ggc tac ccc aag      538
Val Thr Ser Glu His Glu Leu Thr Cys Gln Ala Glu Gly Tyr Pro Lys
             150                 155                 160 gcc gaa gtc atc tgg aca agc agt gac cat caa gtc ctg agt ggt aag      586
Ala Glu Val Ile Trp Thr Ser Ser Asp His Gln Val Leu Ser Gly Lys
         165                 170                 175 acc acc acc acc aat tcc aag aga gag gag aag ctt ttc aat gtg acc      634
Thr Thr Thr Thr Asn Ser Lys Arg Glu Glu Lys Leu Phe Asn Val Thr
     180                 185                 190 agc aca ctg aga atc aac aca aca act aat gag att ttc tac tgc act      682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc      730
```

```
Phe Arg Arg Leu Asp Pro Glu Glu Asn His Thr Ala Glu Leu Val Ile
            215                 220                 225 cca gaa cta cct ctg gca cat cct cca aat gaa agg act cac ttg gta      778
Pro Glu Leu Pro Leu Ala His Pro Pro Asn Glu Arg Thr His Leu Val
            230                 235                 240 att ctg gga gcc atc tta tta tgc ctt ggt gta gca ctg aca ttc atc      826
Ile Leu Gly Ala Ile Leu Leu Cys Leu Gly Val Ala Leu Thr Phe Ile
            245                 250                 255 ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
            260                 265                 270 caa gat aca aac tca aag aag caa agt gat aca cat ttg gag gag acg      922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttagggggt    982
tcatcgggc tgagcgtgac aagaggaagg aatgggcccg tgggatgcag gcaatgtggg     1042
acttaaaagg cccaagcact gaaaatggaa cctggcgaaa gcagaggagg agaatgaaga    1102
aagatggagt caaacaggga gcctggaggg agaccttgat actttcaaat gcctgagggg   1162
ctcatcgacg cctgtgacag ggagaaagga tacttctgaa caaggagcct ccaagcaaat   1222
catccattgc tcatcctagg aagacgggtt gagaatccct aatttgaggg tcagttcctg   1282
cagaagtgcc ctttgcctcc actcaatgcc tcaatttgtt ttctgcatga ctgagagtct   1342
cagtgttgga acgggacagt atttatgtat gagttttttcc tatttatttt gagtctgtga  1402
ggtcttcttg tcatgtgagt gtggttgtga atgatttctt ttgaagatat attgtagtag   1462
atgttacaat tttgtcgcca aactaaactt gctgcttaat gatttgctca catctagtaa   1522
aacatggagt atttgtaaaa aaaaaaaaaa a                                  1553
```

<210> SEQ ID NO 6
<211> LENGTH: 290
<212> TYPE: PRT
<213> ORGANISM: Homo sapiens

<400> SEQUENCE: 6

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160
```

```
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
        180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
    290
```

<210> SEQ ID NO 7
<211> LENGTH: 873
<212> TYPE: DNA
<213> ORGANISM: Mus musculus

<400> SEQUENCE: 7

```
atgaggatat tgctggcat tatattcaca gcctgctgtc acttgctacg ggcgtttact      60
atcacggctc caaaggactt gtacgtggtg gagtatggca gcaacgtcac gatggagtgc    120
agattccctg tagaacggga gctggacctg cttgcgttag tggtgtactg ggaaaaggaa    180
gatgagcaag tgattcagtt tgtggcagga gaggaggacc ttaagcctca gcacagcaac    240
ttcagggga gagcctcgct gccaaaggac cagcttttga agggaaatgc tgcccttcag    300
atcacagacg tcaagctgca ggacgcaggc gtttactgct gcataatcag ctacggtggt    360
gcggactaca gcgaatcac gctgaaagtc aatgccccat accgcaaaat caaccagaga    420
atttccgtgg atccagccac ttctgagcat gaactaatat gtcaggccga gggttatcca    480
gaagctgagg taatctggac aaacagtgac caccaacccg tgagtgggaa gagaagtgtc    540
accacttccc ggacagaggg gatgcttctc aatgtgacca gcagtctgag ggtcaacgcc    600
acagcgaatg atgttttcta ctgtacgttt tggagatcac agccagggca aaaccacaca    660
gcggagctga tcatcccaga actgcctgca acacatcctc acagaacagg actcactgg    720
gtgcttctgg gatccatcct gttgttcctc attgtagtgt ccacggtcct cctcttcttg    780
agaaaacaag tgagaatgct agatgtggag aaatgtggcg ttgaagatac aagctcaaaa    840
aaccgaaatg atacacaatt cgaggagacg taa                                  873
```

<210> SEQ ID NO 8
<211> LENGTH: 290
<212> TYPE: PRT
<213> ORGANISM: Mus musculus

<400> SEQUENCE: 8

```
Met Arg Ile Phe Ala Gly Ile Ile Phe Thr Ala Cys Cys His Leu Leu
1               5                   10                  15
Arg Ala Phe Thr Ile Thr Ala Pro Lys Asp Leu Tyr Val Val Glu Tyr
                20                  25                  30
```

Gly Ser Asn Val Thr Met Glu Cys Arg Phe Pro Val Glu Arg Glu Leu
             35                  40                  45

Asp Leu Leu Ala Leu Val Val Tyr Trp Glu Lys Glu Asp Glu Gln Val
 50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
                100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
        130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 9
<211> LENGTH: 867
<212> TYPE: DNA
<213> ORGANISM: Mus musculus

<400> SEQUENCE: 9
atgtgggtcc ggcaggtacc ctggtcattc acttgggctg tgctgcagtt gagctggcaa      60
tcagggtggc ttctagaggt ccccaatggg ccctggaggt ccctcacctt ctacccagcc     120
tggctcacag tgtcagaggg agcaaatgcc accttcacct gcagcttgtc caactggtcg     180
gaggatctta tgctgaactg gaaccgcctg agtcccagca accagactga aaaacaggcc     240
gccttctgta atggtttgag ccaacccgtc caggatgccc gcttccagat catacagctg     300
cccaacaggc atgacttcca catgaacatc cttgacacac ggcgcaatga cagtggcatc     360
tacctctgtg gggccatctc cctgcacccc aaggcaaaaa tcgaggagag ccctggagca     420
gagctcgtgg taacagagag aatcctggag acctcaacaa gatatcccag ccctcgccc      480 aaaccagaag gccggtttca aggcatggtc attggtatca tgagtgccct agtgggtatc     540
cctgtattgc tgctgctggc ctgggcccta gctgtcttct gctcaacaag tatgtcagag     600

| | |
|---|---|
| gccagaggag ctggaagcaa ggacgacact ctgaaggagg agccttcagc agcacctgtc | 660 |
| cctagtgtgg cctatgagga gctggacttc cagggacgag agaagacacc agagctccct | 720 |
| accgcctgtg tgcacacaga atatgccacc attgtcttca ctgaagggct gggtgcctcg | 780 |
| gccatgggac gtaggggctc agctgatggc ctgcagggtc ctcggcctcc aagacatgag | 840 |
| gatggacatt gttcttggcc tctttga | 867 |

<210> SEQ ID NO 10
<211> LENGTH: 288
<212> TYPE: PRT
<213> ORGANISM: Mus musculus

<400> SEQUENCE: 10

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 11
<211> LENGTH: 867
<212> TYPE: DNA
<213> ORGANISM: Macaca mulatta

<400> SEQUENCE: 11

```
atgcagatcc cacaggcacc ctggccggtc gtctgggcgg tgctacaact gggctggcgg    60
ccaggatggt tcttagaatc cccggacagg ccctggaacc cccccaccttc tccccagcc   120
ctgctcctgg tgaccgaagg agacaacgcc accttcacct gcagcttctc caacgcctcg   180
gagagcttcg tgctgaactg gtaccgcatg agccccagca accagacgga caagctggct   240
gccttccccg aggaccgcag ccagcccggc cgggactgcc gcttccgcgt cacacaactg   300
cccaacgggc gcgacttcca catgagcgtg gtcagggccc ggcgcaacga cagcggcacc   360
tacctctgcg gggccatctc cctggccccc aaggcgcaga tcaaagagag cctgcgggca   420
gagctcaggg tgacagagag aagggcagaa gtgcccacag cccaccccag ccctcaccc   480
aggccagctg ccagttcca agccctggtg gttggtgtcg tgggcggcct gctgggcagc   540
ctggtgctgc tagtctgggt cctggctgtc atctgctccc gggctgcaca agggaccata   600
gaagccaggc gcaccggcca gcccctgaag gaggacccct cggccgtgcc tgtgttctct   660
gtggactatg gggagctgga tttccagtgg cgagagaaga ccccggagcc cccggcaccc   720
tgtgtccctg agcagacgga gtacgccacc atcgtctttc ctagtgggct gggcacctcg   780
tccccggccc gcaggggctc agccgacggc cctcggagtc cccggccact gaggcctgag   840
gatggacact gctcttggcc cctctga                                       867
```

<210> SEQ ID NO 12  
<211> LENGTH: 288  
<212> TYPE: PRT  
<213> ORGANISM: Macaca mulatta

<400> SEQUENCE: 12

```
Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Pro Pro Thr Phe Ser Pro Ala Leu Leu Val Thr Glu Gly Asp
        35                  40                  45

Asn Ala Thr Phe Thr Cys Ser Phe Ser Asn Ala Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Arg Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
```

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
            245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
            275                 280                 285

<210> SEQ ID NO 13
<211> LENGTH: 864
<212> TYPE: DNA
<213> ORGANISM: Rattus norvegicus

<400> SEQUENCE: 13
atgtgggtcc agcaggtacc ctggtcattc acttgggctg tgctacagtt gagctggcaa      60
tcagggtggc ttctagaggt cctcaataag ccctggaggc ccctcacctt ctccccaacc     120
tggctcacag tgtcagaggg agcaaatgcc accttcacct gcagtttctc caactggtcg     180
gaggatctta agctgaactg gtaccgtctg agtcccagca accagactga aaaacaggcc     240
gccttctgca atggttacag ccagcccgtc cgggatgccc gcttccagat cgtacaactg     300
cccaacggac atgacttcca catgaacatc ctcgatgcac ggcgcaatga cagtggcatc     360
tacctctgtg gggccatctc cctgcctccc aaggcacaaa tcaaagagag tcctggagca     420
gagcttgtgg taacagagag aatcctggag accccaacaa gatatcccag accctcaccc     480
aagccagaag gccagtttca aggcttggtc attgtcatca tgagcgtcct agtgggtatc     540
cccgtgttgc tgctgctggc ctgggctctc gctgccttct gctcaacagg tatgtcagag     600
gccagagaag ctggacgcaa ggaagaccct ccgaaggagg cgcatgcagc agcccctgtt     660
cccagtgtgg cctacgagga gctggacttt cagggacgag agaagacacc agagcctgcc     720
ccctgtgtgc acacagaata cgccaccatt gtcttcactg aaggactgga tgcctcagcc     780
ataggacgta ggggctcagc tgatggccca cagggtcctc ggcctccaag acatgaggat     840
ggacactgct cttggcctct ttga                                            864

<210> SEQ ID NO 14
<211> LENGTH: 287
<212> TYPE: PRT
<213> ORGANISM: Rattus norvegicus

<400> SEQUENCE: 14

Met Trp Val Gln Gln Val Pro Trp Ser Phe Thr Trp Ala Val Leu Gln
1               5                   10                  15

Leu Ser Trp Gln Ser Gly Trp Leu Leu Glu Val Leu Asn Lys Pro Trp
            20                  25                  30

Arg Pro Leu Thr Phe Ser Pro Thr Trp Leu Thr Val Ser Glu Gly Ala
        35                  40                  45

Asn Ala Thr Phe Thr Cys Ser Phe Ser Asn Trp Ser Glu Asp Leu Lys
    50                  55                  60

Leu Asn Trp Tyr Arg Leu Ser Pro Ser Asn Gln Thr Glu Lys Gln Ala
65                  70                  75                  80

Ala Phe Cys Asn Gly Tyr Ser Gln Pro Val Arg Asp Ala Arg Phe Gln
                85                  90                  95

Ile Val Gln Leu Pro Asn Gly His Asp Phe His Met Asn Ile Leu Asp

```
            100                 105                 110
Ala Arg Arg Asn Asp Ser Gly Ile Tyr Leu Cys Gly Ala Ile Ser Leu
            115                 120                 125

Pro Pro Lys Ala Gln Ile Lys Glu Ser Pro Gly Ala Glu Leu Val Val
        130                 135                 140

Thr Glu Arg Ile Leu Glu Thr Pro Thr Arg Tyr Pro Arg Pro Ser Pro
145                 150                 155                 160

Lys Pro Glu Gly Gln Phe Gln Gly Leu Val Ile Val Ile Met Ser Val
                165                 170                 175

Leu Val Gly Ile Pro Val Leu Leu Leu Ala Trp Ala Leu Ala Ala
                180                 185                 190

Phe Cys Ser Thr Gly Met Ser Glu Ala Arg Glu Ala Gly Arg Lys Glu
            195                 200                 205

Asp Pro Pro Lys Glu Ala His Ala Ala Ala Pro Val Pro Ser Val Ala
        210                 215                 220

Tyr Glu Glu Leu Asp Phe Gln Gly Arg Glu Lys Thr Pro Glu Pro Ala
225                 230                 235                 240

Pro Cys Val His Thr Glu Tyr Ala Thr Ile Val Phe Thr Glu Gly Leu
                245                 250                 255

Asp Ala Ser Ala Ile Gly Arg Arg Gly Ser Ala Asp Gly Pro Gln Gly
                260                 265                 270

Pro Arg Pro Pro Arg His Glu Asp Gly His Cys Ser Trp Pro Leu
        275                 280                 285

<210> SEQ ID NO 15
<211> LENGTH: 867
<212> TYPE: DNA
<213> ORGANISM: Canis familiaris

<400> SEQUENCE: 15
atggggagcc ggcgggggcc ctggccgctc gtctgggccg tgctgcagct gggctggtgg      60
ccaggatggc tcctagactc ccctgacagg ccctggagcc cgctcacctt ctccccggcg     120
cagctcacgg tgcaggaggg agagaacgcc acgttcacct gcagcctggc cgacatcccc     180
gacagcttcg tgctcaactg gtaccgcctg agccccgca accagacgga caagctggcc     240
gccttccagg aggaccgcat cgagccgggc cgggacaggc gcttccgcgt catgcggctg     300
cccaacgggc gggacttcca catgagcatc gtcgctgcgc cctcaacga cagcggcatc     360 tacctgtgcg gggccatcta cctgccccc aacacacaga tcaacgagag tccccgcgca     420
gagctctccg tgacggagag aaccctggag ccccccacac agagcccag ccccccaccc     480 agactcagcg ccagttgca ggggctggtc atcggcgtca cgagcgtgct ggtgggtgtc     540
ctgctactgc tgctgctgac ctgggtcctg gccgctgtct tccccagggc cacccgaggt     600
gcctgtgtgt gcgggagcga ggacgagcct ctgaaggagg ccccgatgc agcgcccgtc     660 ttcaccctgg actacgggga gctggacttc agtggcgag agaagacgcc ggagcccccg     720
gcgccctgtg ccccggagca gaccgagtat gccaccatcg tcttcccggg caggccggcg     780
tccccgggcc gcagggcctc ggccagcagc ctgcagggag cccagcctcc gagccccgag     840
gacggacccg gcctgtggcc cctctga                                        867

<210> SEQ ID NO 16
<211> LENGTH: 288
<212> TYPE: PRT
<213> ORGANISM: Canis familiaris
```

<400> SEQUENCE: 16

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30

Ser Pro Leu Thr Phe Ser Pro Ala Gln Leu Thr Val Gln Glu Gly Glu
        35                  40                  45

Asn Ala Thr Phe Thr Cys Ser Leu Ala Asp Ile Pro Asp Ser Phe Val
    50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Met Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
    130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
            180                 185                 190

Val Phe Pro Arg Ala Thr Arg Gly Ala Cys Val Cys Gly Ser Glu Asp
            195                 200                 205

Glu Pro Leu Lys Glu Gly Pro Asp Ala Ala Pro Val Phe Thr Leu Asp
    210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Leu
        275                 280                 285

<210> SEQ ID NO 17
<211> LENGTH: 849
<212> TYPE: DNA
<213> ORGANISM: Bos taurus

<400> SEQUENCE: 17
atggggaccc cgcgggcgct gtggccactc gtctgggccg tgctgcagct gggctgctgg     60
ccaggatggc tcctagaggc ctccagcagg ccctggagcg ccctcacctt ctctcccccc    120
cggctggtcg tgcccgaggg agcgaatgcc accttcacct gcagcttctc agtaagccg     180 gagcgcttcg tcctcaactg gtaccgcaag agccccagca accagatgga caaactggcc    240
gccttccctg aggaccgcag ccagcccagc cgagaccggc gcttccgcgt cacgccgctg    300
cccgatgggc agcagtttaa catgagcatc gtggcggccc agcgcaatga cagcggcgtc    360
tacttctgcg gggccatcta cctgccaccc ggacgcagaa tcaacgagag ccacagcgca    420
gagctcatgg tgacagaggc ggtcctggag ccgccaacgg agcccccag ccccagccc     480

```
aggcctgagg gccagatgca gagcctggtc atcggcgtca caagcgtcct tctgggggtc    540
ctgctgctgc cgccactgat ctgggtcctg gccgcggtct tcctcagggc cactcgaggg    600
ggctgcgccc gcaggagcca agaccagcct ccgaaggagg gctgcccctc tgtgccggct    660
gtcacagtgg actacgggga gctggacttc agtggcggg agaagacccc ggagcccgcg    720
gctccctgcg tcccggagca gacagagtac gccaccatcg tcttcccagg ccgcagggcg    780
tccgccgaca gcccgcaggg gccctggcca ctgaggaccg aggatggaca ctgctcctgg    840
cccctctga                                                            849
```

<210> SEQ ID NO 18
<211> LENGTH: 282
<212> TYPE: PRT
<213> ORGANISM: Bos taurus

<400> SEQUENCE: 18

```
Met Gly Thr Pro Arg Ala Leu Trp Pro Leu Val Trp Ala Val Leu Gln
1               5                   10                  15

Leu Gly Cys Trp Pro Gly Trp Leu Leu Glu Ala Ser Ser Arg Pro Trp
            20                  25                  30

Ser Ala Leu Thr Phe Ser Pro Arg Leu Val Val Pro Glu Gly Ala
        35                  40                  45

Asn Ala Thr Phe Thr Cys Ser Phe Ser Ser Lys Pro Glu Arg Phe Val
50                  55                  60

Leu Asn Trp Tyr Arg Lys Ser Pro Ser Asn Gln Met Asp Lys Leu Ala
65                  70                  75                  80

Ala Phe Pro Glu Asp Arg Ser Gln Pro Ser Arg Asp Arg Arg Phe Arg
                85                  90                  95

Val Thr Pro Leu Pro Asp Gly Gln Gln Phe Asn Met Ser Ile Val Ala
            100                 105                 110

Ala Gln Arg Asn Asp Ser Gly Val Tyr Phe Cys Gly Ala Ile Tyr Leu
        115                 120                 125

Pro Pro Arg Thr Gln Ile Asn Glu Ser His Ser Ala Glu Leu Met Val
130                 135                 140

Thr Glu Ala Val Leu Glu Pro Pro Thr Glu Pro Ser Pro Gln Pro
145                 150                 155                 160

Arg Pro Glu Gly Gln Met Gln Ser Leu Val Ile Gly Val Thr Ser Val
                165                 170                 175

Leu Leu Gly Val Leu Leu Leu Pro Pro Leu Ile Trp Val Leu Ala Ala
            180                 185                 190

Val Phe Leu Arg Ala Thr Arg Gly Gly Cys Ala Arg Arg Ser Gln Asp
        195                 200                 205

Gln Pro Pro Lys Glu Gly Cys Pro Ser Val Pro Ala Val Thr Val Asp
    210                 215                 220

Tyr Gly Glu Leu Asp Phe Gln Trp Arg Glu Lys Thr Pro Glu Pro Ala
225                 230                 235                 240

Ala Pro Cys Val Pro Glu Gln Thr Glu Tyr Ala Thr Ile Val Phe Pro
                245                 250                 255

Gly Arg Arg Ala Ser Ala Asp Ser Pro Gln Gly Pro Trp Pro Leu Arg
            260                 265                 270

Thr Glu Asp Gly His Cys Ser Trp Pro Leu
        275                 280
```

<210> SEQ ID NO 19

```
<211> LENGTH: 11
<212> TYPE: PRT
<213> ORGANISM: Artificial Sequence
<220> FEATURE:
<223> OTHER INFORMATION: /note="Description of Artificial Sequence:
      BDC2.5 tetramer peptide sequence"

<400> SEQUENCE: 19

Ala His His Pro Ile Trp Ala Arg Met Asp Ala
1               5                   10

<210> SEQ ID NO 20
<211> LENGTH: 9
<212> TYPE: PRT
<213> ORGANISM: Artificial Sequence
<220> FEATURE:
<223> OTHER INFORMATION: /note="Description of Artificial Sequence: IGRP
      tetramer peptide sequence"

<400> SEQUENCE: 20

Lys Tyr Asn Lys Ala Asn Val Phe Leu
1               5
```

REGULATORY T CELL PD-1 MODULATION FOR REGULATING T CELL EFFECTOR IMMUNE RESPONSES

CROSS-REFERENCE TO RELATED APPLICATIONS

This application claims the benefit of U.S. Provisional Application No. 62/242,509, filed on 16 Oct. 2015; the entire contents of said application are incorporated herein in their entirety by this reference.

STATEMENT OF RIGHTS

This invention was made with government support under grant numbers P01 AI56299, R01 40614, R37 AI38310, R01 DK 089125, P01 AI108545, CA047904, and 1F31 DK105624-01A1 awarded by the National Institutes of Health. The government has certain rights in the invention.

BACKGROUND OF THE INVENTION

CD4+FoxP3+ T regulatory cells (Tregs) critically control immune responses by restraining immune effector cells (Hori et al. (2003) *Science* 299:1057-1061; Fontenot et al. (2003) *Nat. Immunol.* 4:330-336; Vignali et al. (2008) *Nat. Rev. Immunol.* 8:523-532; Josefowicz et al. (2012) *Annu. Rev. Immunol.* 30:531-564; Shevach and Thornton (2014) *Immunol. Rev.* 259:88-102; Smigiel et al. (2014) *Immunol. Rev.* 259:40-59). Beyond ensuring immune homeostasis, Tregs play significant roles in many diseases including cancer, viral infection, and autoimmunity, making them attractive targets for therapeutic intervention (Rosenblum et al. (2012) *Science Transl. Med.* 4:125sr121; Chapman and Chi (2014) *Immunother.* 6:1295-1311; Bluestone et al. (2015) 1 *Clin. Invest.* 125:220-2260). However, in order to modulate Tregs effectively, the signals that control Treg activity need to be elucidated.

Co-inhibitory molecules, such as CTLA-4 and PD-1, suppress immune responses in cancer, viral infection and autoimmunity (Walker and Sansom (2011) *Nat. Rev. Immunol.* 11:852-863; Francisco et al. (2009) *Immunol. Rev.* 236:219-242; Topalian et al. (2015) *Cancer Cell* 27:450-461; Leach et al. (1996) *Science* 271:1734-1736; Hodi et al. (2010) *N. Engl. J. Med.* 363:711-723; Bour-Jordan et al. (2011) *Immunol. Rev.* 241:180-205; Barber et al. (2006) *Nature* 439:682-687; Flies et al. (2011) *Yale J. Biol. Med.* 84:409-421; Jin et al. (2011) *Curr. Top. Microbiol. Immunol.* 350:17-37; Topalian et al. (2012) *N. Engl. J. Med.* 366:2443-2454; Brahmer (2010) *J. Clin. Oncol.* 28:3167-3175; Powles et al. (2014) *Nature* 515:558-562). CTLA-4 on Tregs has multifaceted roles in regulating Treg expansion and function in autoimmunity and cancer (Walker and Sansom (2011) *Nat. Rev. Immunol.* 11:852-863; Wing et al. (2008) *Science* 322:271-275; Peggs et al. (2009) *Clin. Exp. Immunol.* 157: 9-19). Although the PD-1 pathway is a key mediator of T cell tolerance and exhaustion (Bour-Jordan et al. (2011) *Immunol. Rev.* 241:180-205; Flies et al. (2011) *Yale J Biol. Med.* 84:409-421; Jin et al. (2011) *Curr. Top. Microbiol. Immunol.* 350:17-37; Pauken and Wherry (2015) *Trends Immunol.* 36:265-276), it is unclear clear how PD-1 controls Treg activation and effector function. PD-1 is induced on conventional CD4+ and CD8+ T cells, as well as Tregs, upon their activation (Francisco et al. (2009) *Immunol. Rev.* 236:219-242; Jin et al. (2011) *Curr. Top. Microbiol. Immunol.* 350:17-37; Okazaki et al. (2013) *Nat. Immunol.* 14:1212-1218; Riley (2009) *Immunol. Rev.* 229:114-125). PD-1 signals also are involved in regulating induced Treg cell development (Francisco et al. (2009) *J Exp. Med.* 206:3015-3029; Wang et al. (2008) *Proc. Natl. Acad. Sci. U.S.A.* 105:9331-9336; Amarnath et al. (2011) *Science Trans. Med.* 3:111ra120). Moreover, the role of PD-1 on effector Tregs in homeostasis and disease remains poorly understood. Thus, a great need in the art exists for understanding the role of PD-1 signaling within specific immune cell populations, such as in Tregs, and for modulating PD-1 signaling in such immune cell subpopulations to regulate immune responses by immune effector cells, such as effector T cells.

SUMMARY OF THE INVENTION

The present invention is based, at least in part, on the discovery that the inhibition or blockade of PD-1 specifically within the regulatory T cell (Tregs) population of immune cells results in the Tregs having increased function (i.e., increased suppression of effector T cells (Teffs)). Loss of PD-1 activity in all cells of a mouse resulted in higher frequencies of Tregs and increased numbers of Tregs, and these PD-1 deficient Tregs suppressed Tconv more potently than wild type (WT) Tregs. Treg-specific and inducible Treg-specific PD-1 knockout mice were generated and used to determine that PD-1 deficiency on Tregs alone resulted in increased vulnerability to opportunistic infection. Induced deletion of PD-1 on Tregs increased the capacity of Tregs to inhibit effector T cells in vitro and these more potent Tregs delayed the onset and severity of autoimmune diseases, such as experimental autoimmune encephalitis and type I diabetes. It is therefore demonstrated herein that when PD-1 is lost on cells whose activity is to suppress immune responses (e.g., Tregs), the consequence is a stronger suppressor cell. Moreover, loss of PD-1 specifically in the Treg subpopulation of immune cells causes enhanced anti-tumor responses.

In one aspect of the present invention, a method for modulating effector function of effector T cells (Teffs) by regulatory T cells (Tregs), comprising a) selectively modulating the expression and/or activity of PD-1 in Tregs; and b) contacting the Tregs with Teffs, thereby modulating effector function of the Teffs by the Tregs is provided.

Numerous embodiments are further provided that can be applied to any aspect of the present invention described herein. For example, in one embodiment, the Tregs and/or Teffs are isolated from a subject. In another embodiment, the PD-1 expression and/or activity is selectively modulated in the Tregs in vitro or ex vivo. In still another embodiment, the Tregs contact the Teffs in vitro or ex vivo. In yet another embodiment, the Tregs and/or Teffs are administered to a subject. In another embodiment, the Tregs and/or Teffs are present within a subject. In still another embodiment, the PD-1 expression and/or activity is selectively modulated in the Tregs in vivo. In yet another embodiment, the Tregs contact the Teffs or in vivo. In another embodiment, the Tregs decrease effector function of the Teffs. In still another embodiment, the PD-1 expression and/or activity is selectively inhibited or blocked in the Tregs in vitro or ex vivo. In yet another embodiment, the PD-1 expression and/or activity is selectively inhibited or blocked in the Tregs in vivo. In another embodiment, the Tregs express a PD-1 nucleic acid encoding a non-functional PD-1 protein. In still another embodiment, the PD-1 nucleic acid is expressed from a recombinantly modified PD-1 allele. In yet another embodiment, the PD-1 nucleic acid is inducibly expressed. In another embodiment, the Tregs only express a PD-1 nucleic acid encoding a non-functional PD-1 protein or only express a non-functional PD-1 protein. In still another embodiment, the non-functional PD-1 protein lacks the ability to bind PD-L1, bind PD-L2, transmit an inhibitory signal, or combination thereof. In yet another embodiment, the Tregs are contacted with at least one agent that selectively modulates (e.g., inhibits or blocks) the expression and/or activity of PD-1 (e.g., at least one agent is selected from the group consisting of a PD-1 blocking antibody, a non-activating form of PD-L1, a non-activating form of PD-L2, a soluble form of a PD-1 natural binding partner, a nucleic acid molecule that blocks PD-1 transcription or translation, a small molecule PD-1 antagonist, a PD-1 inverse agonist, and combinations thereof). In another embodiment the at least one agent is a PD-1 blocking antibody selected from the group consisting of: anti-PD-1 antibodies that block the interaction between PD-1 and PD-L1 without blocking the interaction between PD-1 and PD-L2; anti-PD-1 antibodies that block the interaction between PD-1 and PD-L2 without blocking the interaction between PD-1 and PD-L1; and anti-PD-1 antibodies that block both the interaction between PD-1 and PD-L1 and the interaction between PD-L1 and PD-L2, optionally wherein the antibody, or antigen binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof.

Numerous other agents are contemplated. For example, in one embodiment, the at least one agent is an exogenous nucleic acid comprising a) an engineered, non-naturally occurring Clustered Regularly Interspaced Short Palindromic Repeats (CRISPR) guide RNA that hybridizes with PD-1 genomic nucleic acid sequence and/or b) a nucleotide sequence encoding a Type-II Cas9 protein, optionally wherein the cells are transgenic for expressing a Cas9 protein. In another embodiment, the at least one agent comprises an RNA interfering agent which inhibits or blocks PD-1 expression or activity, optionally wherein the RNA interfering agent is expressed constitutively or inducibly. In still another embodiment, the RNA interfering agent is a small interfering RNA (siRNA), small hairpin RNA (shRNA), microRNA (miRNA), or a piwiRNA (piRNA). In yet another embodiment, the at least one agent comprises an antisense oligonucleotide complementary to PD-1. In another embodiment, the at least one agent comprises a peptide or peptidomimetic that inhibits or blocks PD-1 expression or activity. In still another embodiment, the at least one agent comprises an aptamer that inhibits or blocks PD-1 expression or activity. In yet another embodiment, the at least one agent is inducibly expressed within the Tregs. In another embodiment, the at least one agent comprises a small molecule that inhibits or blocks PD-1 expression or activity. In still another embodiment, the at least one agent is a bispecific or multispecific antibody, or antigen-binding fragment thereof, selective for both PD-1 and a Treg cell surface protein, optionally wherein the antibody, or antigen binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof.

As described above, numerous embodiments are further provided that can be applied to any aspect of the present invention described herein are contemplated. For example, in one embodiment, the Treg cell surface protein is selected from the group consisting of CD25, GITR, TIGIT, CTLA-4, neuropilin, OX40, LAG3, and combinations thereof. In another embodiment, the expression and/or activity of PD-1 is specifically inhibited or blocked in the Tregs. In still another embodiment, the Tregs are administered to a subject having a disorder in need of increased suppression of effector function of Teffs by the Tregs (e.g., a disorder is selected from the group consisting of adoptive cell therapy, solid organ transplantation, autoimmune disorder, allergic disorder, hypersensitivity disorder, graft-versus-host disease (GVHD), solid organ transplantation rejection, vasculitis, systemic lupus erythematosus (SLE), type 1 diabetes (T1D), multiple sclerosis (MS), psoriasis, rheumatoid arthritis (RA), inflammatory bowel disease (IBD), and allergic asthma, ankylosing spondylitis (AS), giant cell arteritis (GCA), stem cell therapy, and gene therapy). For example, recipients of gene and/or stem cell therapy to prevent stem cell rejection or loss of replacement therapy (e.g., factor VIII) can benefit. In yet another embodiment, the Tregs are administered focally or systemically. In another embodiment, the focal administration is intratumoral or subcutaneous. In still another embodiment, the systemic administration is intravenous, intramuscular, intraperitoneal, or intraarticular. In yet another embodiment, the Tregs administered to the subject are autologous, syngeneic, allogeneic, or xenogeneic. In another embodiment, the Tregs administered to the subject are administered in a pharmaceutically acceptable formulation. In still another embodiment, the Tregs are administered to the subject with one or more additional agents that downregulate an immune response or treats the disorder. In yet another embodiment, the effector function of Teffs is reduced by at least 1.2-fold after contact with the Tregs as compared to before contact with the Tregs. In another embodiment, Treg number, Treg activity, Treg FOXP3 expression, Tregs to Teffs ratio, or combination thereof is increased by at least 1.2-fold after inhibiting or blocking the expression and/or activity of PD-1 in the Tregs.

Similarly, in one embodiment, the Tregs increase effector function of the Teffs. For example, increased PD-1 expression in Tregs can decrease the number of Tregs and/or decrease/inhibit Treg function, thereby increasing the effector function of the Teffs. In another embodiment, the PD-1 expression and/or activity is selectively increased in the Tregs in vitro or ex vivo. In still another embodiment, the PD-1 expression and/or activity is selectively increased in the Tregs in vivo. In yet another embodiment, the Tregs are contacted with at least one agent that selectively increases the expression and/or activity of PD-1. In another embodiment, the at least one agent is selected from the group consisting of a PD-1 nucleic acid, a PD-1 protein, an activating anti-PD-1 antibody, a nucleic acid molecule that increases PD-1 transcription or translation, and a small molecule PD-1 agonist, and combinations thereof. In still another embodiment, the at least one agent is inducibly expressed within the Tregs. In yet another embodiment, the activating anti-PD-1 antibody is a bispecific or multispecific antibody, or antigen-binding fragment thereof, selective for both PD-1 and a Treg cell surface protein, optionally wherein the antibody, or antigen binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof. In another embodiment, the Treg cell surface protein is selected from the group consisting of CD25, GITR, TIGIT, CTLA-4, neuropilin, OX-40, LAG3, and combinations thereof. In still another embodiment, the antibody, or antigen binding fragment thereof, is conjugated to a cytotoxic agent. In yet another embodiment, the cytotoxic agent is selected from the group consisting of a chemotherapeutic agent, a biologic agent, a toxin, and a radioactive isotope. In another embodiment, the expression and/or activity of PD-1 is specifically increased in the Tregs. In still another embodiment, the Tregs are administered to a subject having a disorder in need of decreased suppression of effector function of Teffs by the Tregs. In yet another embodiment, the disorder is selected from the group consisting of an acute infection, a viral infection, a bacterial infection, a protozoan infection, a helminth infection, and an immunosuppressive disease. In another embodiment, the Tregs are administered focally or systemically. In one embodiment, the focal administration is intratumoral or subcutaneous. In another embodiment, the systemic administration is intravenous, intramuscular, intraperitoneal, or intraarticular. In still another embodiment, the Tregs administered to the subject are autologous, syngeneic, allogeneic, or xenogeneic. In yet another embodiment, the Tregs administered to the subject are administered in a pharmaceutically acceptable formulation. In another embodiment, the Tregs are administered to the subject with one or more additional agents that upregulate an immune response or treats the disorder. In still another embodiment, the additional agent is an immune checkpoint inhibitor (e.g., at least one anti-immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, A2aR, and combinations thereof). In yet another embodiment, the at least one anti-immune checkpoint is selected from the group consisting of PD-L1, PD-L2, CTLA-4, and combinations thereof. In another embodiment, the effector function of Teffs is increased by at least 1.2-fold after contact with the Tregs as compared to before contact with the Tregs. In still another embodiment, Treg number, Treg activity, Treg FOXP3 expression, Tregs to Teffs ratio, or combination thereof is decreased by at least 1.2-fold after increasing the expression and/or activity of PD-1 in the Tregs.

Another embodiment that can be applied to any aspect of the present invention described herein involves Tregs that further express a reporter, optionally wherein the reporter is a fluorescent protein, a heavy metal tag, or a radiolabel. For example, a heavy metal tag, radiolabeled isotope, and the like, allows for in vivo tracking. Similarly, Tregs can be mitotic, terminally differentiated, post-mitotic, unactivated, activated, or a combinations thereof. In another embodiment, Tregs are natural Tregs (nTregs) or induced Tregs (iTregs). In still another embodiment, the subject is a mammal. In yet another embodiment, the mammal is an animal model of the disorder. In another embodiment, the mammal is a rodent or a human.

In another aspect of the present invention, a method of reducing or stopping hyperproliferative growth of cancer cells comprising a) selectively inhibiting or blocking the expression and/or activity of PD-1 in Tregs; and b) contacting a source of cancer cells and Teffs with the Tregs, thereby reducing or stopping hyperproliferative growth of the cancer cells is provided.

Numerous embodiments are further provided that can be applied to any aspect of the present invention described herein. For example, in one embodiment the Tregs are isolated from a subject. In another embodiment, the PD-1 expression and/or activity is selectively inhibited or blocked in the Tregs in vitro or ex vivo. In still another embodiment, the Tregs contact an in vitro or ex vivo source of cancer cells and Teffs. In yet another embodiment, the Tregs are administered to a subject. In another embodiment, the Tregs are present within a subject. In still another embodiment, the PD-1 expression and/or activity is selectively inhibited or blocked in the Tregs in vivo. In yet another embodiment, the Tregs contact an in vivo source of cancer cells and Teffs. In another embodiment, the Tregs increase effector function of Teffs against the cancer cells. In still another embodiment, the Tregs die, convert to Teffs, or alter Treg-to-Teff effects on the cancer cells. In yet another embodiment, the Tregs are overstimulated and/or overactivated and die. In another embodiment, the Tregs express a PD-1 nucleic acid encoding a non-functional PD-1 protein. In still another embodiment, the PD-1 nucleic acid is expressed from a recombinantly modified PD-1 allele. In yet another embodiment, the PD-1 nucleic acid is inducibly expressed. In another embodiment, the Tregs only express a PD-1 nucleic acid encoding a non-functional PD-1 protein or only express a non-functional PD-1 protein. In still another embodiment, the non-functional PD-1 protein lacks the ability to bind PD-L1, bind PD-L2, transmit an inhibitor signal, or combination thereof. In yet another embodiment, the Tregs are contacted with at least one agent that selectively inhibits or blocks the expression and/or activity of PD-1.

Many exemplary agents are contemplated. For example, in one embodiment, the at least one agent is selected from the group consisting of a PD-1 blocking antibody, a non-activating form of PD-L1, a non-activating form of PD-L2, a soluble form of a PD-1 natural binding partner, a nucleic acid molecule that blocks PD-1 transcription or translation, a small molecule PD-1 antagonist, and combinations thereof. In another embodiment, the at least one agent is a PD-1 blocking antibody selected from the group consisting of: anti-PD-1 antibodies that block the interaction between PD-1 and PD-L1 without blocking the interaction between PD-1 and PD-L2; anti-PD-1 antibodies that block the interaction between PD-1 and PD-L2 without blocking the interaction between PD-1 and PD-L1; and anti-PD-1 antibodies that block both the interaction between PD-1 and PD-L1 and the interaction between PD-L1 and PD-L2, optionally wherein the antibody, or antigen binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof. In still another embodiment, the at least one agent is an exogenous nucleic acid comprising a) an engineered, non-naturally occurring Clustered Regularly Interspaced Short Palindromic Repeats (CRISPR) guide RNA that hybridizes with PD-1 genomic nucleic acid sequence and/or b) a nucleotide sequence encoding a Type-II Cas9 protein, optionally wherein the cells are transgenic for expressing a Cas9 protein. In yet another embodiment, the at least one agent comprises an RNA interfering agent which inhibits or blocks PD-1 expression or activity. In another embodiment, the RNA interfering agent is a small interfering RNA (siRNA), small hairpin RNA (shRNA), microRNA (miRNA), or a piwiRNA (piRNA). In still another embodiment, the at least one agent comprises an antisense oligonucleotide complementary to PD-1. In yet another embodiment, the at least one agent comprises a peptide or peptidomimetic that inhibits or blocks PD-1 expression or activity. In another embodiment, the at least one agent comprises an aptamer that inhibits or blocks PD-1 expression or activity. In still another embodiment, the at least one agent is inducibly expressed within the Tregs. In yet another embodiment, the at least one agent comprises a small molecule that inhibits or blocks PD-1 expression or activity. In another embodiment, the at least one agent is a bispecific or multispecific antibody, or antigen-binding fragment thereof, selective for both PD-1 and a Treg cell surface protein, optionally wherein the antibody, or antigen binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof.

Similarly, in one embodiment, the Treg cell surface protein is selected from the group consisting of CD25, GITR, TIGIT, CTLA-4, neuropilin, OX-40, LAG3, and combinations thereof. In another embodiment, the expression and/or activity of PD-1 is specifically inhibited or blocked specifically in the Tregs. In still another embodiment, the Tregs are administered to a subject having cancer. In yet another embodiment, the cancer is selected from the group consisting of a solid tumor and a hematologic cancer. In another embodiment, the Tregs are administered focally or systemically. In still another embodiment, the focal administration is intratumoral or subcutaneous. In yet another embodiment, the systemic administration is intravenous, intramuscular, or intraperitoneal. In another embodiment, the Tregs administered to the subject are autologous, syngeneic, allogeneic, or xenogeneic. In still another embodiment, the Tregs administered to the subject are administered in a pharmaceutically acceptable formulation. In yet another embodiment, the Tregs are administered to the subject with one or more additional anti-cancer agents, optionally wherein the one or more additional anti-cancer agents is selected from the group consisting of immunotherapy, immune checkpoint inhibition, a vaccine, chemotherapy, radiation, epigenetic modifiers, and targeted therapy. In another embodiment, the additional agent is an immune checkpoint inhibitor (e.g., at least one anti-immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, A2aR, and combinations thereof). In still another embodiment, the at least one anti-immune checkpoint is selected from the group consisting of PD-L1, PD-L2, CTLA-4, and combinations thereof. In yet another embodiment, the effector function of Teffs is increased by at least 1.2-fold after contact with the Tregs as compared to before contact with the Tregs. In another embodiment, Treg number, Treg activity, Treg FOXP3 expression, Tregs to Teffs ratio, or combination thereof is modified by at least 1.2-fold after inhibiting or blocking the expression and/or activity of PD-1 in the Tregs. In still another embodiment, the Tregs further express a reporter, optionally wherein the reporter is a fluorescent protein. In yet another embodiment, the Tregs are mitotic, terminally differentiated, post-mitotic, unactivated, activated, or a combinations thereof. In another embodiment, the Tregs are natural Tregs (nTregs) or induced Tregs (iTregs). In still another embodiment, the subject is a mammal. In yet another embodiment, the mammal is an animal model of cancer. In another embodiment, the mammal is a rodent or a human.

In still another aspect of the present invention, a method of increasing the effector function of effector T cells (Teffs) comprising contacting Teffs with a bispecific antibody selective for both PD-1 and a Teff cell surface protein, thereby increasing the effector function of the Teffs, is provided.

Numerous embodiments are further provided that can be applied to any aspect of the present invention described herein. For example, in one embodiment the Teffs are isolated from a subject. In another embodiment, the PD-1 expression and/or activity is selectively inhibited or blocked in the Teffs in vitro or ex vivo. In still another embodiment, the Teffs contact an in vitro or ex vivo source of cancer cells. In yet another embodiment, the Teffs are administered to a subject. In another embodiment, the Teffs are present within a subject. In still another embodiment, the PD-1 expression and/or activity is selectively inhibited or blocked in the Teffs in vivo. In yet another embodiment, the Teffs contact an in vivo source of cancer cells. In another embodiment, the Teffs have increased effector function against cancer cells. In still another embodiment, the bispecific antibody selective for both PD-1 and a Teff cell surface protein, or antigen-binding fragment thereof, is a PD-1 blocking antibody selected from the group consisting of: i) anti-PD-1 antibodies that block the interaction between PD-1 and PD-L1 without blocking the interaction between PD-1 and PD-L2; ii) anti-PD-1 antibodies that block the interaction between PD-1 and PD-L2 without blocking the interaction between PD-1 and PD-L1; iii) anti-PD-1 antibodies that block both the interaction between PD-1 and PD-L1 and the interaction between PD-L1 and PD-L2; and iv) an antigen-binding fragment thereof. In yet another embodiment, the bispecific antibody selective for both PD-1 and a Teff cell surface protein, or antigen-binding fragment thereof, is murine, chimeric, humanized, composite, human, detectably labeled, comprises an effector domain, comprises an Fc domain, an Fv, an F(ab')2, an Fab', an dsFv, an scFv, an sc(Fv)2, a diabody, or any combination thereof. In another embodiment, the Teff cell surface protein is selected from the group consisting of CD8, CD107, CD244, CX3CR1, and combinations thereof. In still another embodiment, the expression and/or activity of PD-1 is specifically inhibited or blocked specifically in the Teffs. In yet another embodiment, the Teffs are administered to a subject having cancer, optionally wherein the administered Teffs reduce or stop hyperproliferative growth of cancer cells in the subject having cancer. In another embodiment, the cancer is selected from the group consisting of a solid tumor and a hematologic cancer. In still another embodiment, the Teffs are administered focally or systemically, such as focal administration that is intratumoral or subcutaneous or systemic administration that is intravenous, intramuscular, or intraperitoneal.

Similarly, in one embodiment, the Teffs administered to the subject are autologous, syngeneic, allogeneic, or xenogeneic. In another embodiment, the Teffs administered to the subject are administered in a pharmaceutically acceptable formulation. In still another embodiment, the Teffs are administered to the subject with one or more additional anti-cancer agents, optionally wherein the one or more additional anti-cancer agents is selected from the group consisting of immunotherapy, immune checkpoint inhibition, a vaccine, chemotherapy, radiation, epigenetic modifiers, and targeted therapy. In yet another embodiment, the additional agent is an immune checkpoint inhibitor. In another embodiment, the at least one anti-immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, A2aR, and combinations thereof. In still another embodiment, the at least one anti-immune checkpoint is selected from the group consisting of PD-L1, PD-L2, CTLA-4, and combinations thereof. In yet another embodiment, the effector function of Teffs is increased by at least 1.2-fold after contact with the bispecific antibody selective for both PD-1 and a Teff cell surface protein. In another embodiment, the Teffs further express a reporter, optionally wherein the reporter is a fluorescent protein. In still another embodiment, the Teffs are mitotic, terminally differentiated, post-mitotic, effector memory cells, unactivated, activated, or a combinations thereof. In another embodiment, the subject is a mammal. In still another embodiment, the mammal is an animal model of cancer. In yet another embodiment, the mammal is a rodent or a human.

Figure 1:
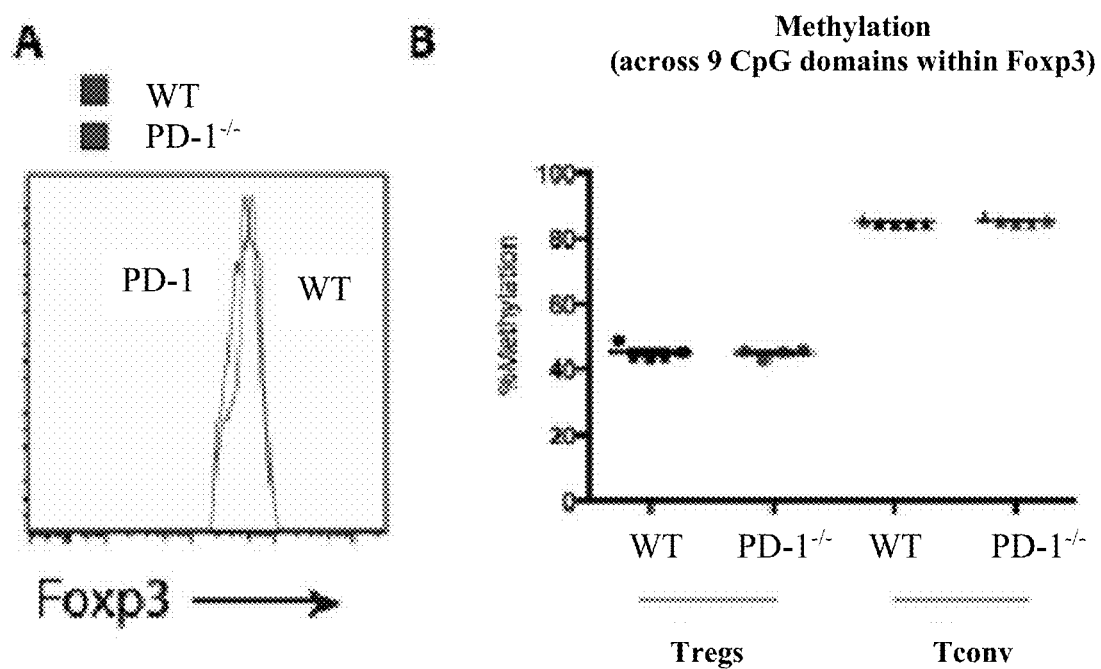
FIG. 1 includes 2 panels, identified as panels A and B, which show a comparison of FoxP3 expression and Treg-specific methylation in WT and PD-1$^{-/-}$ T cells. Panel A shows the expression of FoxP3 in WT or PD-1$^{-/-}$ Tregs from spleens. Panel B shows the results of TSDR methylation analysis of the Treg-specific demethylated region, TSDR, across 9 CpG regions. The results are representative of 2 experiments (n=5 mice per group) and p-values are as follows: *<0.05; <0.01; and *<0.001.

Note that for every figure containing a histogram, the bars from left to right for each discrete measurement correspond to the figure boxes from top to bottom in the figure legend as indicated unless otherwise described.

DETAILED DESCRIPTION OF THE INVENTION

The PD-1/PD-L co-inhibitory pathway plays a key role in regulating immune responses among a number of immune cell types. However, the role of PD-1 signaling and resulting effects on immune function within specific immune cell populations (e.g., Tregs) remains unclear. It is demonstrated herein that the inhibition or blockade of PD-1 specifically within the regulatory T cell (Tregs) population of immune cells results in the Tregs having increased function (i.e., increased suppression of effector T cells (Teffs)). In this manner, modulating PD-1 expression and/or activity on Tregs can, either alone or in combination with effects on Teffs, regulate effector T cell immune responses. Accordingly, the methods of the present invention provide options for regulating immune responses based on selectively or specifically modulating PD-1 expression and/or activity specifically with the Treg subpopulation of immune cells.

I. Definitions

The articles "a" and "an" are used herein to refer to one or to more than one (i.e. to at least one) of the grammatical object of the article. By way of example, "an element" means one element or more than one element.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a tumor or autoimmune sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a biomarker refers to the presence of mutations or allelic variants within a biomarker nucleic acid or protein, e.g., mutations which affect expression or activity of a marker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. The properties recited herein for antibodies and antibody fragments also apply to Fc fusion proteins described herein.

The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., PD-1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. (1998) *Nat. Biotechnol.* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to PD-1 polypeptides or fragments thereof. They may also be selective for such antigens such that they can distinguish such antigens from closely related antigens, such as other CD28/CTLA-4 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

As used herein, a "blocking" agent or an "antagonist" is one which inhibits or reduces at least one biological activity of the antigen(s) it binds. For example, an anti-PD-1 antibody binds PD-1 and inhibits the ability of PD-1 to bind one or more ligands, for example, PD-L1 and/or PD-L2. In certain embodiments, the blocking antibodies or antagonist antibodies or fragments thereof described herein substantially or completely inhibit a given biological activity of the antigen(s). In certain embodiments, the term "inverse agonist" is used to refer to an agent that promotes the opposite action to normal. For example, a PD-1 inverse agonist can promote co-stimulation as opposed to co-inhibition of immune responses.

The term "biomarker" or "marker" refers to a measurable entity of the present invention that has been determined to relate to Treg function and/or immune responses (e.g., PD-1 expression and/or activity alone or in combination with one or more other additional agents, such as immunomodulatory agents, anti-cancer agents, effector T cells, and the like). Biomarkers can include, without limitation, cell types (e.g., Tregs and/or Tcons), cell ratios (e.g., Tregs to Tconvs ratio), nucleic acids (e.g., genomic nucleic acids and/or transcribed nucleic acids) and proteins, particularly those provided in Table 1. Biomarkers can further include immunological targets or agents that downregulate unwanted immune reactions in order to treat the immune disorder of interest as described further herein.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit). In certain embodiments, body fluids comprising lymphocytes, such as T lymphocytes and subpopulations thereof, are used.

The term "bispecific antibody" or "multispecific antibody" refers to an antibody that recognized more than one epitope. Such antibodies are useful for targeting different proteins using the same agent. Methods of making such antibodies are well-known in art (see, at least U.S. Pat. Nos. 5,798,229; 5,989,830; and Holliger et al. (2005) *Nat. Biotech.* 23:1126-1136). For example, targeting PD-1 in addition to a Treg marker preferentially localizes an anti-PD-1 antibody (e.g., blocking antibody or agonizing antibody) to Tregs to thereby selectively target PD-1 on Treg immune cell populations from other cell types expressing PD-1.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. The term "cancer" includes premalignant, as well as malignant, cancers. The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control immune disorder patient (can be stored sample or previous sample measurement) with a known outcome; normal tissue or cells isolated from a subject, such as a normal patient or the immune disorder patient, cultured primary cells/tissues isolated from a subject such as a normal subject or the immune disorder patient, adjacent normal cells/tissues obtained from the same organ or body location of the immune disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care immune disorder therapy). It will be understood by those of skill in the art that such control samples and reference standard expression product levels can be used in combination as controls in the methods of the present invention. In one embodiment, the control may comprise normal or non-immune disorder cell/tissue sample. In another preferred embodiment, the control may comprise an expression level for a set of patients, such as a set of immune disorder patients, or for a set of immune disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having an immune disorder that has responded to a treatment of interest. In another embodiment, the control may also comprise a measured value for example, average level of expression of a particular gene in a population compared to the level of expression of a housekeeping gene in the same population. Such a population may comprise normal subjects, immune disorder patients who have not undergone any treatment (i.e., treatment naive), immune disorder patients undergoing standard of care therapy, or patients having an immune disorder that has responded to a treatment of interest. In another preferred embodiment, the control comprises a ratio transformation of expression product levels, including but not limited to determining a ratio of expression product levels of two cell types and/or genes in the test sample and comparing it to any suitable ratio of the same two cell types and/or genes in a reference standard; determining expression product levels of the two or more cell types and/or genes in the test sample and determining a difference in expression product levels in any suitable control; and determining expression product levels of the two or more cell types and/or genes in the test sample, normalizing their expression to expression of housekeeping cell types and/or genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with the immune disorder. In one embodiment a control expression product level is established wherein higher or lower levels of expression product relative to, for instance, a particular percentile, are used as the basis for predicting outcome. In another preferred embodiment, a control expression product level is established using expression product levels from immune disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with an immune disorder, or from a corresponding non-immune disorder tissue in the same subject who has an immune disorder.

The term "determining a suitable treatment regimen for the subject" is taken to mean the determination of a treatment regimen (i.e., a single therapy or a combination of different therapies that are used for the prevention and/or treatment of an immune disorder in the subject) for a subject that is started, modified and/or ended based or essentially based or at least partially based on the results of the analysis according to the present invention. One example is determining whether to provide Tregs modified to modulate PD-1 expression against an immune disorder. The determination can, in addition to the results of the analysis according to the present invention such as based on how high PD-1 expression or activity is in the initial Treg population, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the cell types in which they are expressed. Expression data and gene expression levels can be stored on computer readable media, e.g., the computer readable medium used in conjunction with a microarray or chip reading device. Such expression data can be manipulated to generate expression signatures.

A molecule or cell is "fixed" or "affixed" to a substrate if it is covalently or non-covalently associated with the substrate such that the substrate can be rinsed with a fluid (e.g. standard saline citrate, pH 7.4) without a substantial fraction of the molecule or cell dissociating from the substrate.

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the invention, such as a recombinant expression vector described herein, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. For example, antigen-reactive T cells are T cells that selectively bind to an antigen of interest and modulate immunological responses based upon the recognition of antigen.

As used herein, the term "immune checkpoints" means a group of molecules on the cell surface of CD4+ and CD8+ T cells. These molecules fine-tune immune responses by down-modulating or inhibiting an anti-tumor immune response and also induce or maintain tolerance, preventing autoimmunity, and reduce immune-mediated inflammation. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, and A2aR (see, for example, WO 2012/177624). Immunotherapeutic agents that can act as immune checkpoint inhibitors useful in the methods of the present invention, include, but are not limited to, Fc fusion proteins having effector function, such as certain classes of antibodies well-known in the art.

The term "anti-immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune disorders" refers to conditions characterized by an unwanted immune response. In some embodiments, the immune disorder is such that a desired anti-immune disorder response suppresses immune responses. Such conditions in which downregulation of an immune response is desired are well-known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, and a disorder requiring increased regulatory T cell production or function, as described further herein. In other embodiments, the immune disorder is such that a desired response is an increased immune response. Such conditions in which upregulation of an immune response is desired are well-known in the art and include, without limitation, disorders requiring increased CD4+ effector T cell production or function such as combating cancer, infections (e.g., parasitic, bacterial, helminthic, or viral infections), a disorder requiring improved vaccination efficiency, and the like).

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

The term "inhibit" includes the decrease, limitation, or blockage, of, for example a particular action, function, or interaction. In some embodiments, an immune disorder is "inhibited" if at least one symptom of the immune disorder is alleviated, terminated, slowed, or prevented. As used herein, an immune disorder is also "inhibited" if recurrence or spread of the immune disorder is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated antibody" is intended to refer to an antibody that is substantially free of other antibodies having different antigenic specificities (e.g., an antibody that specifically binds PD-1 polypeptide on Tregs based on dual specificity for PD-1 and a Treg cell surface protein marker purified away from antibodies that merely bind PD-1). Moreover, an isolated antibody may be substantially free of other cellular material and/or chemicals.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a therapeutic, probe, small molecule, and the like, for specifically detecting and/or therapeutically affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling immunological responses, cell growth, division, migration, survival, or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The "normal" level of expression of a biomarker is the level of expression of the biomarker in cells of a subject, e.g., a human patient, not afflicted with an immune disorder. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. Such "significance" levels can also be applied to any other measured parameter described herein, such as for expression, inhibition, cytotoxicity, cell growth, Tregs:Teffs ratio, and the like.

The term "peripheral blood cell subtypes" refers to cell types normally found in the peripheral blood including, but is not limited to, eosinophils, neutrophils, T cells, monocytes, NK cells, granulocytes, and B cells.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-PD-1 therapy, and/or evaluate the disease state. A pre-determined biomarker amount and/or activity measurement(s) may be determined in populations of patients with or without an immune disorder. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker for determining the likelihood of response of an immune disorder to anti-immune disorder therapy. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker cells or cell ratios (e.g., by cell sorting and/or counting), protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed immune disorder samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with an immune disorder; (3) its absolute or relatively modulated presence or absence in clinical subset of patients with an immune disorder (e.g., those responding to a particular anti-immune disorder therapy).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of an immune disorder or the likelihood of recovery from the disease. In some embodiments, the use of statistical algorithms provides a prognosis of the immune disorder in an individual. For example, the prognosis can be surgery, development of a clinical subtype of the immune disorder (e.g., GVHD subtype such as chronic GVHD), development of one or more clinical factors, or recovery from the disease.

The term "response to anti-immune disorder therapy" (e.g., Tregs having modulated PD-1 expression and/or activity alone or in combination with one or more other anti-immune disorder therapies) relates to any response of the immune disorder to an anti-immune disorder therapy. Anti-immune disorder response may be assessed according to well-known methods in the art, including those criteria described in the Examples. Response may be recorded in a quantitative fashion like percentage change or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of response may be done early after the onset of neoadjuvant or adjuvant therapy, e.g., after a few hours, days, weeks or preferably after a few months. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune disorder therapeutic regimen is at least 25%, 30%, 35%, 40%, 45%, 50%, 55%, 60%, 65%, 70%, 75%, 80%, 85%, or more. Additional criteria for evaluating the response to anti-immune disorder therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); disease free survival (wherein the term disease shall include immune disorders and diseases associated therewith). The length of said survival may be calculated by reference to a defined start point (e.g., time of diagnosis or start of treatment) and end point (e.g., death or recurrence). In addition, criteria for efficacy of treatment can be expanded to include probability of survival, probability of recurrence within a given time period, and the like. For example, in order to determine appropriate threshold values, a particular therapeutic regimen can be administered to a population of subjects and the outcome can be correlated to biomarker measurements that were determined prior to administration of any therapy. The outcome measurement may be pathologic response to therapy given in the neoadjuvant setting. Alternatively, outcome measures, such as overall survival and disease-free survival can be monitored over a period of time for subjects following therapy for whom biomarker measurement values are known. The period of time for which subjects are monitored can vary. For example, subjects may be monitored for at least 0.25, 0.5, 0.75, 1, 2, 3, 4, 5, 6, 7, 8, 9, 10, 12, 14, 16, 18, 20, 25, 30, 35, 40, 45, 50, 55, or 60 months. Biomarker measurement threshold values that correlate to outcome of an anti-immune disorder therapy can be determined using well-known methods in the art, such as those described in the Examples section. The terms can also refer to an improved prognosis, for example, as reflected by an increased time to recurrence, which is the period to first recurrence censoring for second independent immune disorders as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample. In some embodiments, any sample comprising T lymphocytes or subsets thereof are useful according to the present invention.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein). RNA interfering agents, e.g., siRNA molecules, may be administered to a subject having or at risk for having an immune disorder, to inhibit expression of a marker gene of the invention, e.g., a marker gene whose expression or source must be reduced in immune disorder (such as the markers listed in Table 1) and thereby treat, prevent, or inhibit a immune disorder in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific" refers to an exclusionary action or function. In one example, specific modulation of PD-1 in Tregs refers to the exclusive modulation of PD-1 expression and/or activity in Treg cell populations and not in other cell populations. In another example, specific binding of an antibody to a predetermined antigen refers to the ability of the antibody to bind to the antigen of interest without binding to other antigens. Typically, the antibody binds with an affinity ($K_D$) of approximately less than $1 \times 10^{-7}$M, such as approximately less than $10^{-8}$M, $10^{-9}$ M, $10^{-10}$ M, $10^{-11}$M, or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. In addition, $K_D$ is the inverse of $K_A$. The phrases "an antibody recognizing an antigen" and "an antibody specific for an antigen" are used interchangeably herein with the term "an antibody which binds specifically to an antigen."

By contrast, the term "selective" refers to a preferential action or function. For example, selective binding is a relative term referring to the ability of an antibody to preferentially discriminate the binding of one antigen over another. Bispecific or multispecific antibodies can selectively target certain antigens or cell populations based upon the increased binding affinities for multiple antigen targets expressed at a single location due to the increased local effective concentration of the multiple antigen targets. The term "selective" can be quantified in terms of the preferential effect in a particular target of interest relative to other targets. For example, a measured variable (e.g., PD-1 expression in Tregs versus PD-1 expression in non-Treg immune cell populations) can be 20%, 25%, 30%, 35%, 40%, 45%, 50%, 55%, 60%, 65%, 70%, 75%, 80%, 85%, 90%, 95%, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 70-fold, 80-fold, 90-fold, 100-fold, or greater or any range in between inclusive (e.g., 50% to 16-fold), different in a target of interest versus unintended or undesired targets. The same fold analysis can be used to confirm the magnitude of an effect in a given tissue, cell population, measured variable, measured effect, and the like, such as the Tregs:Teffs ratio, hyperproliferative cell growth rate or volume, Tregs proliferation rate, and the like.

The term "subject" refers to any healthy animal, mammal or human, or any animal, mammal or human afflicted with an immune disorder. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); disease free survival (wherein the term disease shall include immune disorders and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to therapy, probability of survival, probability of recurrence within a given time period, and the like.

The term "synergistic effect" refers to the combined effect of two or more anti-immune disorder agents or therapies that can be greater than the sum of the separate effects of each such agent or therapy alone. In some embodiments, it can provide for similar efficacy of monotherapy but with other unexpected improvements relative to monotherapy, such as reducing unwanted side effects.

The term "T cell" includes $CD4^+$ T cells and $CD8^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a therapy or substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter. For example, Foxp3, or other Treg-selective or Treg-specific promoter can be used to express a polynucleotide selective or specifically within Tregs.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" or "tolerance" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (e.g., a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

II. PD-1 and the PD-1/PD-L Axis

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well-known in the art and readily available on publicly available databases, such as the National Center for Biotechnology Information (NCBI). For example, exemplary nucleic acid and amino acid sequences derived from publicly available sequence databases are provided below.

For example, the term "PD-1" refers to a member of the immunoglobulin gene superfamily that functions as a coinhibitory receptor having PD-L1 and PD-L2 as known ligands. The "PD-1 axis" refers to immunological functions mediated by signaling based on the interaction of PD-1 with one or more of its ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). PD-1 is also induced on the surface of B cells (in response to anti-IgM). CTLA-4 can also be expressed on the surface of B cells. PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM 005018.2 and NP_005009.2 and is shown in Table 1 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well-known and include, for example, mouse PD-1 (NM_008798.2 and NP_032824.1), rat PD-1 (NM_001106927.1 and NP_001100397.1), monkey PD-1 (NM_001114358.1 and NP 001107830.1), dog PD-1

(XM_543338.4 and XP_543338.3), cow PD-1 (NM_001083506.1 and NP 001076975.1), and chicken PD-1 (XM_422723.3, XP_422723.2, XM_004943337.1, and XP 004943394.1). Exemplary nucleic acid and polypeptide sequences of PD-1 orthologs in organisms other than humans are also presented below in Table 1.

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA-4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000)1 Exp. Med. 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, B cells, macrophages, bone marrow-derived mast cells, Th2 cells, and airway epithelial (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L, also known as B7h) (Swallow et al. (1999) *Immunity* 11:423), B7-H3, B7-H4, VISTA, B7-H6, and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel 0 strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown of about 30 amino acids from 260 to about amino acid 290 of SEQ ID NO: 6. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP 001156884.1), and chicken PD-L1 (XM_424811.3 and XP_424811.3).

TABLE 1

```
SEQ ID NO: 1 Human PD-1 cDNA Sequence
cactctggtg gggctgctcc aggc atg cag atc cca cag gcg ccc tgg cca        51
               Met Gln Ile Pro Gln Ala Pro Trp Pro
                1               5 gtc gtc tgg gcg gtg cta caa ctg ggc tgg cgg cca gga tgg ttc tta       99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg      147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc      195
Leu Val Val Thr Glu Gly Asp Asn Ala Thr Phe Thr Cys Ser Phe Ser
             45                  50                  55 aac aca tcg gag agc ttc gtg cta aac tgg tac cgc atg agc ccc agc      243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc      291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac      339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac      387
Phe His Met Ser Val Val Arg Ala Arg Arg Asn Asp Ser Gly Thr Tyr
                110                 115                 120 ctc tgt ggg gcc atc tcc ctg gcc ccc aag gcg cag atc aaa gag agc      435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca      483
Leu Arg Ala Glu Leu Arg Val Thr Glu Arg Arg Ala Glu Val Pro Thr
        140                 145                 150 gcc cac ccc agc ccc tca ccc agg tca gcc ggc cag ttc caa acc ctg      531
Ala His Pro Ser Pro Ser Pro Arg Ser Ala Gly Gln Phe Gln Thr Leu
    155                 160                 165 gtg gtt ggt gtc gtg ggc ggc ctg ctg ggc agc ctg gtg ctg cta gtc      579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga      627
Trp Val Leu Ala Val Ile Cys Ser Arg Ala Ala Arg Gly Thr Ile Gly
                190                 195                 200 gcc agg cgc acc ggc cag ccc ctg aag gag gac ccc tca gcc gtg cct      675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag      723
Val Phe Ser Val Asp Tyr Gly Glu Leu Asp Phe Gln Trp Arg Glu Lys
        220                 225                 230 acc ccg gag ccc ccc gtg ccc tgt gtc cct gag cag acg gag tat gcc      771
Thr Pro Glu Pro Pro Val Pro Cys Val Pro Glu Gln Thr Glu Tyr Ala
    235                 240                 245 acc att gtc ttt cct agc gga atg ggc acc tca tcc ccc gcc cgc agg      819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat      867
Gly Ser Ala Asp Gly Pro Arg Ser Ala Gln Pro Leu Arg Pro Glu Asp
                270                 275                 280 gga cac tgc tct tgg ccc ctc tgaccggctt ccttggccac cagtgttctg cag     921
Gly His Cys Ser Trp Pro Leu
            285

SEQ ID NO: 2 Human PD-1 Amino Acid Sequence
Met Gln Ile Pro Gln Ala Pro Trp Pro Val Val Trp Ala Val Leu Gln
 1               5                  10                  15
```

TABLE 1 -continued

```
Leu Gly Trp Arg Pro Gly Trp Phe Leu Asp Ser Pro Asp Arg Pro Trp
         20                  25                  30

Asn Pro Pro Thr Phe Ser Pro Ala Leu Leu Val Val Thr Glu Gly Asp
             35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
         115                 120                 125

Ala Pro Lys Ala Gln Ile Lys Glu Ser Leu Arg Ala Glu Leu Arg Val
     130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                 165                 170                 175

Leu Leu Gly Ser Leu Val Leu Leu Val Trp Val Leu Ala Val Ile Cys
             180                 185                 190

Ser Arg Ala Ala Arg Gly Thr Ile Gly Ala Arg Arg Thr Gly Gln Pro
         195                 200                 205

Leu Lys Glu Asp Pro Ser Ala Val Pro Val Phe Ser Val Asp Tyr Gly
     210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                 245                 250                 255

Met Gly Thr Ser Ser Pro Ala Arg Arg Gly Ser Ala Asp Gly Pro Arg
             260                 265                 270

Ser Ala Gln Pro Leu Arg Pro Glu Asp Gly His Cys Ser Trp Pro Leu
         275                 280                 285
```

SEQ ID NO: 3 Human PD-L1S cDNA Acid Sequence

```
gcttcccgag gctccgcacc agccgcgctt ctgtccgcct gcagggcatt ccagaaag       58 atg agg ata ttt gct gtc ttt ata ttc atg acc tac tgg cat ttg ctg     106
Met Arg Ile Phe Ala Val Phe Ile Phe Met Thr Tyr Trp His Leu Leu
 1               5                  10                  15 aac gca ttt act gtc acg gtt ccc aag gac cta tat gtg gta gag tat     154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta     202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att     250
Asp Leu Ala Ala Leu Ile Val Tyr Trp Glu Met Glu Asp Lys Asn Ile
     50                  55                  60 att caa ttt gtg cat gga gag gaa gac ctg aag gtt cag cat agt agc     298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat     346
Tyr Arg Gln Arg Ala Arg Leu Leu Lys Asp Gln Leu Ser Leu Gly Asn
                 85                  90                  95
```

TABLE 1 -continued

| | | | | | | | | | | | | | | | |
|---|---|---|---|---|---|---|---|---|---|---|---|---|---|---|---|
| gct | gca | ctt | cag | atc | aca | gat | gtg | aaa | ttg | cag | gat | gca | ggg | gtg | tac | 394 |
| Ala | Ala | Leu | Gln | Ile | Thr | Asp | Val | Lys | Leu | Gln | Asp | Ala | Gly | Val | Tyr |
| | | | 100 | | | | | 105 | | | | | 110 | | | cgc tgc atg atc agc tat ggt ggt gcc gac tac aag cga att act gtg   442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg   490
Lys Val Asn Ala Pro Tyr Asn Lys Ile Asn Gln Arg Ile Leu Val Val
130                 135                 140 gat cca gtc acc tct gaa cat gaa ctg aca tgt cag gct gag ggc tac   538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt   586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat   634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac   682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg   730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca   778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt   833
Leu Ser Pro Ser Thr
            245 gaataaatga atgaatgaat aacactatgt ttacaaaata tatcctaatt cctcacctcc   893 attcatccaa accatattgt tacttaataa acattcagca gatatttatg gaataaaaaa   953 aaaaaaaaaa aaaaa                                                    968

SEQ ID NO: 4 Human PD-L1S Amino Acid Sequence
Met Arg Ile Phe Ala Val Phe Ile Phe Met Thr Tyr Trp His Leu Leu
 1               5                  10                      15

Asn Ala Phe Thr Val Thr Val Pro Lys Asp Leu Tyr Val Val Glu Tyr
            20                  25                      30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

TABLE 1 -continued

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
195             200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225             230                 235                 240

Leu Ser Pro Ser Thr
            245
```

SEQ ID NO: 5 Human PD-L1M cDNA Acid Sequence

```
cgaggctccg caccagccgc gcttctgtcc gcctgcaggg cattccagaa agatgagg        58
                                                          Met Arg
                                                                1 ata ttt gct gtc ttt ata ttc atg acc tac tgg cat ttg ctg aac gca       106
Ile Phe Ala Val Phe Ile Phe Met Thr Tyr Trp His Leu Leu Asn Ala
        5                   10                  15 ttt act gtc acg gtt ccc aag gac cta tat gtg gta gag tat ggt agc       154
Phe Thr Val Thr Val Pro Lys Asp Leu Tyr Val Val Glu Tyr Gly Ser
    20                  25                  30 aat atg aca att gaa tgc aaa ttc cca gta gaa aaa caa tta gac ctg       202
Asn Met Thr Ile Glu Cys Lys Phe Pro Val Glu Lys Gln Leu Asp Leu
35              40                  45                  50 gct gca cta att gtc tat tgg gaa atg gag gat aag aac att att caa       250
Ala Ala Leu Ile Val Tyr Trp Glu Met Glu Asp Lys Asn Ile Ile Gln
                55                  60                  65 ttt gtg cat gga gag gaa gac ctg aag gtt cag cat agt agc tac aga       298
Phe Val His Gly Glu Glu Asp Leu Lys Val Gln His Ser Ser Tyr Arg
            70                  75                  80 cag agg gcc cgg ctg ttg aag gac cag ctc tcc ctg gga aat gct gca       346
Gln Arg Ala Arg Leu Leu Lys Asp Gln Leu Ser Leu Gly Asn Ala Ala
        85                  90                  95 ctt cag atc aca gat gtg aaa ttg cag gat gca ggg gtg tac cgc tgc       394
Leu Gln Ile Thr Asp Val Lys Leu Gln Asp Ala Gly Val Tyr Arg Cys
    100                 105                 110 atg atc agc tat ggt ggt gcc gac tac aag cga att act gtg aaa gtc       442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca       490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag       538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag       586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc       634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act       682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc       730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta       778
Pro Glu Leu Pro Leu Ala His Pro Pro Asn Glu Arg Thr His Leu Val
            230                 235                 240
```

TABLE 1 -continued

```
att ctg gga gcc atc tta tta tgc ctt ggt gta gca ctg aca ttc atc    826
Ile Leu Gly Ala Ile Leu Leu Cys Leu Gly Val Ala Leu Thr Phe Ile
        245             250             255 ttc cgt tta aga aaa ggg aga atg atg gat gtg aaa aaa tgt ggc atc    874
Phe Arg Leu Arg Lys Gly Arg Met Met Asp Val Lys Lys Cys Gly Ile
260             265             270 caa gat aca aac tca aag aag caa agt gat aca cat ttg gag gag acg    922
Gln Asp Thr Asn Ser Lys Lys Gln Ser Asp Thr His Leu Glu Glu Thr
275             280             285             290 taatccagca ttgaacttc tgatcttcaa gcagggattc tcaacctgtg gtttaggggt    982
tcatcggggc tgagcgtgac aagaggaagg aatgggcccg tgggatgcag caatgtggg   1042
acttaaaagg cccaagcact gaaaatggaa cctggcgaaa gcagaggagg agaatgaaga  1102
aagatggagt caaacaggga gcctggaggg agaccttgat actttcaaat gcctgagggg  1162
ctcatcgacg cctgtgacag ggagaaagga tacttctgaa caaggagcct ccaagcaaat  1222
catccattgc tcatcctagg aagacgggtt gagaatccct aatttgaggg tcagttcctg  1282
cagaagtgcc ctttgcctcc actcaatgcc tcaatttgtt ttctgcatga ctgagagtct  1342
cagtgttgga acgggacagt atttatgtat gagttttttcc tatttatttt gagtctgtga  1402
ggtcttcttg tcatgtgagt gtggttgtga atgatttctt ttgaagatat attgtagtag  1462
atgttacaat tttgtcgcca aactaaactt gctgcttaat gatttgctca catctagtaa  1522
aacatggagt atttgtaaaa aaaaaaaaaa a                                 1553
```

SEQ ID NO: 6 Human PD-L1M Amino Acid Sequence

```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240
```

TABLE 1 -continued

```
     Leu Val Ile Leu Gly Ala Ile Leu Leu Cys Leu Gly Val Ala Leu Thr
                     245                 250                 255

Phe Ile Phe Arg Leu Arg Lys Gly Arg Met Met Asp Val Lys Lys Cys
                     260                 265                 270

Gly Ile Gln Asp Thr Asn Ser Lys Lys Gln Ser Asp Thr His Leu Glu
                     275                 280                 285

Glu Thr
         290

SEQ ID NO: 7 Mouse PD-L1 cDNA Sequence
   1    atgaggatat ttgctggcat tatattcaca gcctgctgtc acttgctacg ggcgtttact
  61    atcacggctc caaaggactt gtacgtggtg gagtatggca gcaacgtcac gatggagtgc
 121    agattccctg tagaacggga gctggacctg cttgcgttag tggtgtactg ggaaaaggaa
 181    gatgagcaag tgattcagtt tgtggcagga gaggaggacc ttaagcctca gcacagcaac
 241    ttcagggga gagcctcgct gccaaaggac cagcttttga agggaaatgc tgcccttcag
 301    atcacagacg tcaagctgca ggacgcaggc gtttactgct gcataatcag ctacggtggt
 361    gcggactaca gcgaatcac gctgaaagtc aatgccccat accgcaaaat caaccagaga
 421    atttccgtgg atccagccac ttctgagcat gaactaatat gtcaggccga gggttatcca
 481    gaagctgagg taatctggac aaacagtgac caccaacccg tgagtgggaa gagaagtgtc
 541    accacttccc ggacagaggg gatgcttctc aatgtgacca gcagtctgag ggtcaacgcc
 601    acagcgaatg atgttttcta ctgtacgttt tggagatcac agccagggca aaaccacaca
 661    gcggagctga tcatcccaga actgcctgca acacatcctc cacagaacag gactcactgg
 721    gtgcttctgg gatccatcct tgttgttcctc attgtagtgt ccacggtcct cctcttcttg
 781    agaaaacaag tgagaatgct agatgtggag aaatgtggcg ttgaagatac aagctcaaaa
 841    aaccgaaatg atacacaatt cgaggagacg taa SEQ ID NO: 8 Mouse PD-L1 Amino Acid Sequence
   1    mrifagiift acchllraft itapkdlyvv eygsnvtmec rfpvereldl lalvvyweke
  61    deqviqfvag eedlkpqhsn frgraslpkd qllkgnaalq itdvklqdag vycciisygg
 121    adykritlkv napyrkinqr isvdpatseh elicqaegyp eaeviwtnsd hqpvsgkrsv
 181    ttsrtegmll nvtsslrvna tandvfyctf wrsqpgqnht aeliipelpa thppqnrthw
 241    vllgsillfl ivvstvllfl rkqvrmldve kcgvedtssk nrndtqfeet SEQ ID NO: 9 Mouse PD-1 cDNA Sequence
   1    atgtgggtcc ggcaggtacc ctggtcattc acttgggctg tgctgcagtt gagctggcaa
  61    tcagggtggc ttctagaggt ccccaatggg ccctggaggt ccctcacctt ctacccagcc
 121    tggctcacag tgtcagaggg agcaaatgcc accttcacct gcagcttgtc caactggtcg
 181    gaggatctta tgctgaactg gaaccgcctg agtcccagca accagactga aaaacaggcc
 241    gccttctgta atggtttgag ccaacccgtc caggatgccc gcttccagat catacagctg
 301    cccaacaggc atgacttcca catgaacatc cttgacacac ggcgcaatga cagtggcatc
 361    tacctctgtg ggccatctc cctgcacccc aaggcaaaaa tcgaggagag ccctggagca
 421    gagctcgtgg taacagagag aatcctggag acctcaacaa gatatccccag ccctcgcccc
 481    aaaccagaag gccggtttca aggcatggtc attggtatca tgagtgccct agtgggtatc
 541    cctgtattgc tgctgctggc ctgggcccta gctgtcttct gctcaacaag tatgtcagag
 601    gccagaggag ctggaagcaa ggacgacact ctgaaggagg agccttcagc agcacctgtc
 661    cctagtgtgg ccctatgagga gctggacttc caggacgag agaagacacc agagctccct
 721    accgcctgtg tgcacacaga atatgccacc attgtcttca ctgaagggct gggtgcctcg
```

TABLE 1 -continued

```
781    gccatgggac gtaggggctc agctgatggc ctgcagggtc ctcggcctcc aagacatgag
841    gatggacatt gttcttggcc tctttga
```

SEQ ID NO: 10 Mouse PD-1 Amino Acid Sequence
```
  1    mwvrqvpwsf twavlqlswq sgwllevpng pwrsltfypa wltvsegana tftcslsnws
 61    edlmlnwnrl spsnqtekqa afcnglsqpv qdarfqiiql pnrhdfhmni ldtrrndsgi
121    ylcgaislhp kakieespga elvvterile tstrypspsp kpegrfqgmv igimsalvgi
181    pvllllawal avfcstsmse argagskddt lkeepsaapv psvayeeldf qgrektpelp
241    tacvhteyat ivfteglgas amgrrgsadg lqgprpprhe dghcswpl
```

SEQ ID NO: 11 Monkey PD-1 cDNA Sequence
```
  1    atgcagatcc cacaggcacc ctggccggtc gtctgggcgt tgctacaact gggctggcgg
 61    ccaggatggt tcttagaatc cccggacagg ccctggaacc cccccacctt ctcccccagcc
121    ctgctcctgg tgaccgaagg agacaacgcc accttcacct gcagcttctc aacgcctcg
181    gagagcttcg tgctgaactg gtaccgcatg agccccagca accagacgga caagctggct
241    gccttccccg aggaccgcag ccagcccggc cgggactgcc gcttccgcgt cacacaactg
301    cccaacgggc gcgacttcca catgagcgtg gtcagggccc ggcgcaacga cagcggcacc
361    tacctctgcg gggccatctc cctggccccc aaggcgcaga tcaaagagag cctgcgggca
421    gagctcaggg tgacagagag aagggcagaa gtgcccacag cccacccccag ccctcaccc
481    aggccagctg gccagttcca agccctggtg gttggtgtcg tgggcggcct gctgggcagc
541    ctggtgctgc tagtctgggt cctggctgtc atctgctccc gggctgcaca aggaccata
601    gaagccaggc gcaccggcca gcccctgaag gaggaccccct cggccgtgcc tgtgttctct
661    gtggactatg gggagctgga tttccagtgg cgagagaaga ccccggagcc cccggcaccc
721    tgtgtccctg agcagacgga gtacgccacc atcgtctttc ctagtgggct gggcacctcg
781    tccccggccc gcaggggctc agccgacggc cctcggagtc cccggccact gaggcctgag
841    gatggacact gctcttggcc cctctga
```

SEQ ID NO: 12 Monkey PD-1 Amino Acid Sequence
```
  1    mqipqapwpv vwavlqlgwr pgwflespdr pwnpptfspa lllvtegdna tftcsfsnas
 61    esfvlnwyrm spsnqtdkla afpedrsqpg rdcrfrvtql pngrdfhmsv vrarrndsgt
121    ylcgaislap kaqikeslra elrvterrae vptahpspsp rpagqfqalv vgvvggllgs
181    lvllvwvlav icsraaqgti earrtgqplk edpsavpvfs vdygeldfqw rektpeppap
241    cvpeqteyat ivfpsglgts sparrgsadg prsprplrpe dghcswpl
```

SEQ ID NO: 13 Rat PD-1 cDNA Sequence
```
  1    atgtgggtcc agcaggtacc ctggtcattc acttgggctg tgctacagtt gagctggcaa
 61    tcagggtggc ttctagaggt cctcaataag ccctggaggc cctcacctt ctccccaacc
121    tggctcacag tgtcagaggg agcaaatgcc accttcacct gcagtttctc aactggtcg
181    gaggatctta agctgaactg gtaccgtctg agtcccagca accagactga aaaacaggcc
241    gccttctgca atggttacag ccagcccgtc cgggatgccc gcttccagat cgtacaactg
301    cccaacggac atgacttcca catgaacatc ctcgatgcac ggcgcaatga cagtggcatc
361    tacctctgtg gggccatctc cctgcctccc aaggcacaaa tcaaagagag tcctggagca
421    gagcttgtgg taacagagag aatcctggag accccaacaa gatatcccag ccctcaccc
481    aagccagaag gccagtttca aggcttggtc attgtcatca tgagcgtcct agtgggtatc
541    cccgtgttgc tgctgctggc tgggctctc gctgccttct gctcaacagg tatgtcagag
601    gccagagaag ctggacgcaa ggaagaccct ccgaaggagg cgcatgcagc agccctgtt
```

```
661   cccagtgtgg cctacgagga gctggacttt cagggacgag agaagacacc agagcctgcc
721   ccctgtgtgc acacagaata cgccaccatt gtcttcactg aaggactgga tgcctcagcc
781   ataggacgta ggggctcagc tgatggccca cagggtcctc ggcctccaag acatgaggat
841   ggacactgct cttggcctct ttga
```

SEQ ID NO: 14 Rat PD-1 Amino Acid Sequence
```
  1   mwvqqvpwsf twavlqlswq sgwllevlnk pwrpltfspt wltvsegana tftcsfsnws
 61   edlklnwyrl spsnqtekqa afcngysqpv rdarfqivql pnghdfhmni ldarrndsgi
121   ylcgaislpp kagikespga elvvterile tptryprpsp kpegqfqglv ivimsvlvgi
181   pvlllllawal aafcstgmse areagrkedp pkeahaaapv psvayeeldf qgrektpepa
241   pcvhteyati vftegldasa igrrgsadgp qgprpprhed ghcswpl
```

SEQ ID NO: 15 Dog PD-1 cDNA Sequence
```
  1   atggggagcc ggcggggcc  ctggccgctc gtctgggccg tgctgcagct gggctggtgg
 61   ccaggatggc tcctagactc ccctgacagg ccctggagcc cgctcacctt ctccccggcg
121   cagctcacgg tgcaggaggg agagaacgcc acgttcacct gcagcctggc cgacatcccc
181   gacagcttcg tgctcaactg gtaccgcctg agcccccgca accagacgga caagctggcc
241   gccttccagg aggaccgcat cgagccgggc cgggacaggc gcttccgcgt catgcggctg
301   cccaacgggc gggacttcca catgagcatc gtcgctgcgc gcctcaacga cagcggcatc
361   tacctgtgcg gggccatcta cctgcccccc aacacacaga tcaacgagag tccccgcgca
421   gagctctccg tgacggagag aaccctggag ccccccacac agagccccag ccccccaccc
481   agactcagcg gccagttgca ggggctggtc atcggcgtca cgagcgtgct ggtgggtgtc
541   ctgctactgc tgctgctgac ctgggtcctg gccgctgtct tcccagggc  cacccgaggt
601   gcctgtgtgt gcgggagcga ggacgagcct ctgaaggagg ccccgatgc  agcgcccgtc
661   ttcacccgg actacgggga gctggacttc agtggcgag  agaagacgcc ggagcccccg
721   gcgccctgtg ccccggagca gaccgagtat gccaccatcg tcttcccggg caggccggcg
781   tccccgggcc gcagggcctc ggccagcagc ctgcaggag  cccagcctcc gagccccgag
841   gacggacccg gcctgtggcc cctctga
```

SEQ ID NO: 16 Dog PD-1 Amino Acid Sequence
```
  1   mgsrrgpwpl vwavlqlgww pgwlldspdr pwspltfspa qltvqegena tftcsladip
 61   dsfvlnwyrl sprnqtdkla afqedriepg rdrrfrvmrl pngrdfhmsi vaarindsgi
121   ylcgaiylpp ntqinespra elsvtertle pptqspsppp rlsgqlqglv igvtsvlvgv
181   lllllltwvl aavfpratrg acvcgsedep lkegpdaapv ftldygeldf qwrektpepp
241   apcapeqtey ativfpgrpa spgrrasass lqgaqppspe dgpglwpl
```

SEQ ID NO: 17 Cow PD-1 cDNA Sequence
```
  1   atggggaccc gcggcgct   gtggccactc gtctgggccg tgctgcagct gggctgctgg
 61   ccaggatggc tcctagagct ctcagcagg  ccctggagcg ccctcacctt ctctccccc
121   cggctggtcg tgcccgaggg agcgaatgcc accttcacct gcagcttctc cagtaagccg
181   gagcgcttcg tcctcaactg gtaccgcaag agccccagca accagatgga caaactggcc
241   gccttccctg aggaccgcag ccagcccagc cgagaccggc gcttccgcgt cacgccgctg
301   cccgatgggc agcagtttaa catgagcatc gtggcggccc agcgcaatga cagcggcgtc
361   tacttctgcg gggccatcta cctgccaccc cggacgcaga tcaacgagag ccacagcgca
421   gagctcatgg tgacagaggg ggtcctggag ccgccaacgg agccccccag ccccccagccc
481   aggcctgagg ccagatgca  gagcctggtc atcggcgtca caagcgtcct tctggggggtc
```

TABLE 1 -continued

```
541    ctgctgctgc cgccactgat ctgggtcctg gccgcggtct tcctcagggc cactcgaggg 601    ggctgcgccc gcaggagcca agaccagcct ccgaaggagg gctgccccctc tgtgccggct 661    gtcacagtgg actacgggga gctggacttc cagtggcggg agaagacccc ggagcccgcg 721    gctccctgcg tcccggagca gacagagtac gccaccatcg tcttcccagg ccgcagggcg 781    tccgccgaca gcccgcaggg gccctggcca ctgaggaccg aggatggaca ctgctcctgg 841    cccctctga SEQ ID NO: 18 Cow PD-1 Amino Acid Sequence
   1    mgtpralwpl vwavlqlgcw pgwlleassr pwsaltfspp rlvvpegana tftcsfsskp 61    erfvlnwyrk spsnqmdkla afpedrsqps rdrrfrvtpl pdgqqfnmsi vaaqrndsgv 121    yfcgaiylpp rtqineshsa elmvteavle ppteppspqp rpegqmqslv igvtsvllgv 181    lllppliwvl aavflratrg gcarrsqdqp pkegcpsvpa vtvdygeldf qwrektpepa 241    apcvpeqtey ativfpgrra sadspqgpwp lrtedghcsw pl
```

*Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.
*Included in Table 1 is PD-1, including any PD-1 cDNA or polypeptide.

III. Regulatory T Cells and Related Immune Cell Types

Regulatory T-cells (Tregs) are naturally occurring CD4+ CD25+FOXP3+ T lymphocytes that comprise ~5-10% of the circulating CD4+ T cell population, act to dominantly suppress autoreactive lymphocytes, and control innate and adaptive immune responses (Piccirillo and Shevach (2004) Semin. Immunol. 16:81-88; Fehervari and Sakaguchi (2004) Curr. Opin. Immunol. 16:203-208; Azuma et al. (2003) Cancer Res. 63:4516-4520; Cederbom et al. (2000) Eur. J Immunol. 30:1538-1543; Maloy et al. (2003) J. Exp. Med. 197:111-119; Serra et al. (2003) Immunity 19:877-889; Thornton and Shevach (1998)1 Exp. Med. 188:287-296; Janssens et al. (2003)1 Immunol. 171:4604-4612; Gasteiger et al. (2013) J Exp. Med. 210:1167-1178; Sitrin et al. (2013) J Exp. Med. 210:1153-1165; Schmitt and Williams (2013) Front. Immunol. 4:1-13). Natural Tregs also express low amounts of CD127, develop in the thymus, express GITR and CTLA-4. Induced Tregs are CD4+ T cells that acquire CD25 expression outside of the thymus in the periphery (e.g., mucosa-associated lymphoid tissue (MALT)), express low levels of CD45RB and do not natively express Foxp3 or CD25. Induced Tregs acquire Foxp3, CD25, CTLA-4, and GITR/AITR expression based on the influence of TGFbeta on CD4+ naïve conventional T cells in the periphery. Tregs achieve this suppression, at least in part, by inhibiting the proliferation, expansion, and effector activity of conventional T cells (Tcons). Tregs suppress effector T cells from destroying their (self-)target, either through cell-cell contact by inhibiting T cell help and activation, through release of immunosuppressive cytokines such as IL-10 or TGF-β, through production of cytotoxic molecules such as Granzyme B, through depleting IL-2 levels, or by changing nutrients in tissues. Depletion of Tregs was shown to enhance IL-2 induced anti-tumor immunity (Imai et al. (2007) Cancer Sci. 98:416-23).

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naïve T cells, activated T cells, memory T cells, resting Tcons, or Tcons that have differentiated toward, for example, the Thl or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. "Naïve Tcons" are CD4+ T cells that have differentiated in bone marrow, and successfully underwent a positive and negative processes of central selection in a thymus, but have not yet been activated by exposure to an antigen. Naïve Tcons are commonly characterized by surface expression of L-selectin (CD62L), absence of activation markers such as CD25, CD44 or CD69, and absence of memory markers such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) Philos. Trans. R. Soc. Lond. Biol. Sci. 356:625-637). In tumors, exhausted cells can present hallmarks of anergy.

Thus, increasing the number of Tregs, increasing Treg activity, and/or decreasing Treg cell death (e.g., apoptosis) is generally useful for suppressing unwanted immune reactions associated with a range of immune disorders (e.g., cGVHD). Tregs are also important in suppressing inflammation as well. In the context of ongoing inflammation, treatments can preferentially enhance Tregs without activating Tcons or other effectors that may worsen GVHD. Effective augmentation of Tregs in vivo is also directly relevant to other disorders of impaired peripheral tolerance (e.g., autoimmune diseases like SLE, T1D, MS, psoriasis, RA, IBD, vasculitis), where Treg dysfunction is increasingly implicated (Grinberg-Bleyer et al. (2010) *J. Exp. Med.* 207:1871-1878; Buckner (2010) *Nat. Rev. Immunol.* 10:849-859; Humrich et al. (2010) *Proc. Natl. Acad. Sci. U.S.A.* 107:204-209; Carbone et al. (2014) *Nat. Med.* 20:69-74).

Modulation of Treg activity, Teff activity, and Treg:Teff interactions can be determined according to well-known methods in the art and as exemplified in the Examples. For example, Tregs and/or Teffs proliferation, activity, apoptosis, cytokine production repertoire, Tregs activity, Tregs apoptosis, CD25 expression, phosphorylated STAT5 (pSTAT5) expression, FOXP3 expression, and the like can be analyzed. Moreover, phenotypic analyses of lymphocyte subsets, functional assays of immunomodulation leading to reduced immune responses, plasma cytokines, and the like can be analyzed as described further herein.

Such well-known immune cell characteristics can also be used to purify, enrich, and/or isolate Tregs. "Enriched Tregs" refer to a composition comprising Tregs in addition to other T cells in a proportion where the composition has at least a 1:2, 1:1.9, 1:1.8, 1:1.7, 1:1.6, 1:1.5, 1:1.4, 1:1.3, 1:1.2, 1:1.1, 1:1, 1:0.9, 1:0.8, 1:0.7, 1:0.6, 1:0.5, 1:0.4, 1:0.3, 1:0.2, 1:0.1, or more, or any range in between or any value in between, ratio of Tregs to Tcons/Teffs. Such ratios can be achieved by purifying a composition comprising T cells with various methodologies, such as CD8+ and CD19+ co-depletion in combination with positive selection for CD25+ cells. Such enriched Tregs can further be defined in terms of cell markers and/or viability. For example, an enriched Tregs cell composition can have greater than 40%, 45%, 50%, 55%, 60%, 65%, 70%, 75%, 80%, 85%, 90%, 95%, 99%, or more, or any range in between or any value in between, total cell viability. It can comprise greater than 40%, 45%, 50%, 55%, 60%, 65%, 70%, 75%, 80%, 85%, 90%, 95%, 99%, or more, or any range in between or any value in between, CD4+ CD25+ cells. It can comprise greater than 40%, 45%, 50%, 55%, 60%, 65%, 70%, 75%, 80%, 85%, 90%, 95%, 99%, or more, or any range in between or any value in between, FoxP3+ cells. Tregs can be administered in any suitable route as described herein, such as by infusion. Tregs can also be administered before, concurrently with, or after, other immunomodulatory agents.

In one embodiment, fluorescence activated cell sorting (FACS), also referred to as flow cytometry, is used to sort and analyze the different cell populations. Cells having a cellular marker or other specific marker of interest are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well-known in the art and described in, for example, U.S. Pat. Nos. 5,137,809; 5,750,397; 5,840,580; 6,465,249; Manz et al. (202) *Proc. Natl. Acad. Sci. U.S.A.* 99:11872-11877; and Akashi et al. (200) *Nature* 404:193-197. General guidance on fluorescence activated cell sorting is described in, for example, Shapiro (2003) *Practical Flow Cytometry,* 4th Ed., *Wiley-Liss* (2003) and Ormerod (2000) *Flow Cytometry: A Practical Approach,* 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) *Cytometry* 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

It is to be understood that the purification or isolation of cells also includes combinations of the methods described above. A typical combination may comprise an initial procedure that is effective in removing the bulk of unwanted cells and cellular material, for example leukopharesis. A second step may include isolation of cells expressing a marker common to one or more of the progenitor cell populations by immunoadsorption on antibodies bound to a substrate. An additional step providing higher resolution of different cell types, such as FACS sorting with antibodies to a set of specific cellular markers, may be used to obtain substantially pure populations of the desired cells.

The present invention also contemplates well-known methods for genetically modifying the genome of an organism or cell to modify the expression and/or activity of a biomarker of the present invention without contacting the organism or cell with agent once the genetic modification has been completed. For example, Tregs can be genetically modified using recombinant techniques in order to modulate the expression and/or activity of a biomarker, such as PD-1, such that no agent needs to contact the Tregs in order for the PD-1 expression and/or activity to be modulated. For example, targeted or untargeted gene knockout methods can be used, such as to recombinantly engineer subject Tregs ex vivo prior to infusion into the subject. For example, the target DNA in the genome can be manipulated by deletion, insertion, and/or mutation using retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis. Such methods generally use host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

Similarly, the CRISPR-Cas system can be used for precise editing of genomic nucleic acids (e.g., for creating null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326: 1509-1512; Moscou and Bogdanove (2009) *Science* 326: 1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

As described below and in some embodiments, Tregs and/or Teffs are administered to a subject. Thus, the Tregs and/or Teffs will have an immunocompatibility relationship to the subject host and any such relationship is contemplated for use according to the present invention. For example, the Tregs and/or Teffs can be syngeneic. The term "syngeneic" can refer to the state of deriving from, originating in, or being members of the same species that are genetically identical, particularly with respect to antigens or immunological reactions. These include identical twins having matching MHC types. Thus, a "syngeneic transplant" refers to transfer of cells from a donor to a recipient who is genetically identical to the donor or is sufficiently immunologically compatible as to allow for transplantation without an undesired adverse immunogenic response (e.g., such as one that would work against interpretation of immunological screen results described herein).

A syngeneic transplant can be "autologous" if the transferred cells are obtained from and transplanted to the same subject. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

A syngeneic transplant can be "matched allogeneic" if the transferred cells are obtained from and transplanted to different members of the same species yet have sufficiently matched major histocompatibility complex (MHC) antigens to avoid an adverse immunogenic response. Determining the degree of MHC mismatch may be accomplished according to standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 MHC antigens within the two or three HLA groups, respectively. In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Malden, Mass.). Other cell-based assays include flow cytometry using labeled antibodies or enzyme linked immunoassays (ELISA). Molecular methods for determining MHC type are well-known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

A syngeneic transplant can be "congenic" if the transferred cells and cells of the subject differ in defined loci, such as a single locus, typically by inbreeding. The term "congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

By contrast, "mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens, sufficient to elicit adverse immunogenic responses. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Similarly, in contrast, "xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

In addition, Tregs and/or Teffs can be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cells, stem cells, established cancer cell lines, immortalized primary cells, and the like. In certain embodiments, the immune systems of host subjects can be engineered or otherwise elected to be immunological compatible with transplanted cancer cells. For example, in one embodiment, the subject may be "humanized" in order to be compatible with human cancer cells. The term "immune-system humanized" refers to an animal, such as a mouse, comprising human HSC lineage cells and human acquired and innate immune cells, survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC—SCID, NSG (NOD-SCID IL2r-gamma(null) lack an innate immune system, B cells, T cells, and cytokine signaling), NOG (NOD-SCID IL2r-gamma (truncated)), BRG (BALB/c-Rag2(null)IL2r-gamma(null)), and H2dRG (Stock-H2d-Rag2(null)IL2r-gamma(null)) mice (see, for example, Shultz et al. (2007) *Nat. Rev. Immunol.* 7:118; Pearson et al. (2008) *Curr. Protocol. Immunol.* 15:21; Brehm et al. (2010) *Clin. Immunol.* 135:84-98; McCune et al. (1988) *Science* 241:1632-1639, U.S. Pat. No. 7,960,175, and U.S. Pat. Publ. 2006/0161996), as well as related null mutants of immune-related genes like Rag1 (lack B and T cells), Rag2 (lack B and T cells), TCR alpha (lack T cells), perforin (cD8+ T cells lack cytotoxic function), FoxP3 (lack functional CD4+ T regulatory cells), IL2rg, or Prf1, as well as mutants or knockouts of PD-1, PD-L1, Tim3, and/or 2B4, allow for efficient engraftment of human immune cells in and/or provide compartment-specific models of immunocompromised animals like mice (see, for example, PCT Publ. WO2013/062134). In addition, NSG-CD34+(NOD-SCID IL2r-gamma(null) CD34+) humanized mice are useful for studying human gene and tumor activity in animal models like mice.

As used herein, "obtained" from a biological material source means any conventional method of harvesting or partitioning a source of biological material from a donor. For example, biological material may obtained from a solid tumor, a blood sample, such as a peripheral or cord blood sample, or harvested from another body fluid, such as bone marrow or amniotic fluid. Methods for obtaining such samples are well-known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of cell lines or fluids, such as peripheral or cord blood, the samples may be withdrawn from a cryogenically or otherwise preserved bank of such cell lines or fluid. Such samples may be obtained from any suitable donor.

The obtained populations of cells may be used directly or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et al. (2004) *Bone Marrow Transplant.* 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well-known and described in the art (see, e.g., Broxmeyer et al. (2003) *Proc. Natl. Acad. Sci. U.S.A.* 100:645-650). Cells are preserved at a final temperature of less than about −135° C.

III. Agents Useful for Modulating PD-1 Expression and/or Activity in Tregs a. Agents

It is demonstrated herein that modulating PD-1 expression and/or activity selectively or specifically within the Treg subpopulation of immune cells surprisingly modulates function of Teffs and immune responses. Moreover, the use of a bispecific antibody to target PD-1 expression and/or activity selectively or specifically within the Teff subpopulation of immune cells is believed to more effectively increase effector activity than a general anti-PD-1 antibody because doing so would not lead to increased Treg numbers and/or function. Accordingly, the present invention provides compositions and methods for modulating PD-1 expression and/or activity selectively or specifically within the Treg subpopulation and/or Teff subpopulation of immune cells. For example, compositions useful in the methods of the present invention include antibodies, small molecules, peptides, peptidomimetics, natural ligands, and derivatives of natural ligands, that can either bind and/or inactivate or inhibit protein biomarkers of the invention, including the biomarkers listed in Table 1, or fragments thereof; RNA interference, antisense, nucleic acid aptamers, etc. that can downregulate the expression and/or activity of the biomarkers of the invention, including the biomarkers listed in Table 1, or fragments thereof; and nucleic acids and proteins, such as PD-1 protein or agonizing anti-PD-1 antibodies, that encode, express, or otherwise promote PD-1 to upregulate the expression and/or activity of the biomarkers of the present invention, including the biomarkers listed in Table 1.

For example, antibodies that specifically bind to PD-1 are well-known in the art. Representative examples include, without limitation, MDX-1106, Merck 3475, and CT-011. MDX-1106, also known as MDX-1106-04, ONO-4538 or BMS-936558, is a fully human IgG4 anti-PD-1 monoclonal antibody described in PCT Publ. No. WO 2006/121,168 and U.S. Pat. No. 8,0088,449. Merck 3475, also known as SCH-900475 and pembrolizumab, is a humanized IgG4 anti-PD-1 monoclonal antibody described in PCT Publ. No. WO 2009/114335; U.S. Pat. No. 8,354,509; and Hamid et al. (2013) *New Engl. J. Med.* 369:134-144. Pidilizumab (CT-011; CureTech) is a humanized IgG1 monoclonal antibody that binds to PD-1. Pidilizumab and other humanized anti-PD-1 monoclonal antibodies are disclosed in PCT Publ. No. WO 2009/101611. Similarly, AMP-224 (B7-DCIg; Amplimmune) is a PD-L2 Fc fusion soluble receptor that blocks the interaction between PD-1 and PD-L1 and is disclosed in PCT Publ. Nos. WO 2010/027827 and WO 2011/066342. Moreover, many other anti-PD-1 Fc fusion proteins are known in the art as described in U.S. Pat. No. 8,609,089; U.S. Pat. Publ. No. 2010/028330; U.S. Pat. Publ. No. 2012-0114649; and PCT Publ. No. WO 2014/089113.

In another embodiment, nucleic acid molecules encoding PD-1 (e.g., those in Table 1) are useful for modulating (e.g., increasing) the expression and/or activity of PD-1. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 or described herein can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

Similarly, a nucleic acid molecule of the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well-known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1, or portions thereof, from different species are also contemplated. For example, rat or monkey cDNA can be identified based on the nucleotide sequence of a human and/or mouse sequence and such sequences are well-known in the art. In one embodiment, the nucleic acid molecule(s) of the invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope of the invention. Moreover, nucleic acid molecules encoding one or more biomarkers listed in Table 1 from other species.

In addition to naturally-occurring allelic variants of the one or more biomarkers listed in Table 1 that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1. Similarly, another aspect of the present invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 1 may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well-known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding one or more biomarkers listed in Table 1. Other suitable probes for use in the diagnostic assays of the invention are described herein. Hybridization of an mRNA with the probe indicates that one or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the one or more biomarkers listed in Table 1.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854, 033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the one or more biomarkers listed in Table 1.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well-known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (MA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well-known in the art, or a fragment thereof. In another aspect, the present invention contemplates a composition comprising an isolated polypeptide corresponding to one or more biomarkers listed in Table 1 and less than about 25%, or alternatively 15%, or alternatively 5%, contaminating biological macromolecules or polypeptides.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 50, 55, 60, 65, 70, 75, 80, 85, 90, 95, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBBLAST programs of Altschul, et al. (1990)*J Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the)(BLAST program, score=50, word-length=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers described herein or, for example, listed in Table 1.

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate proteins that bind to said immunogen, using standard techniques. Such proteins can be Fc fusion proteins, such as polyclonal and monoclonal antibody, which can be prepared according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an Fc fusion protein such as an antibody specifically binds to PD-1 and also binds to one or more Fc receptors (FcRs). In another embodiment, such an Fc fusion protein further reduces or blocks the interaction between PD-1 and one or more PD-1 ligands, such as PD-L1 and/or PD-L2.

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980)1 *Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well-known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining the ability of the antibody to bind a desired target, such as PD-1, effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

The structural features of non-human or human antibodies (e.g., a rat anti-mouse/anti-human PD-1 antibody) can be used to create structurally related human antibodies that retain at least one functional property of the antibodies of the present invention, such as binding to PD-1. Another functional property includes inhibiting binding of the original known, non-human or human antibodies in a competition ELISA assay.

In some embodiments, monoclonal antibodies capable of specifically binding PD-1, optionally also inhibiting or reducing the interaction between PD-1 and one or more of its ligands, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available.

Similarly, monoclonal antibodies capable of specifically binding PD-1, optionally also inhibiting or reducing the interaction between PD-1 and one or more of its ligands, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

Monoclonal antibodies capable of specifically binding PD-1, optionally also inhibiting or reducing the interaction between PD-1 and one or more of its ligands, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The Fc fusion proteins, such as monoclonal antibodies, described herein can comprise a heavy chain, wherein the variable domain comprises at least a CDR having a sequence selected from the group consisting of the heavy chain variable domain CDRs presented herein or otherwise publicly available and a light chain, wherein the variable domain comprises at least a CDR having a sequence selected from the group consisting of the light chain variable domain CDRs presented herein or otherwise publicly available.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human Gal1 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth herein or otherwise publicly available and/or the light chain variable domain of the monoclonal antibodies of the present invention can comprise or consist of the vκ amino acid sequence set forth herein or otherwise publicly available.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments.

Other fragments of the monoclonal antibodies of the present invention are also contemplated. For example, individual immunoglobulin heavy and/or light chains are provided, wherein the variable domains thereof comprise at least a CDR presented herein or otherwise publicly available. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented herein or otherwise publicly available. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs presented herein or otherwise publicly available, are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided herein or otherwise publicly available.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be used in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies described herein, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

In addition to such general methods of modifying the structures of Fc fusion proteins described herein, methods are well-known in the art for increasing the affinity of Fc regions for Fc receptors in order to, for example, increase Fc-mediated effector functions, such as ADCC, ADCP, CDC, and the like (see, for example, Chan and Carter (2010) *Nat. Rev. Immunol.* 10:301-316; Cragg et al. (1999) *Curr. Opin. Immunol.* 11:541-547; Glennie et al. (2000) *Immunol. Today* 21:403-410).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An Fc fusion protein described herein can be conjugated to a radioisotope, e.g., radioactive iodine, to generate cytotoxic radiopharmaceuticals for destroying cells.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The Fc fusion conjugates described herein can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to Fc fusion proteins are well-known, see, e.g., Arnon et al., "Monoclonal Antibodies For Immunotargeting Of Drugs In Cancer Therapy", in *Monoclonal Antibodies And Cancer*

*Therapy*, Reisfeld et al. (eds.), pp. 243 56 (Alan R. Liss, Inc. 1985); Hellstrom et al., "Antibodies For Drug Delivery", in *Controlled Drug Delivery* (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", *Immunol. Rev.,* 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987)1 *Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988)1 Natl. Cancer Inst. 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, *Guide to Molecular Cloning Techniques* (1987), Academic Press, Inc., San Diego, Calif.; Merrifield, J. (1969) *J. Am. Chem. Soc.* 91:501; Chaiken I. M. (1981) *CRC Crit. Rev. Biochem.* 11:255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987)1 *Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2CH2, —CH=CH— (cis and trans), —COCH2, —CH(OH)CH2, and —CH2SO—, by methods known in the art and further described in the following references: Spatola, A. F. in "Chemistry and Biochemistry of Amino Acids, Peptides, and Proteins" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) Trends Pharm. Sci. pp. 463-468 (general review); Hudson, D. et al. (1979) Int. I Pept. Prot. Res. 14:177-185 (—CH2NH—, CH2CH2-); Spatola, A. F. et al. (1986) Life Sci. 38:1243-1249 (—CH2-S); Hann, M. M. (1982) J. Chem. Soc. Perkin Trans. I. 307-314 (—CH—CH—, cis and trans); Almquist, R. G. et al. (190) J. Med. Chem. 23:1392-1398 (—COCH2-); Jennings-White, C. et al. (1982) Tetrahedron Lett. 23:2533 (—COCH2-); Szelke, M. et al. European Appln. EP 45665 (1982) CA: 97:39405 (1982) (—CH(OH) CH2-); Holladay, M. W. et al. (1983) Tetrahedron Lett. (1983) 24:4401-4404 (—C(OH)CH2-); and Hruby, V. J. (1982) Life Sci. (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994)1 Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, fillingin of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

Particularly preferred Ig fusion proteins include the extracellular domain portion or variable region-like domain of PD-L1, TIM-3, LAG-3, or other biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge, CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21,20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *BioTechniques* 6:958-976; and Stein et al. (1988) *Cancer Res* 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372: 333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) *Proc. Natl. Acad. Sci. U.S.A.* 86:6553-6556; Lemaitre et al. (1987) *Proc. Natl. Acad. Sci. U.S.A.* 84:648-652; PCT Publication No. WO88/09810) or the blood-brain barrier (see, e.g., PCT Publication No. WO89/10134), hybridization-triggered cleavage agents. (See, e.g., Krol et al. (1988) *BioTech.* 6:958-976) or intercalating agents. (See, e.g., Zon (1988) *Pharm. Res.* 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N—2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An a-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) *RNA* 8:842; Xia et al. (2002) *Nature Biotechnology* 20:1006; and Brummelkamp et al. (2002) *Science* 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) *Science* 247:1222-1225 and U.S. Pat. No. 5,093,246). While ribozymes that cleave mRNA at site-specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in Tetrahymena *thermophila* (known as the IVS, or L-19 IVS RNA) and which has been extensively described by Thomas Cech and collaborators (Zaug et al. (1984) *Science* 224:574-578; Zaug et al. (1986) *Science* 231:470-475; Zaug et al. (1986) *Nature* 324:429-433; WO 88/04300; and Been et al. (1986) *Cell* 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in *Principles of Fluorescence Spectroscopy*, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the modulation of immune responses. Second active agents can be large molecules (e.g., proteins) or small molecules (e.g., synthetic inorganic, organometallic, or organic molecules). For example, anti-PD-L1 and anti-TIM-3 antibodies can be further combined with anti-LAG-3, anti-PD-L2, anti-CTLA4, etc. antibodies or combinations thereof.

Examples of large molecule active agents include, but are not limited to, hematopoietic growth factors, cytokines, and monoclonal and polyclonal antibodies. Typical large molecule active agents are biological molecules, such as naturally occurring or artificially made proteins.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.). Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Similarly, chemotherapeutic agents are well-known in the art. For example, chemotherapeutic agents include alkylating agents such as thiotepa and cyclophosphamide (Cytoxan™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide, and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiII); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; hestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa; taxoids, e.g., paclitaxel (Taxol™, Bristol Meyers Squibb Oncology, Princeton, N.J.) and docetaxel (Taxoteret™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™) raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprohde, and goserelin; and pharmaceutically acceptable salts, acids or derivatives of any of the above. In some embodiments, the inhibitor downregulates Racl output. Additional examples of chemotherapeutic and other anti-cancer agents are described in U.S. Pat. Publs. 2013/0239239 and 2009/0053224.

In still another embodiment, treatment methods may further use agents that block an activity of costimulatory pathways, such as that of other B lymphocyte antigen like B7-1, B7-2, or B7-3) to further downmodulate immune responses. Two separate agents that downmodulate immune responses can be combined as a single composition or administered separately (simultaneously or sequentially) to more effectively downregulate immune cell mediated immune responses in a subject. Furthermore, a therapeutically active amount of one or more of the subject agents, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Moreover, agents that promote the activity of immune checkpoint proteins are useful.

The term "immune checkpoint protein" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4 as described above, as well as PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, and A2aR (see, for example, WO 2012/177624). Agents useful for promoting immune checkpoint protein levels and activity are well-known in the art.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used.

In yet another embodiment, any first- or second-line immune disorder treatment can be combined with the methods of the present invention. Representative examples include, but are not limited to, steroidal, mycophenolate mofetil (MMF), and pentostatin (see, for example, Busca et al. (2000) *Bone Marrow Transplant* 25:1067-1071; Berger et al. (2007) *J. Pediatr. Hematol. Oncol.* 29:678-687; Jacobsohn et al. (2009) *Blood* 114:4354-4360).

b. Pharmaceutical Compositions

The therapeutic agents described herein including, e.g., blocking antibodies, peptides, fusion proteins, or small molecules, can be incorporated into pharmaceutical compositions suitable for administration to a subject. Such compositions typically comprise the antibody, peptide, fusion protein, small molecule, or the like, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered in the form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods for determining the results of the methods described herein, such as modulation of immune responses, metastasis, disease remission, disease relapse, tumor recurrence, death, autoimmunity, allergy (e.g., asthma, atopic dermatitis, allergic conjunctivitis, pollen allergy, food allergy, etc.), vaccination response, immune tolerance, immune exhaustion, immunological memory, immunological epitope responses, cytokine responses, relative representation of cells, genetic perturbations, and/or other immunologic effects are well-known in the art and as described herein. For example, determination of target nucleic acid sequences of interest can be performed using variety of sequencing methods known in the art. In preferred embodiments, a particular genetic perturbation is characterized by a measure of a nucleic acid or product thereof (e.g., mRNA). Marker expression may be monitored in a variety of ways, including by detecting mRNA levels, protein levels, or protein activity, any of which may be measured using standard techniques. Detection may involve quantification of the level of gene expression (e.g., genomic DNA, cDNA, mRNA, protein, or enzyme activity), or, alternatively, may be a qualitative assessment of the level of gene expression, in particular in comparison with a control level. The type of level being detected will be clear from the context. Various amplification and detection methods may also be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR), real time PCR, NASBA, Q-beta amplification, target-mediated amplification, ligase chain reaction, self-sustained sequence replication (SSR), transcription amplification, and the like. Many techniques are known in the state of the art for determining absolute and relative levels of gene expression, commonly used techniques suitable for use in the present invention include in situ hybridization, microarray, chip array, serial analysis of gene expression (SAGE), Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In certain embodiments, nucleic acid detection can be accomplished using methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan® reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al. (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligoligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa or MiSeq or HiSeq, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenom.* 1:95-100; and Shi (2001) *Clin. Chem.* 47:164-172) (see, for example, U.S. Pat. Publ. Nos. 2013/0274117, 2013/0137587, and 2011/0039304).

Similarly, polypeptides and/or cells of interest can be distinguished according to many well-known methods in the art including, but not limited to, flow cytometry, fluorescence activated cell sorting (FACS), fluorescence microscopy, detectable cell barcode technology (U.S. Pat. Publ. 2011/0263457), immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., "Basic and Clinical Immunology," Sites and Terr, eds., Appleton and Lange, Norwalk, Conn. Pp. 217-262, 1991, which is incorporated by reference). Preferred are binder-ligand immunoassay methods including reacting antibodies with an epitope or epitopes and competitively displacing a labeled polypeptide or derivative thereof.

V. Subjects

In one embodiment, the subject is a mammal (e.g., mouse, rat, primate, non-human mammal, and domestic animals, such as dog, cat, cow, and horse, etc.), and is preferably a human. Adult subjects, as well as pediatric subjects, are contemplated. Pediatric subjects can be treated as described herein, as well as using doses of therapeutic agents up to those used for adult subjects. In some embodiments, the subject is a mammal presenting an animal model of a disorder of interest, such as a mouse model of an autoimmune disorder.

In another embodiment of the methods of the present invention, the subject has not undergone treatment, such as anti-immune disorder therapy. In still another embodiment, the subject has undergone such treatment. In yet another embodiment, the subject is immunocompetent or immune-incompetent.

"Immunocompetent" subjects are those subjects comprising immune cells and immune function required to establish a normal or desired immune response following exposure to an antigen. The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In one embodiment, the immunocompetent subject is a wild type subject having a completely intact immune system. In another embodiment, the immunocompetent subject is a wild type subject having a completely intact, yet maturing, immune system (e.g., a juvenile subject). In still another embodiment, the immunocompetent subject has an intact immune system required for mediating immune responses using a specific arm of the immune system (e.g., acquired vs. innate and/or humoral vs. cytotoxic).

"Immuno-incompetent" subjects are those subjects lacking one or more immune cell types or lacking an immune function thereof to establish a normal or desired level of at least one immune response following exposure to an antigen. Immuno-incompetent subjects are more susceptible to opportunistic infections, for example viral, fungal, protozoan, or bacterial infections, prion diseases, and certain neoplasms. "Immunodeficient" subjects are subjects in which no native host immune response may be mounted, such as is the case with severe combined immunodeficiency (SCID) mice. "Immunocompromised" subjects have at least one substantially reduced immunological function relative to immunocompetent subjects. In either case, reduction in or absence of immunological function and/or cell types can arise from many different and well-known manners. For example, hematopoietic stem cells (HSCs) that give rise to all immune cells are any project thereof can be negatively affected in development, function, differentiation, survival, and the like.

Immuno-incompetent subjects can be generated in many different ways well-known in the art. They can result from modulating the function and/or number of various parameters in numerous combinations. For example, immune cell populations can be targeted for modulation that are resting, mitotic, terminally differentiated, post-mitotic, unactivated, activated, and the like, in order to effect a desired immune-incompetency. "Resting" cells refer to a non-cycling cell in a non-replicative state. Although resting cells may have the ability to replicate and divide upon activation, they are quiescent since they are non-cycling. Thus, "resting" cells are not simply manipulated immune cells that have been stimulated to divide and then engineered to revert to a quiescent, non-dividing phase. Resting cells can be "naïve," which means that they are immune cells that have differentiated in bone marrow, successfully undergone positive and negative selection in the thymus, and are mature, but have not been activated and are not memory cells. Naïve T cells are commonly characterized by the surface expression of L-selectin (CD62L); the absence of the activation markers, CD25, CD44, or CD69; and the absence of memory CD45RO isoform. They also express functional IL-7 receptors, consisting of subunits IL-7 receptor-α, CD127, and common-γ chain, CD132. In the naive state, T cells are thought to be quiescent and non-dividing, requiring the common-gamma chain cytokines IL-7 and IL-15 for homeostatic survival mechanisms. By contrast, activated T cells express or up-regulate expression of surface markers, CD25, CD44, CD62L$^{low}$, and CD69 and may further differentiate into memory T cells. Naïve B cells have not been exposed to antigen since they would either become a memory B cell or a plasma cell that secretes antibodies. In one embodiment, a resting cell becomes "activated" when it is triggered to enter into a state of reproduction or doubling and may include a cell entering the cell cycle, cell division, or mitosis. In another embodiment, a resting cell may also become "activated" when it encounters an external signal, such as an antigen or a cytokine, that initiates the activity of terminally differentiated, mature immunological cells to generate an immune response (e.g., T cell or B cell function).

In one embodiment, such subjects are obtained through defined or undefined genetic modifications. Representative, non-limiting examples of such genetic modifications are described above regarding immunocompromised animals. Moreover, the term "severe combined immune deficiency (SCID)" refers to a condition characterized by absence of T cells and lack of B cell function. Common forms of SCID caused by genetic modification include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+). In another example, genetically modified subjects that are immunodeficient have the severe combined immunodeficiency mutation, Prkdc$^{scid}$, commonly referred to as the scid mutation (see, for example, Bosma et al. (1989) *Immunogenet.* 29:54-56). Mice homozygous for the scid mutation are characterized by an absence of functional T cells and B cells, lymphopenia, hyperglobulinemia and a normal hematopoietic microenvironment. The scid mutation may be detected, for example, by detection of markers for the scid mutation using well-known methods.

In another embodiment, such subjects are obtained through non-genetic ablation of immune cell function or numbers. Other agents can be used to ablate immune cell function or numbers. For example, they may be conditioned with sub-lethal irradiation or lethal irradiation with high frequency electromagnetic radiation. The radiation can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or tele-therapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Similarly, non-genetic ablation of immune cell function or numbers can be effected through treatment with a radiomimetic drug such as busulfan or nitrogen mustard. Other immune cell cytoreductive drugs, include, among others, cyclophosphamide, ifosfamide, etoposide, cytosine arabinoside, carboplatin, and other chemotherapeutic agents (Montillo et al. (2004) *Leukemia* 18:57-62; Dasgupta et al. (1996) *J. Infusional Chemother.* 6:12; and Wright et al. (2001) *Blood* 97:2278-2285). Other classes of cytoreductive drugs include, but are not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of beta-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z. Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) *Genes Dev* 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921).

Non-genetic ablation of immune cell function or numbers can be effected through treatment with agents, such as antibodies, to deplete immune system-mediating cell populations, or treatment with agents that preferentially deplete immune system-mediating cell populations (see, for example, Hayakawa et al. (2009) *Stem Cells* 27:175-182). For example, anti-CD4 and anti-CD8 antibodies can be used to neutralize and/or deplete CD4+ T cells and CD8+ T cells, respectively. Similarly, anti-CD3 antibodies can be used to deplete all T cells, anti-B220 and/or anti-CD19 antibodies can be used to deplete all B cells, anti-CD11b antibodies can be used to deplete macrophages, anti-Ly-6G (Gr-1) antibodies can be used to deplete monocytes and granulocytes, and anti-NK1.1 antibodies can be used to deplete Natural Killer (NK) cells.

Assays for confirming immune-incompetence of one or more immune cell types or functions are also well-known in the art. Determining the differentiation potential of cells, and thus the presence or absence of immune cell populations, is typically conducted by exposing the cells to conditions that permit development into various terminally differentiated cells. These conditions generally comprise a mixture of cytokines and growth factors in a culture medium permissive for development of the myeloid or lymphoid lineage. Colony forming culture assays rely on culturing the cells in vitro via limiting dilution and assessing the types of cells that arise from their continued development. A common assay of this type is based on methylcellulose medium supplemented with cytokines (e.g., MethoCult, Stem Cell Technologies, Vancouver, Canada and Kennedy et al. (1997) *Nature* 386:488-493). Cytokine and growth factor formulations permissive for differentiation in the hematopoietic pathway are described in Manz et al. (2002) *Proc. Natl. Acad. Sci. U.S.A.* 99:11872-11877; U.S. Pat. No. 6,465,249; and Akashi et al., Nature 404:193-197). Cytokines include SCF, FLT-3 ligand, GM-CSF, IL-3, TPO, and EPO. Another in vitro assay is long-term culture initiating cell (LTC-IC) assay, which typically uses stromal cells to support hematopoiesis (see, e.g., Ploemache et al. (1989) *Blood* 74:2755-2763 and Sutherland et al. (1995) *Proc. Natl. Acad. Sci.* U.S.A. 87:3745).

Another type of assay suitable for determining the immune-incompetence state of a subject relies upon in vivo administration of cells into a host animal and assessment of the repopulation of the hematopoietic system. The recipient is immunocompromised or immunodeficient to limit rejection and permits acceptance of allogeneic or xenogeneic cell transplants. A useful animal system of this kind is the NOD/SCID (Pflumio et al. (1996) *Blood* 88:3731; Szilvassym et al. (2002) "Hematopoietic Stem Cell Protocol" in *Methods in Molecular Medicine*, Humana Press; Greiner et al. (1998) *Stem Cells* 16:166-177; Piacibello et al. (1999) *Blood* 93:3736-3749) or Rag2 deficient mouse (Shinkai et al. (1992) *Cell* 68:855-867). Cells originating from the infused cells are assessed by recovering cells from the bone marrow, spleen, or blood of the host animal and determining presence of cells displaying specific cellular markers (i.e., marker phenotyping), typically by FACS analysis. Detection of markers specific to the transplanted cells permits distinguishing between endogenous and transplanted cells. For example, antibodies specific to human forms of the cell markers (e.g., HLA antigens) identify human cells when they are transplanted into suitable immunodeficient mouse.

The methods of the present invention can be used to treat and/or determine the responsiveness to anti-immune disorder therapy of many different immune disorders in which modulating (e.g., suppressing or otherwise downregulating immune responses) is desired. The functions of activated immune cells can be inhibited by down-regulating immune cell responses, by inducing specific anergy in immune cells, or both.

For example, the methods of the present invention can be used to induce tolerance against specific antigens by co-administering an antigen with the therapeutic compositions of such methods. Tolerance can be induced to specific proteins. In one embodiment, immune responses to allergens (e.g., food allergens), or to foreign proteins to which an immune response is undesirable, can be inhibited. For example, patients that receive Factor VIII frequently generate antibodies against this clotting factor. Co-administration of recombinant factor VIII (or by physically linked to Factor VIII, e.g., by cross-linking) in the methods of the present invention can result in downmodulation of immune responses. In similar manners, increased clonal deletion and/or increased exhaustion (e.g., T cell exhaustion) can be induced.

Downregulating immune responses is useful for treating a number of other "immune disorders" according to the present invention including, without limitation, situations of tissue, skin and other solid organ transplantation (e.g., kidney, liver, heart, and vascularized composite allotransplantation transplants), in hematopoietic stem cell transplantation rejection (e.g., graft-versus-host disease (GVHD)), in autoimmune diseases such as systemic lupus erythematosus, multiple sclerosis, allergy, a transplant, hypersensitivity response, in a disorder requiring increased CD4+ T cell production or function, in a disorder requiring improved vaccination efficiency, and in a disorder requiring increased regulatory T cell production or function. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation can promote the generation of an inhibitory signal. Moreover, inhibition may also be sufficient to anergize the immune cells, thereby inducing tolerance in a subject. Induction of long-term tolerance avoids the necessity of repeated administration of these blocking reagents.

Downmodulation of immune responses are also useful in treating autoimmune disease, such as type 1 diabetes (T1D) and multiple sclerosis. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, the methods of the present invention can induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is also useful therapeutically in the treatment of allergy and allergic reactions, e.g., by inhibiting IgE production. Allergic reactions can be systemic or local in nature, depending on the route of entry of the allergen and the pattern of deposition of IgE on mast cells or basophils. Thus, inhibition of immune cell mediated allergic responses (e.g., to food) locally or systemically according to the methods of the present invention. In one embodiment, the allergy is allergic asthma.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response according to the methods of the present invention may also be useful in treating an autoimmune attack of autologous tissues. It is therefore within the scope of the invention to modulate conditions exacerbated by autoimmune attack, such as autoimmune disorders, as well as conditions such as heart disease, myocardial infarction, and atherosclerosis.

In a preferred embodiment, the immune disorder is graft-versus-host-disease (e.g., chronic GVHD). For many patients with hematologic malignancies, allogeneic hematopoietic stem cell transplant (HSCT) offers the only opportunity for cure. Unfortunately, significant obstacles remain, most notably disease recurrence and GVHD. Over 40% of patients undergoing HSCT relapse while more than 50% will develop cGVHD, a debilitating condition with multi-system immune manifestations associated with a considerable morbidity and mortality (Kahl et al. (2007) *Blood* 110:2744-2748; Perez-Simon et al. (2008) *Biol. Blood Marrow Transplant.* 14:1163-1171). Although the incidence in the pediatric population is lower, cGVHD remains a leading cause of non-relapse morbidity and mortality following allogeneic HSCT for malignant disease, occurring in 20 to 50% of children surviving greater than 100 days post-HSCT (Baird et al. (2010) *Pediatr. Clin. North Am.* 57:297-322). Donor cell-mediated immune responses are responsible for GVL and GVHD reactions. Inadequate recognition and destruction of residual tumor cells by a newly engrafted donor immune system permits recurrence of a patient's malignancy, while uncontrolled reactions against host antigens lead to GVHD (Antin (1993) *Blood* 82:2273-2277; Ferrara et al. (2009) *Lancet* 373:1550-1561). Chronic GVHD pathogenesis involves inflammatory T- and B-cell responses to allogeneic (donor/recipient polymorphic) and autologous (donor/recipient non-polymorphic) antigens and it remains a common problem and major therapeutic challenge after allogeneic HSCT, and long-term survivors often experience impaired quality of life and increased late mortality (Subramaniam et al. (2007) *Leukemia* 21:853-859). The increasing use of mobilized peripheral blood progenitor cells rather than bone marrow as a source of stem cells for HCT has resulted in a clear increase in the incidence of cGVHD (Cutler et al. (2001)1 *Clin. Oncol.* 19:3685-3691; Lee et al. (2007) *Blood* 110:4576-4583). The incidence of cGVHD in pediatric patients is expected to rise as allogeneic HSCT is increasingly being performed for non-malignant indications such as sickle cell anemia, immunodeficiency and congenital metabolic diseases. In both adults and children, the inflammatory or fibrotic changes associated with cGVHD most commonly involve the skin, eyes, mouth, liver and respiratory tract. PD-1 expression and/or inhibition can be downregulated in advance of any adoptive cell therapy, such as stem cell therapy, organ transplantation, and the like. As described above, selectively increasing Treg numbers and/or potency is useful downregulating immune responses.

By contrast, the present invention also provides methods for increasing immune responses, such as enhancing effector functions of Teffs by upregulating PD-1 in Tregs. Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as encephalitis might be alleviated by systemic administration of such agents. As described below, respiratory infections, such as influenza and the common cold, can be treated by respiration-based administration, such as intranasal, pulmonary inhalation, lung deposition, and related routes well-known in the art. In one preferred embodiment, agents that upregulate the immune response described herein are useful for modulating the arginase/iNOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for upregulating immune responses can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell. The preparation of immunotoxins is, in general, well known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, a-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

In another embodiment, certain combinations work synergistically in the treatment of conditions that would benefit from the modulation of immune responses. Second active agents can be large molecules (e.g., proteins) or small molecules (e.g., synthetic inorganic, organometallic, or organic molecules). For example, immune checkpoint inhibitors can be further combined with other agents or therapies useful in treating a condition of interest.

Moreover, certain immunotherapies can be used to promote immune responses. Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX-40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well known in the art.

In still another embodiment, the term "targeted therapy" refers to administration of agents that selectively interact with a chosen biomolecule to thereby treat cancer. For example, bevacizumab (Avastin®) is a humanized monoclonal antibody that targets vascular endothelial growth factor (see, for example, U.S. Pat. Publ. 2013/0121999, WO 2013/083499, and Presta et al. (1997) *Cancer Res.* 57:4593-4599) to inhibit angiogenesis accompanying tumor growth. In some cases, targeted therapy can be a form of immunotherapy depending on whether the target regulates immunomodulatory function.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

VI. Methods of Modulating Immune Responses by Modulating PD-1 Expression and/or Activity in Tregs and/or Teffs The present invention also provides prophylactic methods for preventing an immune disorder in a subject by modulating PD-1 expression and/or activity selectively or specifically within Tregs and/or Teffs. Subjects at risk for an unwanted immune disorder can be identified, for example, by any or a combination of diagnostic or prognostic assays known in the art. Administration of a prophylactic agent(s)

can occur prior to the manifestation of symptoms associated with an undesired immune response. The appropriate agent(s) used for treatment (e.g. antibodies, peptides, fusion proteins, or small molecules) can be determined based on clinical indications and can be identified using diagnostic assays well-known in the art, as well as those described herein.

The present invention provides therapeutic methods of modulating an immune response, e.g., by modulating PD-1 expression and/or activity selectively or specifically within Tregs and/or Teffs. In one embodiment, a method for modulating effector function of effector T cells (Teffs) by regulatory T cells (Tregs), comprising a) selectively modulating the expression and/or activity of PD-1 in Tregs; and b) contacting the Tregs with Teffs, thereby modulating effector function of the Teffs by the Tregs, is provided. The expression and/or activity of one or more biomarkers described herein (e.g., Treg proliferation, Treg numbers, Treg activity, Treg apoptosis, Tregs:Tcons ratio, biomarkers listed in Table 1 and the Examples or fragments thereof, and the like) for therapeutic purposes are provided. The biomarkers of the present invention when modulated in Tregs have been demonstrated to correlate with treatment of immune disorders. Accordingly, the activity and/or expression of the biomarkers in Tregs, as well as the interaction between one or more biomarkers or a fragment thereof on Tregs and its natural binding partner(s) or a fragment(s) thereof, can be modulated in order to treat immune disorders.

Similarly, in another embodiment, a method of increasing the effector function of effector T cells (Teffs) comprising contacting Teffs with a bispecific antibody selective for both PD-1 and a Teff cell surface protein, thereby increasing the effector function of the Teffs, is provided. It has been determined herein that when PD-1 is lost on cells whose primary function is to suppress immune responses, such as in Tregs, the consequence is a stronger suppressor cell. Accordingly, selectively or specifically targeting Teffs to inhibit or block PD-1 expression and/or activity therein, such as by using a bispecific antibody selective for both PD-1 and a Teff cell surface protein, increases the effector function of the Teffs by bypassing the suppression of PD-1 inhibition or blockade on Tregs.

In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening methods

However, the present invention is not restricted to in vivo treatment in a subject. Tregs and/or Teffs can be isolated from a subject for ex vivo procedures (e.g., immune cell processing out side of the body and re-administration of the cells back into the body). Similarly, Tregs and/or Teffs can be cultured in vitro. Expression and/or activity of biomarkers of the present invention, such as PD-1, can be selectively modulated in Tregs and/or Teffs in vitro, ex vivo, or in vivo and the resulting effects on cellular processes (e.g., cell proliferation, differentiation, death, etc.) or immune responses (e.g., cytotoxicity, cytokine production, etc.) can be analyzed in vitro, ex vivo, or in vivo. In this manner, PD-1 deficient Tregs, for example, can be used in vitro to assay Treg biology either alone or in combination with Teffs or other cell types and/or manipulations. Moreover, such manipulations can be performed in combination. For example, Tregs can be isolated from a subject, subjected to recombinant genetic manipulation to specifically inactivate PD-1, re-administered to a subject, and then provided with systemic administration of a selective anti-PD-1 blocking agent, such as an anti-PD-1/CD25 bispecific antibody or anti-PD-1 siRNA, in vivo. Similar manipulations can be performed using Teffs instead of Tregs.

In one embodiment, a method for identifying an agent which modulates an immune response entails determining the ability of the candidate agent to promote or inhibit the physical and/or functional interaction of Tregs modified as described herein with other cell types (e.g., Teffs, cell-based vaccines, etc.) and/or immunomodulators.

The assays are cell-based assays and may comprise, for example, contacting Tregs and/or Teffs modified as described herein with a test agent and determining the ability of the test agent to modulate (e.g. stimulate or inhibit) the physical and/or functional interaction between immune-related cells of interest. Determining the ability of the polypeptides to bind to, or interact with, each other may be accomplished, e.g., by measuring direct binding or by measuring a parameter of immune cell response.

For example, in a direct binding assay, polypeptides may be coupled with a radioisotope or enzymatic label such that binding of immune-related biomolecules may be determined by detecting the labeled protein in a complex. For example, the polypeptides may be labeled with $^{125}$I, $^{35}$S, $^{14}$C, or $^{3}$H, either directly or indirectly, and the radioisotope detected by direct counting of radioemission or by scintillation counting. Alternatively, the polypeptides may be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between immune-related biomolecules or cells of interest without the labeling of any of the interactants. For example, a microphysiometer may be used to detect the interaction of immune-related biomolecule polypeptides without the labeling of either polypeptide (McConnell et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate may be used as an indicator of the interaction between compound and receptor.

In a preferred embodiment, determining the ability of the test agents (e.g. nucleic acids, polypeptides, antibodies, fusion proteins, peptides, or small molecules) to antagonize or agonize the physical and/or functional interaction between a given set of immune-related biomolecules or cells may be accomplished by determining the activity of one or more members of a set of immune-related biomolecule polypeptides. For example, the activity of polypeptides may be determined by detecting induction of a cellular second messenger (e.g., PD-1 downstream signaling activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the polypeptides, such as various autoimmune, allergic (e.g., asthma, atopic dermatitis, allergic conjunctivitis, pollen allergy, food allergy, etc.), vaccination, immunotolerance, cancer immunotherapy, immune exhaustion, immunological memory, or immunological epitope responses. Determining the ability of the test agent to bind to or interact with said polypeptide may be accomplished, for example, by measuring the ability of a compound to modulate immune cell costimulation or inhibition in a proliferation assay, or by interfering with the ability of said polypeptide to bind to antibodies that recognize a portion thereof.

Test agents that modulate immune responses may be identified by their ability to modulate immune cell proliferation, and/or effector function, or to modulate anergy, clonal deletion, and/or exhaustion when added to an assay. For example, cells may be cultured in the presence of an agent that stimulates signal transduction via an activating receptor. A number of recognized readouts of cell activation may be employed to measure cell proliferation or effector function (e.g., antibody production, cytokine production, phagocytosis) in the presence of the activating agent. The ability of a test agent to block this activation may be readily determined by measuring the ability of the agent to effect a decrease in proliferation or effector function being measured, using techniques known in the art.

For example, agents of the present invention may be tested for the ability to inhibit or enhance co-stimulation and/or co-inhibition in a T cell assay, such as described in Freeman et al. (2000)1 Exp. Med. 192:1027 and Latchman et al. (2001) Nat. Immunol. 2:261. Immune cells of interest may be activated, such as with anti-CD3 antibody, and presented with Tregs modified as described herein. Proliferation of T cells may be measured by $^3$H thymidine incorporation. An assay may be performed with or without CD28 costimulation in the assay.

Alternatively, agents of the present invention may be tested for the ability to modulate cellular production of cytokines which are produced by or whose production is enhanced or inhibited in immune cells in response to immune response modulation. For example, immune cells of interest may be suboptimally stimulated in vitro with a primary activation signal. For example, T cells may be stimulated with phorbol ester, anti-CD3 antibody or preferably antigen in association with an MHC class II molecule, and given a costimulatory signal, e.g., by a stimulatory form of B7 family antigen, for instance by a cell transfected with nucleic acid encoding a B7 polypeptide and expressing the peptide on its surface or by a soluble, stimulatory form of the peptide. Known cytokines released into the media may be identified by ELISA or by the ability of an antibody which blocks the cytokine to inhibit immune cell proliferation or proliferation of other cell types that is induced by the cytokine. For example, an IL-4 ELISA kit is available from Genzyme (Cambridge Mass.), as is an IL-7 blocking antibody. The effects of Tregs modified as described herein and added to the assay can be assessed. The effect of stimulating or blocking the interaction of immune-related biomolecules on the cytokine profile may then be determined.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, may be accomplished in any vessel suitable for containing the reactants. Examples of such vessels include microtiter plates, test tubes, and microcentrifuge tubes. In one embodiment, a fusion protein may be provided which adds a domain that allows one or both of the proteins to be bound to a matrix. For example, glutathione-S-transferase/immune-related polypeptide fusion proteins, or glutathione-S-transferase/target fusion proteins, may be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes may be dissociated from the matrix, and the level of polypeptide binding or activity determined using standard techniques.

In an alternative embodiment, determining the ability of the test compound to modulate the activity of an immune-related polypeptide of interest may be accomplished as described above for cell-based assays, such as by determining the ability of the test compound to modulate the activity of a polypeptide that functions downstream of the polypeptide. For example, levels of second messengers may be determined, the activity of the interactor polypeptide on an appropriate target may be determined, or the binding of the interactor to an appropriate target may be determined as previously described.

In some embodiments, determination as to modulation of an immune-related indication of interest may be made in comparison to a control, which term is described above, and determination of an overexpression, overactivity, underexpression, underactivity, etc, which terms are also described above.

b. Therapeutic methods

Modulatory methods of the invention, as described above, involve contacting a Treg with or causing a Tregs to modulate the expression and/or activity of one or more biomarkers of the invention, including one or more biomarkers listed in Table 1 and the Examples or a fragment thereof. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for immune disorders well-known to the skilled artisan), either consecutively with, pre- or post-conventional therapy. For example, these modulatory agents can be administered with a therapeutically effective dose of an immunosuppressive agent or therapy.

In another embodiment, the immune response can be downregulated by the methods described herein, in order to maintain preexisting tolerance, clonal deletion, and/or exhaustion (e.g., T cell exhaustion). For example, immune responses against antigens to which a subject cannot mount a significant immune response, e.g., to an autologous antigen, can be maintained.

In one embodiment, immune cells are obtained from a subject and cultured ex vivo in the presence of an agent as described herein, to modify Tregs and/or remove or further remove a population of immune cells that modulate (e.g., inhibit or enhance) immune cell activation. In a further embodiment the filtered immune cells are then administered to a subject. Since immune cells can be stimulated in vitro by, for example, providing to the immune cells a primary activation signal and a costimulatory signal, various agents can also be used to reduce the costimulation and proliferation of effector immune cells and/or promote inhibitory regulatory immune cells. In one embodiment immune cells are cultured ex vivo according to the method described in PCT Application No. WO 94/29436. The costimulatory polypeptide can be soluble, attached to a cell membrane, or attached to a solid surface, such as a bead. Similarly, agents useful for promoting immune cell depletion can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell. The preparation of immunotoxins is, in general, well-known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, a-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

In yet another embodiment, the efficacy of the treatment methods described herein can be enhanced by incorporating a step of lymphodepletion prior to, concurrently with, or after the administration of agents described herein. For example, therapeutic benefits of administering the described agents can be synergistically enhanced by performing such administration after or in conjunction with lymphodepletion. Methods for achieving lymphodepletion in various forms and at various levels are well-known in the art (see, for example, U.S. Pat. No. 7,138,144). For example, the term "transient lymphodepletion" refers to destruction of lymphocytes and T cells, usually prior to immunotherapy. This can be accomplished in a number of ways, including "sublethal irradiation," which refers to administration of one or more doses of radiation that is generally non-lethal to all members of a population of subjects to which the administration is applied. Transient lymphodepletion is generally not myeloablative, as would be the case in complete lymphodepletion, such that the subjects hematopoietic or immunological capacity remains sufficiently intact to regenerate the destroyed lymphocyte and T cell populations. By contrast, "lethal irradiation" occurs when the administration is generally lethal to some but not all members of the population of subjects and "supralethal irradiation" occurs when the administration is generally lethal to all members of the population of subjects.

Depending on the application and purpose, transient lymphodepletion or complete lymphodepletion may be effected, for example, by any combination of irradiation, treatment with a myeloablative agent, and/or treatment with an immunosuppressive agent, according to standard protocols. For example, biological methods include administration of immunity-suppressing cells or by administration of biological molecules capable of inhibiting immunoreactivity, such as, for example, Fas-ligand and CTLA4-Ig. Examples of myeloablative agents include busulfan, dimethyl mileran, melphalan and thiotepa. Examples of immunosuppressive agents include prednisone, methyl prednisolone, azathioprine, cyclosporine A, cyclophosphamide, fludarabin, CTLA4-Ig, anti-T cell antibodies, etc.

Regarding irradiation, a sublethal dose of irradiation is generally within the range of 1 to 7.5 Gy whole body irradiation, a lethal dose is generally within the range of 7.5 to 9.5 Gy whole body irradiation, and a supralethal dose is within the range of 9.5 to 16.5 Gy whole body irradiation.

Depending on the purpose and application, the dose of irradiation may be administered as a single dose or as a fractionated dose. Similarly, administering one or more doses of irradiation can be accomplished essentially exclusively to the body part or to a portion thereof, so as to induce myeloreduction or myeloablation essentially exclusively in the body part or the portion thereof. As is widely recognized in the art, a subject can tolerate as sublethal conditioning ultra-high levels of selective irradiation to a body part such as a limb, which levels constitute lethal or supralethal conditioning when used for whole body irradiation (see, for example, Breitz (2002) *Cancer Biother Radiopharm.* 17:119; Limit (1997)1 *Nucl. Med.* 38:1374; and Dritschilo and Sherman (1981) *Environ. Health Perspect.* 39:59). Such selective irradiation of the body part, or portion thereof, can be advantageously used to target particular blood compartments, such as specific tissues or immune cell populations, in treating immune disorders.

c. Administration of agents

For cell-based agents, Tregs and/or Teffs can be administered at $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $5.0\times10^6$, $1.0\times10^7$, $5.0\times10^7$, $1.0\times10^8$, $5.0\times10^8$, or more, or any range in between or any value in between, cells per kilogram of subject body weight. The number of cells transplanted may be adjusted based on the desired level of engraftment in a given amount of time. Generally, $1\times10^5$ to about $1\times10^9$ cells/kg of body weight, from about $1\times10^6$ to about $1\times10^8$ cells/kg of body weight, or about $1\times10^7$ cells/kg of body weight, or more cells, as necessary, may be transplanted. In some embodiment, transplantation of at least about $0.1\times10^6$, $0.5\times10^6$, $1.0\times10^6$, $2.0\times10^6$, $3.0\times10^6$, $4.0\times10^6$, or $5.0\times10^6$ total cells relative to an average size mouse is effective.

Administration can be accomplished using methods generally known in the art. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. Cells may be administered in one infusion, or through successive infusions over a defined time period sufficient to generate a desired effect. Exemplary methods for transplantation, engraftment assessment, and marker phenotyping analysis of transplanted cells are well-known in the art (see, for example, Pearson et al. (2008) *Curr. Protoc. Immunol.* 81:15.21.1-15.21.21; Ito et al. (2002) *Blood* 100: 3175-3182; Traggiai et al. (2004) *Science* 304:104-107; Ishikawa et al. *Blood* (2005) 106:1565-1573; Shultz et al. (2005)1 *Immunol.* 174:6477-6489; and Holyoake et al. (1999) *Exp. Hematol.* 27:1418-1427).

Two or more cell types can be combined and administered, such as Tregs and adoptive cell transfer of stem cells, Tregs and Teffs, Tregs and cell-based vaccines, Tregs in combination with Teffs and cell-based vaccines, and the like. For example adoptive cell-based immunotherapies can be combined with Tregs and/or Teffs. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, and the like. The ratio of Tregs to other cell types can be 1:1, but can modulated in any amount desired (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

Engraftment of transplanted cells may be assessed by any of various methods, such as, but not limited to, tumor volume, cytokine levels, time of administration, flow cytometric analysis of cells of interest obtained from the subject at one or more time points following transplantation, and the like. For example, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or can signal the time for tumor harvesting. Any such metrics are variables that can be adjusted according to well-known parameters in order to determine the effect of the variable on a response to anti-cancer immunotherapy. In addition, the transplanted cells can be co-transplanted with other agents, such as cytokines, extracellular matrices, cell culture supports, and the like.

In addition, immune modulating agents of the present invention can be administered to subjects or otherwise applied outside of a subject body in a biologically compatible form suitable for pharmaceutical administration, to modulate immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

A combination dosage form or simultaneous administration of single agents can result in effective amounts of each desired modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984)1 Neuroimmunol. 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In some embodiments, efficacy of treatment occurs and can be measured directly or indirectly within 1, 2, 3, 4, 5, 6, 7, 8, 9, 10, 11, 12, 13, 14, or more days after initiation of administration.

In some embodiments, PD-1 or other useful biomarker nucleic acid molecules are useful and can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., *Ann N.Y. Acad Sci* 126-139, 1995). Formulation of DNA, e.g. with various lipid or liposome materials, may then be effected using known methods and materials and delivered to the recipient mammal. See, e.g., Canonico et al, *Am J Respir Cell Mol Biol* 10:24-29, 1994; Tsan et al, *Am J Physiol* 268; Alton et al., *Nat Genet.* 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., *Hum. Gene. Ther.* 3:147-154, 1992. Other vehicles which can optionally be used include DNA-ligand (Wu et al., *J. Biol. Chem.* 264:16985-16987, 1989), lipid-DNA combinations (Felgner et al., *Proc. Natl. Acad. Sci. USA* 84:7413 7417, 1989), liposomes (Wang et al., *Proc. Natl. Acad. Sci.* 84:7851-7855, 1987) and microprojectiles (Williams et al., *Proc. Natl. Acad. Sci.* 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) *Science*, 244:1275-1281; Ridgeway, 1988, supra; Baichwal and Sugden, 1986, supra; Coupar et al., 1988; Horwich et al. (1990) *J. Virol.*, 64:642-650).

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Kits

The present invention also encompasses kits. For example, the kit can comprise Tregs and/or Teffs modified as described herein, PD-1 modulatory agents, immune cells such as Teffs, immunomodulatory agents, and combinations thereof, packaged in a suitable container and can further comprise instructions for using such reagents. The kit may also contain other components, such as administration tools packaged in a separate container.

Other embodiments of the present invention are described in the following Examples. The present invention is further illustrated by the following examples which should not be construed as further limiting. The contents of all references, patents and published patent applications cited throughout this application, as well as the Figures, are incorporated herein by reference.

Examples

Example 1: Materials and Methods for Examples 2-7

A. Mice

Wild type (WT) FoxP3$^{GFP}$ reporter, PD-1$^{-/-}$ FoxP3$^{GFP}$, FoxP3$^{Cre-YFP}$ mice, and FoxP3$^{ERT2-Cre-GFP}$ mice have been previously reported in Rubtsov et al. (2008) *Immunity* 28:546-558 and Rubtsov et al. (2010) *Science* 329:1667-1671. TCRα$^{-/-}$ and CD45.1 C57Bl/6 mice were obtained from The Jackson Laboratory. To generate PD-1 conditional knockout mice, a PD-1 targeting vector containing frt sites on either side of a selection cassette containing the neo gene under control of the PGK promoter was generated. Exons 2, 3 and 4 encoding the IgV, transmembrane and first cytoplasmic exon of PD-1 were inserted into the vector downstream of the selection cassette. The flanking regions of the PD-1 gene were cloned from a PD-1-containing bacterial artificial chromosome (BAC) using standard techniques. Linearized vector DNA was electroporated into Bruce 4 C57BL/6 ES cells and the resulting neomycin-resistant ES cells were screened for homologous recombination. ES cells carrying the desired recombinant event were microinjected into blastocysts, and the resulting chimeric mice gave germline transmission of the targeted PD-1 allele. Mice carrying the targeted allele were bred with flp-expressing mice to delete Neo, yielding PD-1 conditional knockout mice (PD-1$^{fl/fl}$ mice) with exons 2, 3, and 4 flanked by loxP sites, which were bred to Foxp3$^{Cre-yfp}$ (referred to as FoxP3Cre PD-1$^{fl/fl}$ mice) or FoxP3$^{ERT2-Cre-GFP}$ (referred to as iFoxP3Cre PD-1$^{fl/fl}$ mice) mice to generate mice that selectively eliminate PD-1 in FoxP3 expressing cells constitutively or inducibly. To control for changes in FoxP3 expression due to the knock-in Cre alleles, FoxP3Cre PD-1$^{+/+}$ or iFoxP3Cre PD-1$^{+/+}$ were used as controls. The mice used in these studies were between 6-12 weeks old, and littermates were used as controls and co-housed with PD-1-deficient mice prior to experiments. To inducibly delete PD-1, iFoxP3Cre PD-1$^{fl/fl}$ mice or iFoxP3Cre PD-1$^{wt/wt}$ control mice were given 1 mg Tamoxifen (Sigma) in sunflower oil for ten consecutive days intraperitoneally (i.p.), followed by five days rest prior to experiments. For the NOD studies, Pdcd1$^{fl/fl}$ B$_6$ mice were backcrossed onto the NOD background for 11 generations and then bred with FoxP3Cre NOD mice (Zhou et al. (2008) *J. Exp. Med.* 205:1983-1991). SNP analysis of 20 Idd loci covering 144 SNPs revealed that mice were 98.5% NOD Idd loci at the F9 generation. There were four heterozygous SNPs located on chromosome 1 within the Pdcd1 gene region from the targeted Pdcd1.B6 gene construct. NOD females were used for cellular analysis. All mice were maintained in a pathogen-free facility and used according to guidelines of Harvard Medical School, University of Pittsburgh School of Medicine, and the National Institutes of Health. Harvard Medical School and the Universty of Pittsburgh School of Medicine are accredited by the American Association of Accreditation of Laboratory Animal Care.

B. Adoptive Transfer Experiments

Tregs were isolated from CD45.2 WT or PD-1$^{-/-}$ mice by enriching for CD4 cells by magnetic selection (Miltenyi) and then sorting CD4$^+$ FoxP3$^+$ cells on an Aria® (BD Biosciences) cell sorter using standard configurations. For adoptive transfer, 5×10$^5$ Tregs were injected into the tail vein of CD45.1 mice.

C. Antibodies

Anti-CD3 (145-2C11) for in vitro functional studies was obtained from BioXCell. Conjugated anti-CD4 (RM4-5), anti-CD25 (PC61), anti-CD8β (YTS156.7.7), anti-CD62L (MEL-14), anti-CD44 (IM7), anti-CTLA-4 (UC10-4B9), anti-PD-1 (RMP1-30), anti-PD-L1(10F.9G2), anti-GITR (DTA-1), anti-ICOS (C98.4A), anti-TIGIT (1G9), anti-LAP (TW7-16B4), anti-IL-10 (JESS-16E3), anti-IL-17A (TC11-18H10.1), and anti-IFNγ (XMG1.2) were purchased from BioLegend (San Diego, Calif.). Anti-CD8β (H35-17.2), anti-Bcl-2 (3F11), anti-IRF4 (3E4), and anti-Ki67 (B56) were from BD Biosciences (San Jose, Calif.). Anti-Foxp3 (FJK-16s) was purchased from eBioscience (San Diego, Calif.). Anti-LAG3 (4-10-C9) was a kind gift from D. Vignali. The BDC2.5 tetramer (AHHPIWARMDA/A$^{g7}$) was obtained from the NIH Tetramer Core Facility, and the IGRP tetramer (KYNKANVFL/H2K$^d$) was obtained from MBL International Corporation.

D. Flow Cytometry Analysis

Single-cell suspensions from spleen or lymph nodes were prepared and resuspended in staining buffer (PBS containing 1 FBS and 2 mM EDTA) and stained with the indicated antibodies. For intracellular cytokine staining, cells were activated with PMA (Sigma) and ionomycin (Sigma) in the presence of Golgistop™ (BD Bioscience) for 4 hours (hrs), followed by intracellular staining. For the detection of Foxp3 and Bcl-2, the Foxp3 staining kit from eBioscience was used according to the manufacturer's protocol for intracellular staining. Measurements of cytokines in culture supernatants were performed by cytometric bead array (CBA) (BD Biosciences). Data were acquired on a BD™ LSRII flow cytometer (BD Biosciences) and analyzed with FlowJo software (Tree Star).

E. T-Cell Sorting and Suppression Assays

CD4$^+$ T cells were purified by positive selection (Miltenyi). For in vitro suppression assays, CD4$^+$ T Tregs were sorted as CD4$^+$ Foxp3$^+$ (using either GFP or YFP reporter), and CD25$^-$ CD4$^+$ Foxp3$^-$ (using either GFP or YFP reporter), cells were sorted as T effector cells. $1 \times 10^5$ Teff cells and the indicated ratios of Tregs were stimulated using irradiated splenocytes from TCRα$^{-/-}$ mice as APCs at a 4-5:1 ratio (APCs to Teffs) and 1 µg/ml anti-CD3 mAb. Cells were cultured in RPMI 1640 (Invitrogen) supplemented with 10% FBS, 2 mM L-glutamine, 10 mM HEPES, 1% penicillin/streptomycin, and 50 µM β-mercaptoethanol for 3-4 days and culture supernatants were collected for analyses of cytokine production. In some cases, cultures were pulsed with $^3$H-thymidine and harvested 16 hours (h or hrs) later. Thymidine incorporation was measured using a beta-scintillation counter (PerkinElmer). The CellTrace™ Violet Cell Proliferation Kit was used according to the manufacture's protocol for cell trace violet labeling of effector T cells.

F. EAE Experiments

Mice were immunized with 100 µg MOG$_{35-55}$ in CFA (supplemented with 2 mg/ml heat-killed *Mycobacterium tuberculosis* H37RA) on the flanks and given 200 ng Pertussis toxin intraperitoneally on day 0 and day 2. Mice were monitored for signs of clinical disease and scored as follows: 1=limp tail, 2=weak gait, 3=hind limb paralysis, 4=hind and forelimb paralysis, and 5=moribund. For analyses of cellular infiltrates in the CNS, brain and spinal cords were isolated and resuspended in 30% percoll/PBS and overlaid above a 70% Percoll® gradient. Following centrifugation, lymphocytes in the interface were removed, washed, and resuspended in culture medium for analysis.

G. *Pneumocystis* Analyses by Histology and PCR

Lungs from mice were fixed in 10% phosphate buffered formalin, dehydrated, and embedded in paraffin. Five-micrometer paraffin tissue sections were stained with hematoxylin and eosin (H&E) or Gomori's silver stain for microscopic analyses. All slides were examined by at least one pathologist in a blinded fashion.

*Pneumocystis* infection was also tested by qPCR, as well as using histologic methods. Since *Pneumocystis* infection can be multifocal, the entire right middle and upper lobes of the lung were homogenized and tested for *Pneumocystis* spp. relative to 18S by qPCR (IDEXX BioResearch, Columbia, Mo., USA). Briefly, for *Pneumocystis* spp. PCR, DNA was extracted with standard protocols using a commercial robotic platform (One-For-All Vet Kit, Qiagen, Valencia, Calif., USA). 18S ribosomal RNA was used to determine the amounts of genomic DNA and confirm DNA integrity. The *Pneumocystis* spp. PCR test was based on the IDEXX proprietary service platform (IDEXX BioResearch, Columbia, Mo., USA). Two primers and a hydrolysis probe designed to the conserved regions of the mitochondrial large subunit rRNA gene of *Pneumocystis carinii*, *Pneumocystis wakefieldiae*, *Pneumocystis murina*, and *Pneumocystis jirovecii* were used. Real-time PCR was performed with standard primer and probe concentrations using a commercially available mastermix (LC480 ProbesMaster, Roche Applied Science, Indianapolis, Ind., USA) and real-time PCR was performed using a Roche LightCycler® 480.

H. Methylation Experiments

CD4$^+$ FoxP3$^-$ Tconv and CD4$^+$ FoxP3$^+$ Tregs were sorted from spleens of WT and PD-1$^{-/-}$ Foxp3$^{GFP}$ mice. Cells were then submitted to EpigenDx for methylation analysis of the Foxp3$^+$ Treg-specific demethylated region, TSDR, across 9 CpG regions.

I. NOD Experiments and Measurement of Diabetes and Insulitis

Diabetes incidence (high urine glucose) was monitored weekly by testing for the presence of glucose in the urine by Diastix (Bayer). Mice positive by Diastix were then bled and tested with an Ascensia® CONTOUR™ glucometer (Bayer). Mice were considered diabetic if the blood glucose level was ≥250 mg/dl. For histology, pancreata were fixed in 10% buffered formalin overnight, embedded in paraffin, and stained with hematoxylin and eosin. Islets were scored in blinded fashion as follows: 0=no infiltration, 1=perivascular/periductular infiltrates with lymphocytes touching islet perimeters, but not penetrating grade, 2=lymphocytic penetration of up to 25% of islet mass, 3=lymphocytic penetration of up to 75% of islet mass, and 4=<20% of islet mass remaining.

J. Isolation of Lymphocytes from Pancreas

For cellular analysis of lymphocytes from pancreata, mice were perfused with 10 mL of PBS. Pancreata were removed, dissociated with mechanical forces (gentleMACS™ dissociator; Miltenyi Biotec) and incubated in digestion media (Collagenase IV; Sigma and DNaseI; Sigma) in 37° C. water bath for 20 mins. The digested tissues were filtered through 70 µm strainers (BD Biosciences), washed with media, and resuspended in 44% Percoll/PBS and overlaid over 67% Percoll® gradient. Following centrifugation, lymphocytes in the interface were isolated, washed, and resuspended in culture medium for analysis.

K. Immunohistologic Analyses

For immunohistochemistry of formalin-fixed, paraffin-embedded sections, 5-micrometer sections were mounted on charged slides (Superfrost Plus; Fisher Scientific), baked for 1 hour at 60° C., deparaffinized, rehydrated, and subjected to pressure cooker antigen retrieval in a Pascal pressurized heating chamber (Dako) in pH 6 citrate buffer. After blocking endogenous peroxidase, tissue sections were incubated with a rat monoclonal antibody to Mac-2/Galectin-3 (clone M3/38; Cedarlane Labs), or a rat monoclonal antibody to FoxP3 (clone FJK-16s, eBioscience) for 1 hour at room temperature. Sections were then incubated with unconjugated rabbit anti-rat IgG (Vector Laboratories) for 30 minutes, and subsequently incubated for 40 minutes with horseradish peroxidase-conjugated rabbit-specific EnVision™ polymer (Dako) and developed using 3,3'-diaminobenzidine (DAB; Vector). Cells were then washed and incubated with a rabbit monoclonal antibody to CD3 (clone SP7; Abcam) for 60 minutes, followed by incubation with alkaline phosphatase-conjugated rabbit-specific IgG polymer (Bond Polymer Refine Red, Leica Biosystems), developing using Fast Red chromogen (Leica), and counterstaining with hematoxylin. Photomicrographs were taken with a mounted digital camera (Olympus DP71) driven by Olympus DP Controller software. Images were prepared using Adobe Photoshop and Illustrator CS3 (Adobe Systems Inc.).

L. Tumor Experiments

MC38 colorectal adenocarcinoma cells were a kind gift from D. Vignali. Cells were maintained in DMEM with 10% FBS and 1% penicillin/streptomycin. Cells were grown to 90-100% confluence and then released from culture flasks using trypsin-EDTA. Cells were resuspended in single-cell suspensions in PBS, counted, and diluted to a concentration of 1e6 cells/ml in PBS. 100 µl of cells (100e3 cells) were injected s.c. in mice 5 days after a 10 day treatment with tamoxifen as described above. Tumor size was assessed by measuring the long diameter (D) of the tumor and the corresponding perpendicular diameter (d) using a caliper, and volume was calculated as $0.5*D*d^2$. Tumors were measured every 2-3 days starting 7 days after tumor challenge. Mice were sacrificed upon tumor ulceration or upon a tumor volume of 2 cm$^3$ or greater. Cellular analysis was performed by sacrificing mice 24 days after tumor challenging and taking tumor or tumor-draining lymph node (inguinal lymph node). Tumors were mechanically disrupted and incubated in Collagenase Type I for 30 minutes at 37° C. and then smashed through a 70 µM filter. The cell pellet was then re-suspended in 40% Percoll, underlaid with 70% Percoll®, and then centrifuged at 800 g for 20 minutes without a brake. The interface was taken and stained for analysis by flow cytometry as previously described.

M. Statistical Analysis

All of the statistical analyses were performed using Prism software, version 6 (GraphPad). Results are presented as mean±SEM and significance was determined by using either an unpaired two-tailed Student's t test or a Mann-Whitney non-parametric test. Asterisks denote level of statistical significance (*p<0.05; p<0.01; and *p<0.001).

Example 2: Cell-Intrinsic Effects of PD-1 on Treg Expansion and Activation

Figure 2:
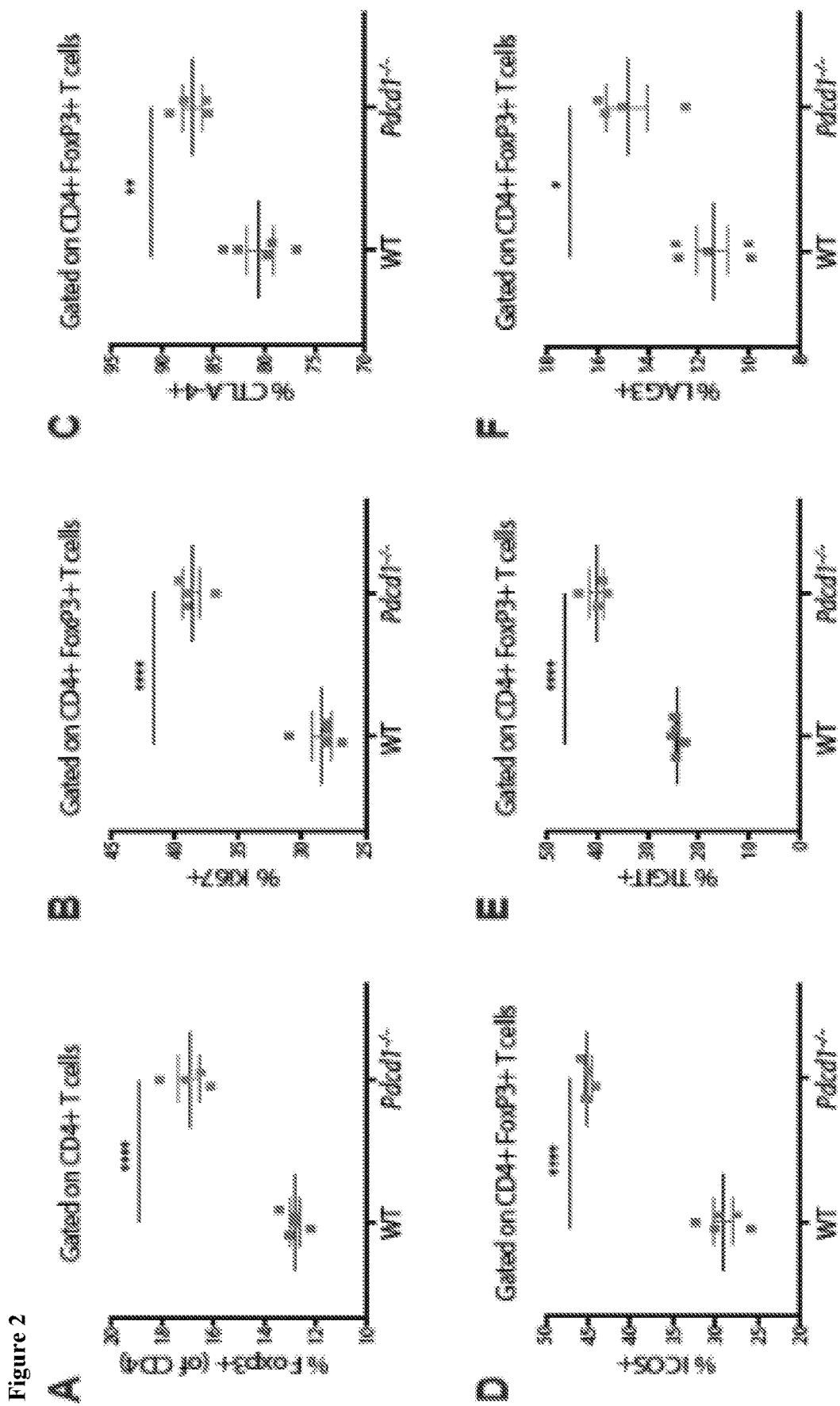
FIG. 2 includes 9 panels, identified as panels A, B, C, D, E, F, G, H, and I, which shows that PD-1-deficient Tregs have enhanced suppressive capacity. Panel A shows the results of WT and Pdcd1$^{-/-}$ mice analyzed for frequency of Treg cells of total CD4$^+$ T cells in the spleen. Panels B-F show the percentages of cells expressing Ki67 (Panel B), CTLA-4 (Panel C), ICOS (Panel D), TIGIT (Panel E), and LAG3 (Panel F) as compared between WT and Pdcd1$^{-/-}$ mice. Panel G shows the results of IRF4 expression level assessed in WT and Pdcd1$^{-/-}$ Tregs. Panel H shows the results of a Treg suppression assay in which WT or Pdcd1$^{-/-}$ Tregs were sorted and cultured with CD4$^+$ Foxp3$^-$ effector T cells (Teff), irradiated APCs, and anti-CD3 for 4 days at 1:4 and 1:1 Treg to Teff cell ratios, and analyzed for $^3$H-thymidine incorporation. Panel I shows the results of a Treg suppression assay as in Panel H with effector T cell proliferation measured by Cell Trace Violet dilution. Data are representative of at least 2 or more similar experiments (n=4 mice per group). Data are represented as the means±SEM. * p<0.05,  p<0.01, * p<0.001.
Figure 2:
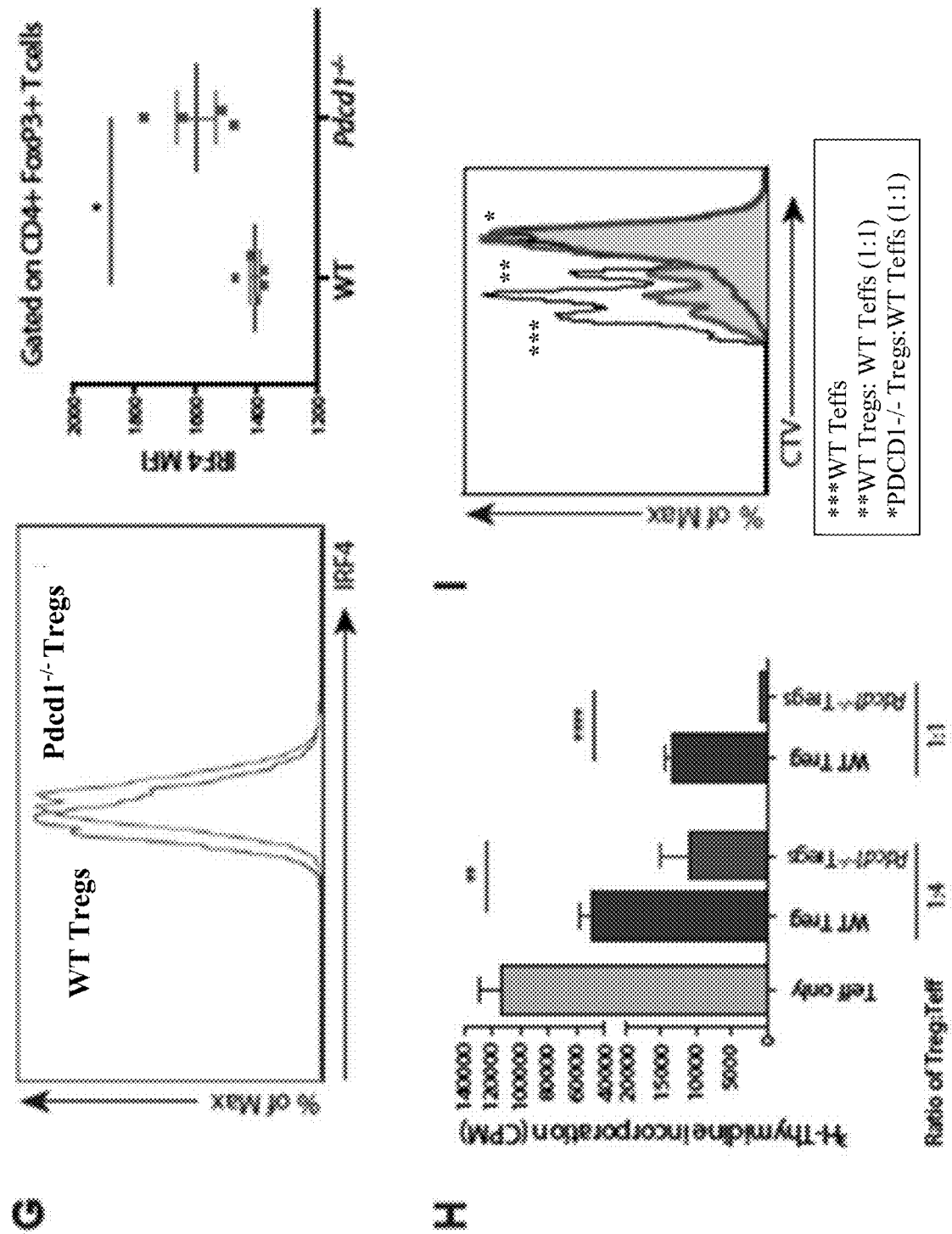
Figure 3:
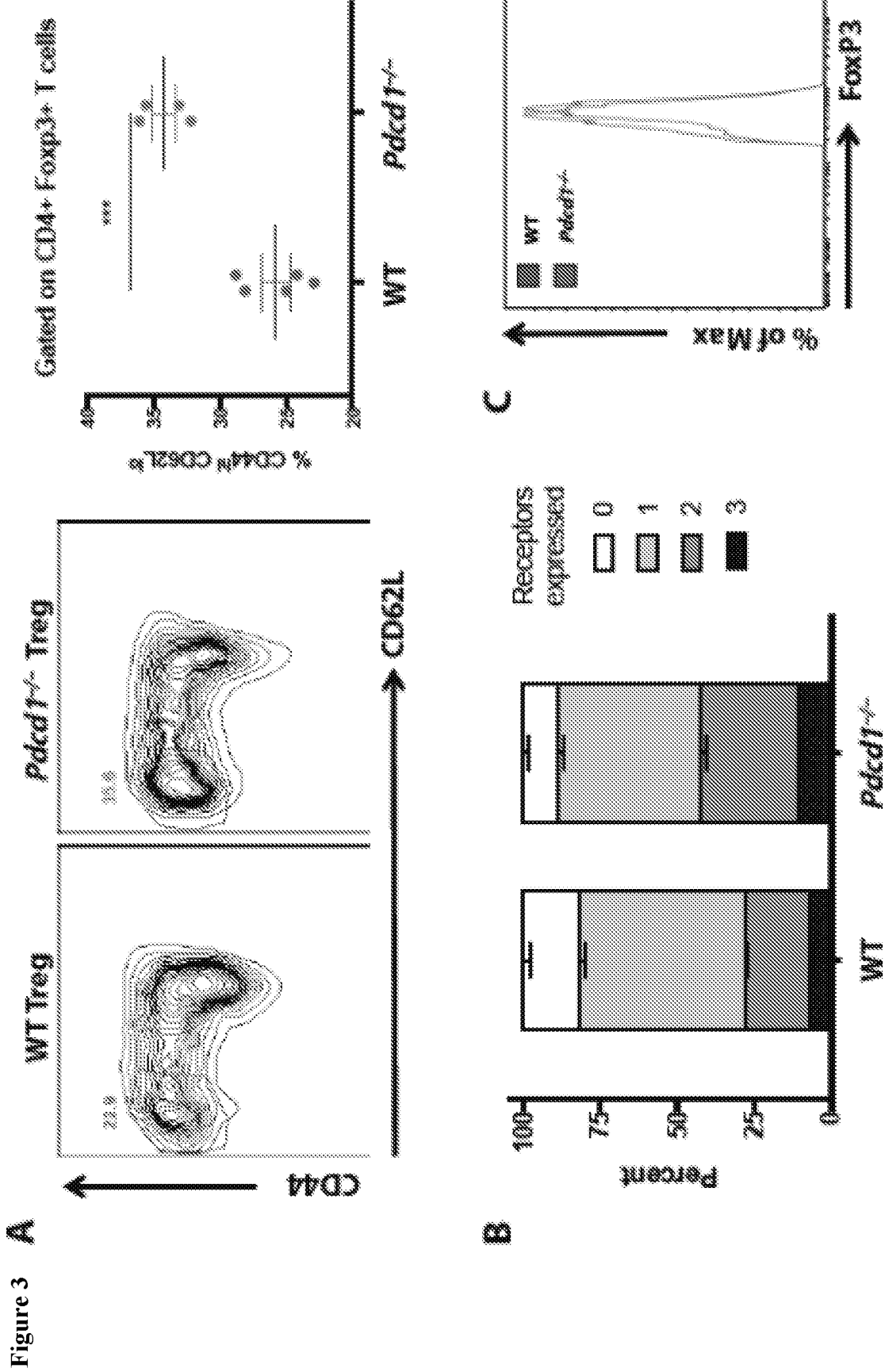
FIG. 3 includes 3 panels, identified as panels A, B, and C, which show a comparison of WT and PD-1-deficient Tregs. Panel A shows the results of WT and Pdcd1$^{-/-}$ Tregs analyzed for CD44 and CD62L expression (left panel). Representative plots are gated on CD4$^+$ FoxP3$^+$ T cells. Percentages of CD44$^{hi}$ CD62L$^{lo}$ Treg cells in WT or Pdcd1$^{-/-}$ mice in the spleen (right panel). Panel B shows the percentages of WT or Pdcd1$^{-/-}$ Tregs that co-express CTLA-4, LAG3 and TIGIT using Boolean gating analysis via Flowjo. WT or Pdcd1$^{-/-}$ Tregs were grouped based on total numbers of receptors expressed. Panel C shows the expression of FoxP3 in WT or Pdcd1$^{-/-}$ Tregs from spleens. Data are representative of 2 experiments with n=5 mice per group. * p<0.05,  p<0.01, * p<0.001.

Treg homeostasis and function in naïve wild-type (WT) and PD-1 null mice (PD-1$^{-/-}$) were analyzed and a modest increase in regulatory T cell (Treg) frequency in the spleen and lymph nodes of PD-1$^{-/-}$ mice was observed (FIG. 2). Increased frequencies of CD44$^{hi}$CD62$^{lo}$ activated Tregs were observed in the spleen (FIG. 3A) and higher Ki67 expression in PD-1$^{-/-}$ mice compared to wild-type mice (FIG. 2B). In addition, there were greater percentages of Tregs expressing CTLA-4 (FIG. 2C), ICOS (FIG. 2D), TIGIT (FIG. 2E), and LAG3 (FIG. 2F) in the Pdcd1$^{-/-}$ mice and an increased frequency of Tregs co-expressing multiple co-inhibitory molecules (FIG. 3B). Interestingly, Pdcd1$^{-/-}$ Tregs expressed higher levels of IRF4 (FIG. 2G), a transcription factor important for optimal Treg suppressive ability (Zheng et al. (2009) *Nature* 458:351-356; Levine et al. (2014) *Nat. Immunol.* 15:1070-1078), while levels of FoxP3 were comparable between Pdcd1$^{-/-}$ and WT Tregs (FIG. 3C). Together, these findings show that Tregs from Pdcd1$^{-/-}$ mice exhibit a more activated phenotype. The increased expression of CTLA-4, TIGIT and IRF4 indicate that Pdcd1$^{-/-}$ Tregs may be more potent suppressors than wild-type (WT) Tregs.

Example 3: PD-1 Regulates Treg Suppression of Teffs

In order to determine how PD-1 deficiency affects Treg function, an in vitro Treg-mediated suppression assay was used. WT or PD-1$^{-/-}$ Tregs were cultured with naïve CD4$^+$ effector T cells (Teffs) in the presence of irradiated APCs and anti-CD3 for 3 to 4 days. Tregs more potently suppressed Teff cell proliferation, as measured by 3H-thymidine incorporation (FIG. 2H) or by dilution of CellTrace Violet in effector T cells (FIG. 2I) compared to WT Tregs. In addition, PD-1$^{-/-}$ Tregs more potently suppressed Teff. These data indicate that PD-1 restrains Treg suppressive function and that loss of PD-1 enhances their suppressive capacity.

Figure 4:
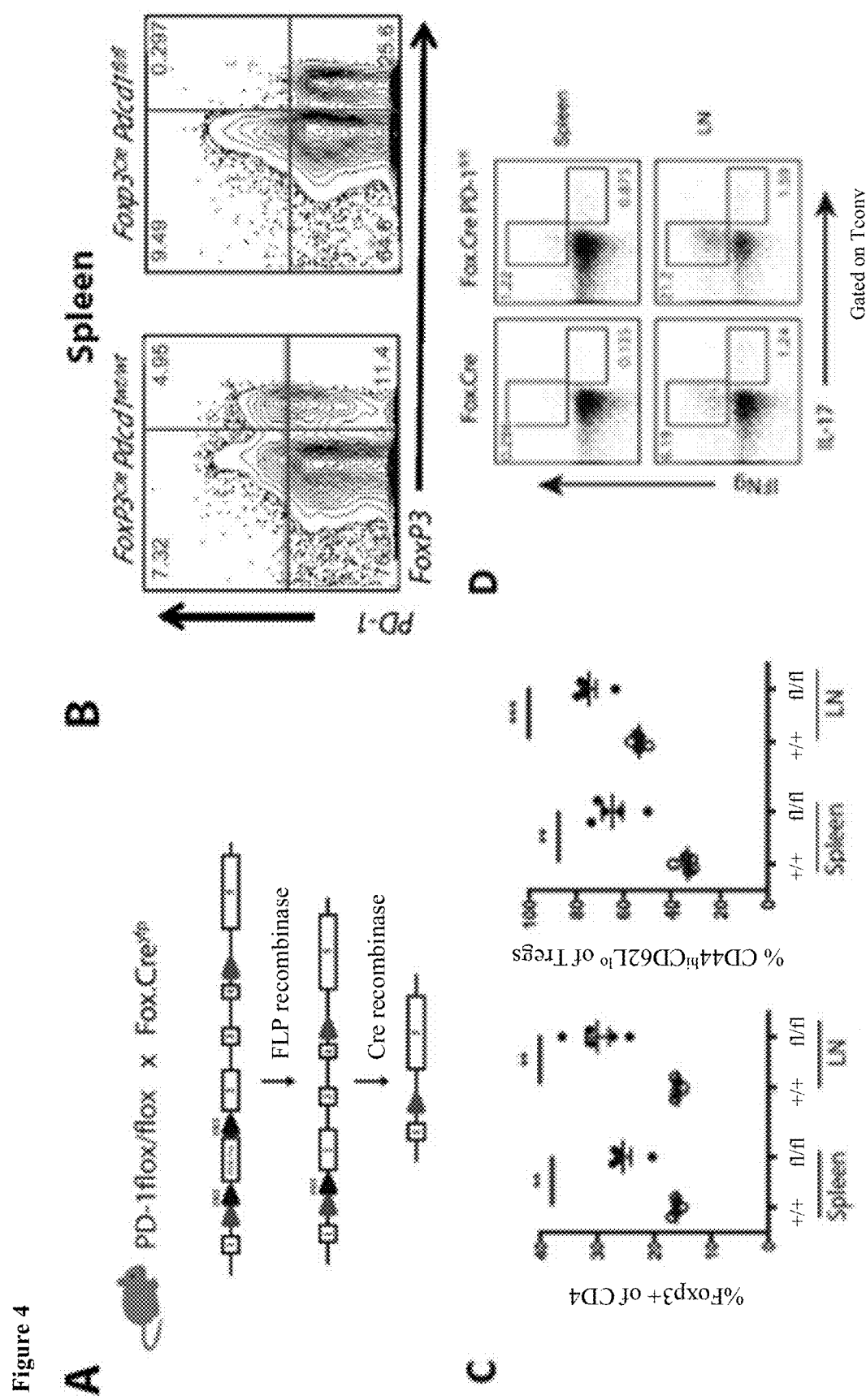
FIG. 4 includes 7 panels, identified as panels A, B, C, D, E, F, and G, which show that mice lacking PD-1 in Treg cells mice succumb to Pneumocystis infection. Panel A shows a schematic showing generation of Treg specific PD-1 conditional knockout mice, referred to as FoxP3Cre Pdcd1$^{fl/fl}$ mice. Panel B shows the results of spleens from FoxP3Cre Pdcd1$^{wt/wt}$ or FoxP3Cre Pdcd1$^{fl/fl}$ mice analyzed for PD-1 expression. Plots are gated on CD4+ cells. Panel C shows the percentages of CD4 Tconv, CD44$^{hi}$CD62L$^{lo}$ CD4 Tconv, and CD44$^{hi}$CD62L$^{lo}$ Tregs, compared in spleen and LN from FoxP3Cre and FoxP3Cre PD-1$^{fl/fl}$ mice in a colony in which mice eventually succumb to Pneumocystis infection. Panel D shows the results of intracellular cytokine production compared in Tconv cells in the spleen and LNs 5 days post-MOG 35-55 immunization. The results are representative of more than 3 experiments (n=6 FoxP3Cre mice and n=5 FoxP3Cre PD-1$^{fl/fl}$ mice) and p-values are as follows: *<0.05; <0.01; and *<0.001. Panel E shows lungs from FoxP3Cre Pdcd1$^{fl/fl}$ control and FoxP3Cre Pdcd1$^{fl/fl}$ mice. Arrows denote multiple white foci of infection. Panel F shows the results of qPCR for Pneumocystis spp. from the lungs of iFoxP3Cre Pdcd1$^{fl/fl}$ compared with those from iFoxP3Cre Pdcd1$^{fl/fl}$, FoxP3Cre Pdcd1$^{wt/wt}$, and FoxP3Cre Pdcd1$^{fl/fl}$ mice. Panel G shows the results of immunohistochemical analysis of CD3$^+$ Tconv cells and FoxP3$^+$ Treg cells (left panel) and Mac-1$^+$ macrophages (right panel) in the lungs of FoxP3Cre Pdcd1$^{fl/fl}$ vs. FoxP3Cre Pdcd1$^{wt/wt}$ control mice (200× and 400× magnification shown). Data are representative of >3 experiments with n=6 FoxP3Cre and n=5 FoxP3Cre PD-P$^{fl}$ mice. * p<0.05,  p<0.01, * p<0.001.
Figure 4:
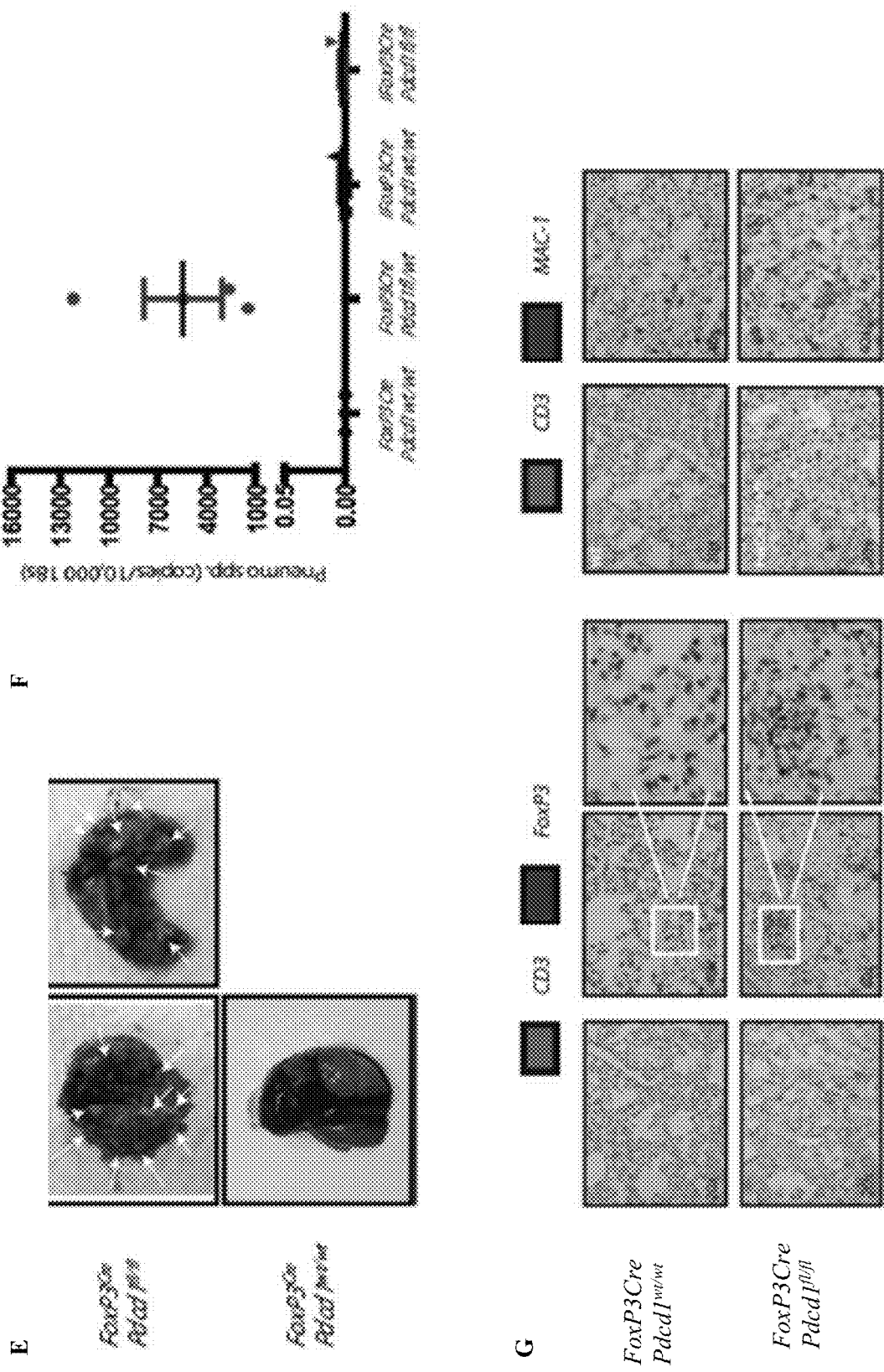
Figure 5:
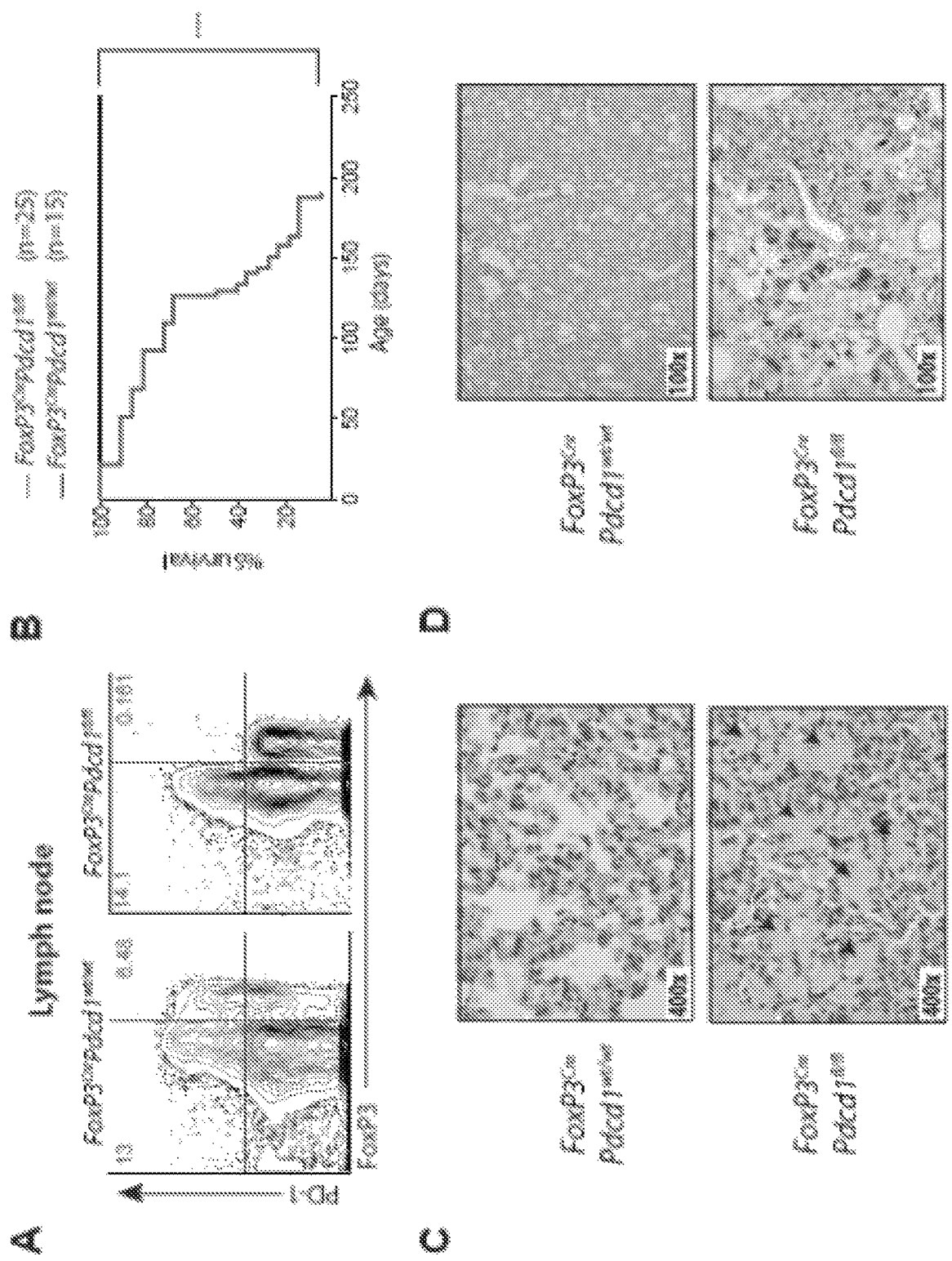
FIG. 5 includes 4 panels, identified as panels A, B, C, and D, which further show that mice lacking PD-1 specifically in Tregs succumb to opportunistic Pneumocystis infection of the lung. Panel A shows the results of lymph nodes from FoxP3Cre PD-1$^{+/+}$ mice (control) or FoxP3CrePD-1$^{fl/fl}$ (Treg PD-1-deleted) mice analyzed for FoxP3 and PD-1 expression. Plots are pre-gated on CD4$^+$ cells. Panel B show survival curves of FoxP3Cre PD-1$^{+/+}$ mice and FoxP3CrePD-1$^{fl/fl}$ mice over 240 days. Panels C and D show fatal Pneumocystis infection in the lungs of mice lacking PD-1 on Tregs. Representative H&E staining (panel C) and silver staining (panel D) images of lungs from FoxP3Cre PD-1$^{fl/fl}$ mice (n=25) or FoxP3Cre Pdcd1$^{wt/w}$ control mice (n=18) are shown at 100× and 400× magnification. Log-rank (Mantel-Cox) test was used for the data show in Panel B. * p<0.05,  p<0.01, * p<0.001.

Example 4: Treg-Specific PD-1 Deficiency Promotes Suppression of Teffs In Vitro and In Vivo In order to determine how PD-1 deficiency affects Treg function in vivo without the confounding effects of PD-1 deletion on other hematopoietic cells, PD-1-floxed mice (PD-1$^{fl/fl}$) were generated and were crossed with FoxP3$^{Cre-YFP}$ mice (Rubtsov et al. (2008) *Immunity* 28:546-558) to generate mice in which PD-1 is deleted only on regulatory T cells (referred to as FoxP3Cre PD-1$^{fl/fl}$ mice) (FIG. 4A). PD-1 is expressed on T cells, NK, NKT, B cells, and some populations of myeloid cells (Francisco et al. (2009) *Immunol. Rev.* 236:219-242) and is deleted in all of these cell types in the PD-1 germline deleted mice. Analysis of spleens and lymph nodes (LNs) from FoxP3Cre PD-1$^{fl/fl}$ mice for PD-1 expression confirmed selective deletion of PD-1 on Tregs (FIGS. 4B and 5A). Tregs were increased in FoxP3Cre PD-1$^{fl/fl}$ mice as compared to FoxP3Cre controls (FIG. 4C) and the Tregs from FoxP3$^{Cre}$Pdcd1$^{fl/fl}$ mice exhibited a more activated phenotype as indicated by increased percentages of CD44$^{hi}$ CD62L$^{lo}$ Tregs (FIG. 4C).

Surprisingly, soon after establishing a homozygous colony of FoxP3Cre PD-1$^{fl/fl}$ mice, these mice began to lose weight and died between 3-27 weeks of age, while mice from the control FoxP3Cre colony remained healthy (FIG. 5B). The rapidity of onset and percentage of mice in the FoxP3Cre PD-1$^{fl/fl}$ colony that died progressively increased over generations, suggesting that these mice were susceptible to an opportunistic infection. In order to determine whether the death of FoxP3Cre PD-1$^{fl/fl}$ mice was due to immunosuppression and/or development of spontaneous autoimmunity, the mice were histopathologically analyzed. The lungs of FoxP3Cre PD-1$^{fl/fl}$ mice had white nodules throughout the lobes (FIG. 4E). Histopathological analysis of the lungs revealed intra-alveolar amorphous eosinophilic foamy material with scant inflammatory infiltrates composed mainly of mononuclear cells (FIG. 5C). These findings are characteristic of infection with *Pneumocystis*, an opportunistic fungus which typically infects immunocompromised hosts. Silver staining of lung sections revealed cup shaped cysts pathognomonic of *Pneumocystis* (FIG. 5D). Additionally, real-time PCR was used to verify that these mice were infected with *Pneumocystis* (FIG. 4F). Immunohistological analyses revealed increased FoxP3+ Tregs and macrophages in the lungs of the FoxP3Cre Pdcd1$^{fl/fl}$ mice (FIG. 4G). Therefore, PD-1 deficiency on Tregs alone results in increased Treg cell frequency, enhanced Treg suppressive function, and susceptibility to opportunistic *Pneumocystis* pneumonia.

Figure 6:
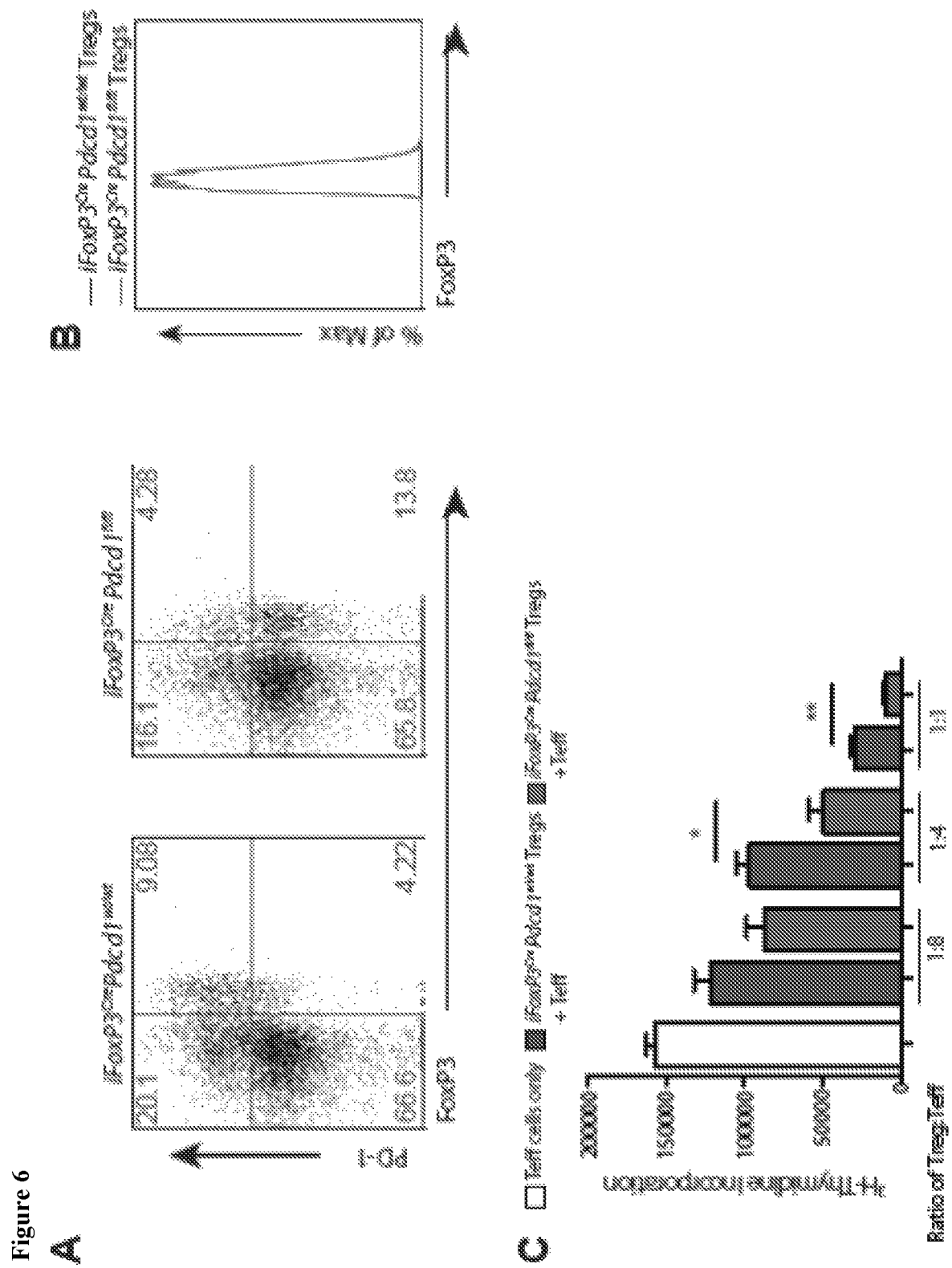
FIG. 6 includes 5 panels, identified as panels A, B, C, D and E, which shows that inducible deletion of PD-1 on Tregs enhanced the capacity of Tregs to suppress T effector cells in vitro. Panel A shows the results of FoxP3$^{ERT2-CreGFP}$ PD-1$^{+/+}$ (iFoxP3Cre Pdcd1$^{wt/wt}$) mice or FoxP3$^{ERT2-CreGFP}$ PD-1$^{fl/fl}$ (iFoxP3Cre PD-1$^{fl/fl}$) mice analyzed for PD-1 and FoxP3 expression 5 days after daily administration of tamoxifen for 10 days. Plots are pre-gated on CD4$^+$ cells. Panel B shows a histogram of FoxP3 expression pre-gated on CD4$^+$ FoxP3$^+$ cells from panel A. Panel C shows the results of an in vitro suppression assay comparing control and PD-1 inducibly-deleted Tregs (generated as in panel A) cultured with CD4$^+$ FoxP3$^-$ effector T cells (Teff), irradiated APCs plus anti-CD3 for 4 days at 1:8, 1:4 and 1:1 Treg-to-Teff cell ratios. Proliferation was measured by $^3$H-thymidine incorporation. Panel D and E shows the results of cytokines from culture supernatants analyzed at day 4 of culture from assays as in panel C. Data are representative of 3 independent experiments in panels C, D and E. Data are represented as the means±SEM. * p<0.05,  p<0.01, * p<0.001.
Figure 6:
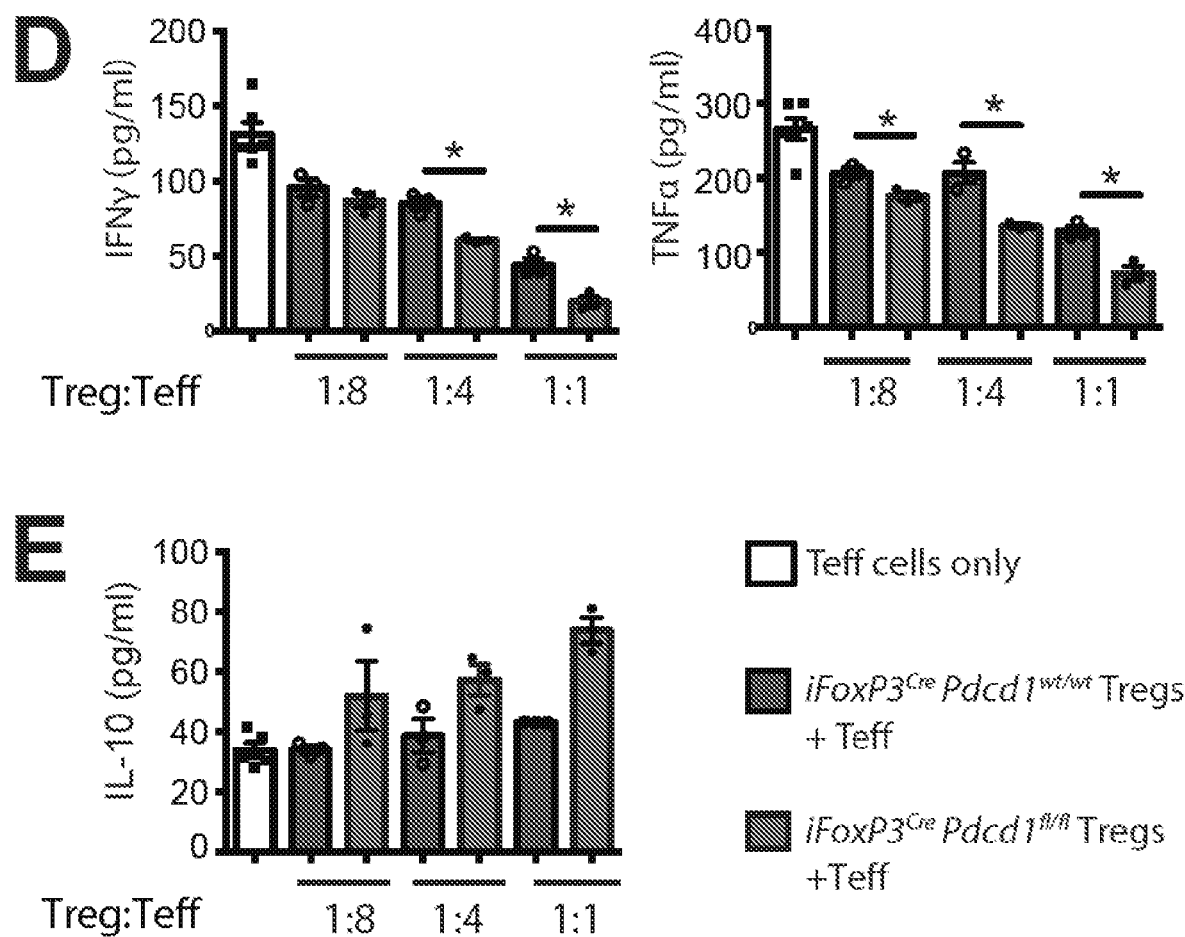
Figure 7:
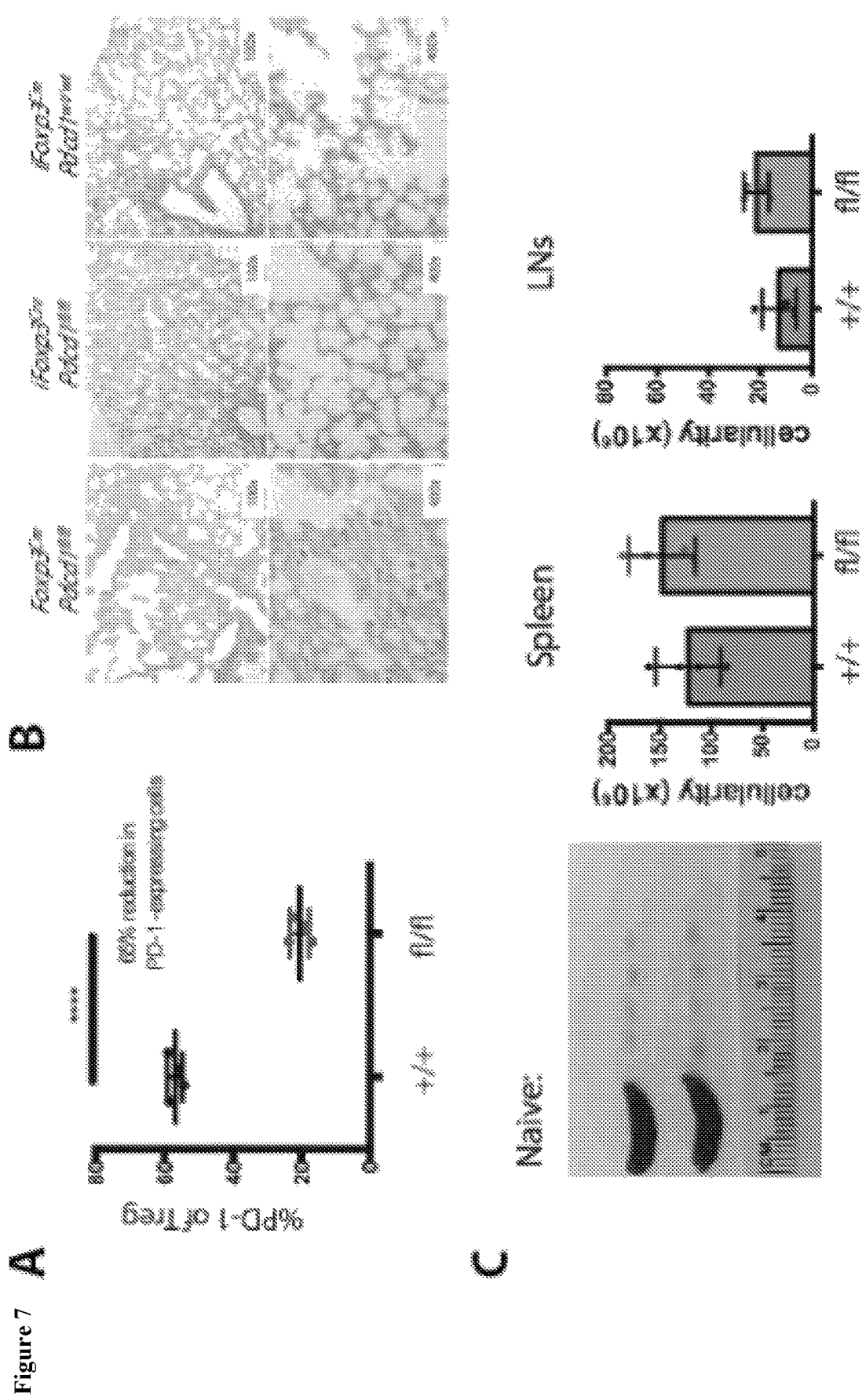
FIG. 7 includes 3 panels, identified as panels A, B, and C, which show further characterization of mice in which PD-1 was inducibly deleted specifically on Tregs. Panel A shows the results of iFoxPCre PD-1$^{fl/fl}$ (fl/fl) mice or iFoxPCre Pdcd1$^{wt/wt}$ (+/+) mice analyzed for PD-1 expression on FoxP3$^+$ Tregs 5 days after tamoxifen administration administered daily for 10 days. Panel B shows lung sections of iFoxP3Cre PD-1$^{fl/fl}$ mice, iFoxP3Cre Pdcd1$^{wt/wt}$ mice, and FoxP3Cre PD-1$^{fl/fl}$ positive control mice, stained with silver staining to identify *Pneumocystis* infection. The upper images of panel D show 100× magnification and the lower images of panel D show 400× magnification. Panel C shows the results of spleens and LNs from iFoxPCre Pdcd1$^{wt/wt}$ control mice and iFoxPCre PD-1$^{fl/fl}$ mice examined macroscopically and analyzed for cellularity after tamoxifen treatment as in panel A. The results are representative of 2 experiments (n=4 mice per group) and p-values are as follows: *<0.05; <0.01; and * p<0.001.

Example 5: Inducible Deletion of PD-1 in Tregs Results in Enhanced Suppression of Effector T Cells In Vitro In order to further characterize the function of PD-1 on Tregs without the confounding effects of opportunistic *Pneumocystis* infection in the FoxP3Cre Pdcd1$^{fl/fl}$ mice and effects of PD-1 deletion in other hematopoietic cells in Pdcd1$_{fl/fl}$ mice, mice were generated in which PD-1 was inducibly and selectively deleted on Tregs by breeding Foxp3$^{ERT2.Cre}$ mice with PD-1$^{fl/fl}$ mice (referred to as iFoxP3Cre PD-1$^{fl/fl}$ mice). PD-1 was selectively deleted on Tregs in the resulting iFoxP3Cre PD-1$^{fl/fl}$ mice only upon administration of tamoxifen (FIGS. 6A and 7A). This approach enabled the analysis of PD-1 deletion effects solely in Tregs in mice that develop with a normal immune system. In order to ensure that these mice were devoid of *Pneumocystis* infection, H&E- and silver-stained sections of lungs were analyzed and qPCR analyses were conducted. *Pneumocystis* was not detected in these mice at 6 weeks post-PD-1 deletion on Tregs (FIGS. 4F and 7B). Inducible deletion of PD-1 in Tregs in the iFoxP3Cre PD-1$^{fl/fl}$ mice did not lead to differences in the cellularity of peripheral lymphoid organs (FIG. 7C), nor alterations in FoxP3 expression (FIG. 6B).

The suppressive capacity of Tregs from iFoxP3Cre PD-1$^{fl/fl}$ mice was also analyzed in vitro. Tregs were isolated from iFoxP3Cre PD-1$^{fl/fl}$ or iFoxP3Cre PD-1$^{+/+}$ (iFoxP3Cre) control mice 5 days after in vivo treatment with the last dose of tamoxifen and were cultured with CD4$^+$ FoxP3$^-$ T effector cells using the in vitro suppression assay described in Example 3 above. iFoxP3Cre PD-1$^{fl/fl}$ Tregs more potently suppressed CD4$^+$ effector T cell proliferation and cytokine production (e.g., IFNγ, IL-2, and TNFα) as compared to iFoxP3Cre Tregs (FIGS. 6C-6D). IL-10 was increased in cultures with iFoxP3Cre PD-1$^{fl/fl}$ Tregs (FIGS. 6C-6D). Thus, inducible deletion of PD-1 on Tregs increases the suppressive capacity of Tregs to inhibit CD4$^+$ Foxp3$^-$ T cell proliferation and cytokine production.

Example 6: Inducible Deletion of PD-1 in Tregs Ameliorates Experimental Autoimmune Encephalomyelitis (EAE)

Figure 8:
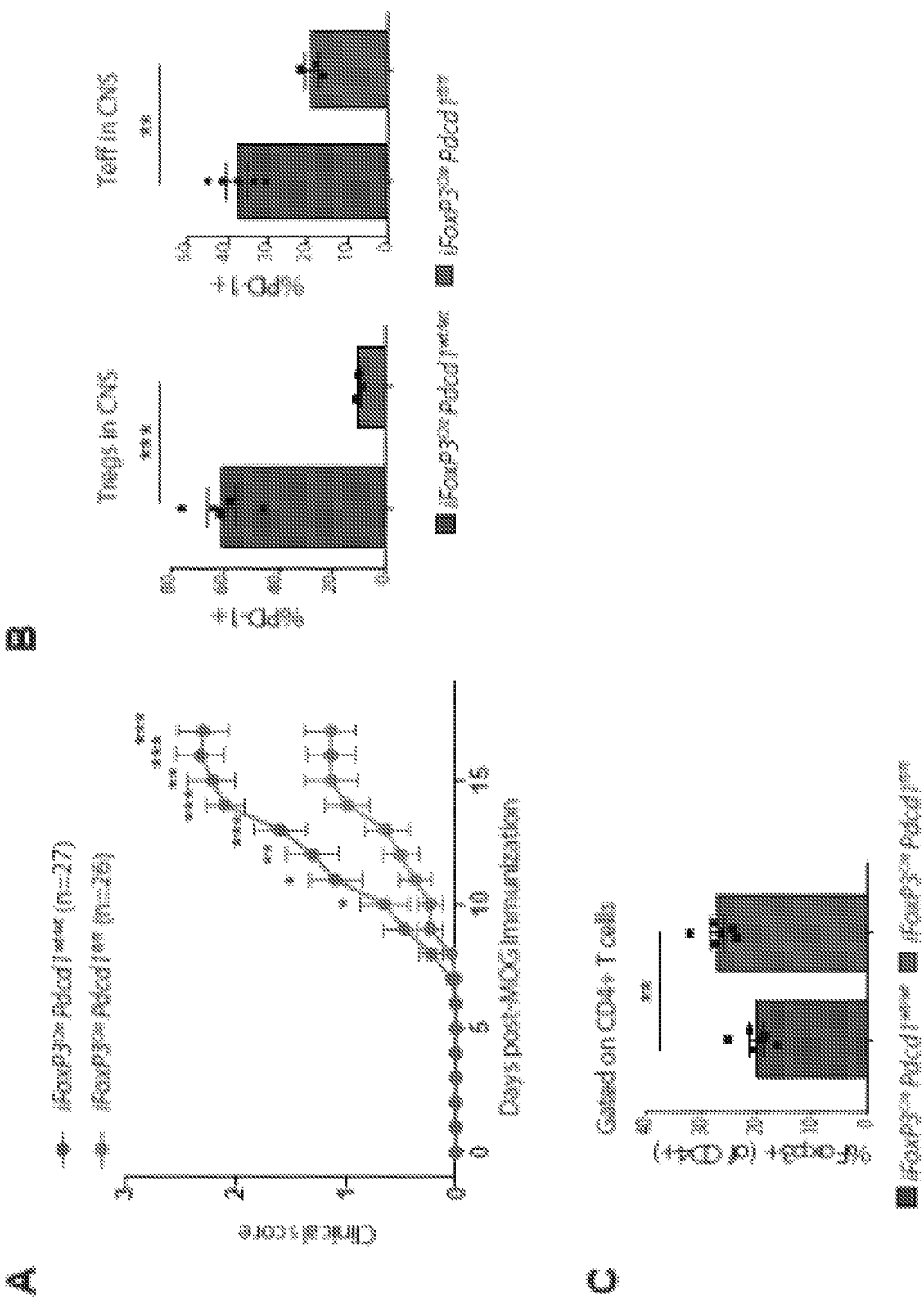
FIG. 8 includes 7 panels, identified as panels A, B, C, D, E, F, and G, which show that inducible deletion of PD-1 in Tregs results in protection from EAE. Panel A shows the results of iFoxP3Cre Pdcd1$^{wt/wt}$ or iFoxP3Cre Pdcd1$^{fl/fl}$ mice were given tamoxifen for 10 days and then immunized with MOG$_{35-55}$/CFA 5 days after the last tamoxifen dose to induce EAE. Mice were monitored daily for signs of clinical disease. Panel B shows a comparison of PD-1 expression in Tregs (left panel) and T effector cells (right panel) from the CNS of iFoxP3Cre Pdcd1$^{wt/wt}$ and iFoxP3Cre Pdcd1$^{fl/fl}$ mice on day 17 post MOG immunization. Percentages of cells that express PD-1 are shown. Panel C shows percentages of Tregs of total CD4$^+$ in the CNS and Panel D shows the numbers of Treg cells of total CD4$^+$ from the CNS of iFoxP3Cre Pdcd1$^{wt/wt}$ and iFoxP3Cre Pdcd1$^{fl/fl}$ mice on day 17 post MOG immunization. CD4$^+$ FoxP3$^-$ T effector cells were analyzed for IFN-γ and IL-17A 28 production in the CNS (Panel E) or cervical lymph node (cLN) (Panel F) by intracellular staining. Panel G shows the results of EAE induced in FoxP3$^{ERT2-CreGFP}$ PD-1$^{+/+}$ (iFoxP3Cre) mice or FoxP3$^{ERT2-CreGFP}$ PD-1$^{fl/fl}$ (iFoxP3Cre PD-1$^{fl/fl}$) mice, wherein PD-1 deletion starting around day 9-10 occurred after daily administration of tamoxifen on day 6 until day 16. Data were pooled from 4 independent experiments in Panel A. Data are representative of 3 independent experiments in Panels B, E, and F. Data are representative of 2 independent experiments in Panels C and D. Mann-Whitney nonparametric test was used. Data are represented means±SEM. * p<0.05<,  p<0.01, * p<0.001.
Figure 8:
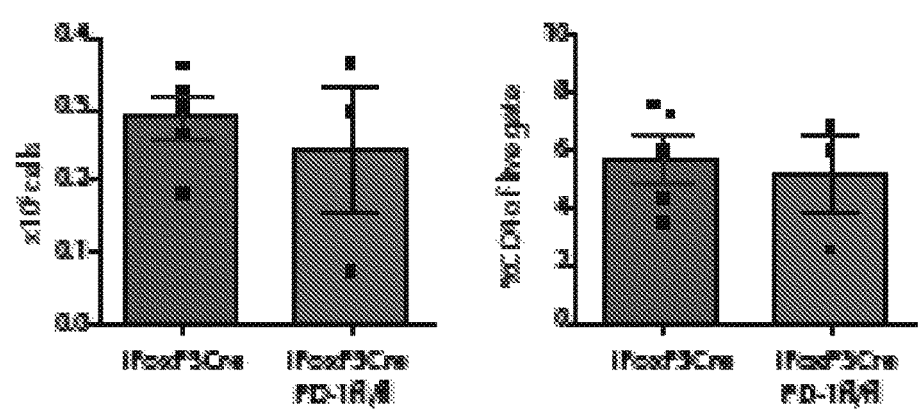
Figure 8:
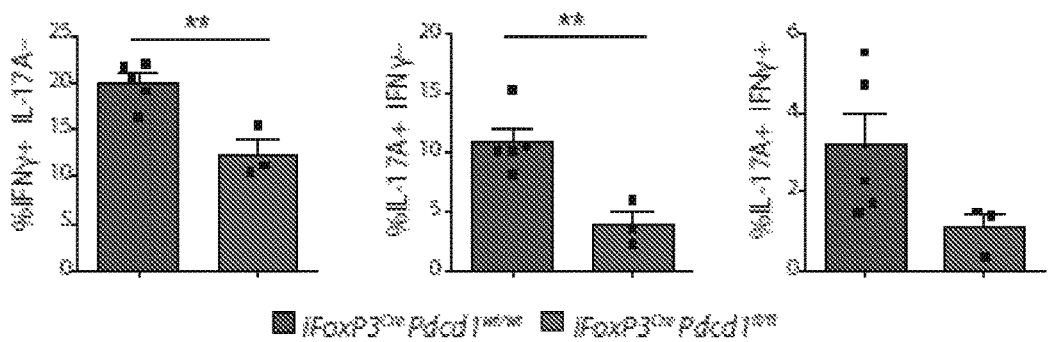
Figure 8:
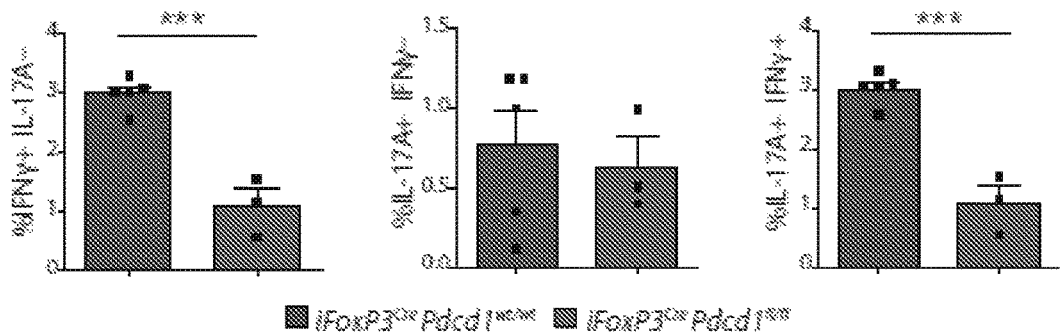
Figure 8:
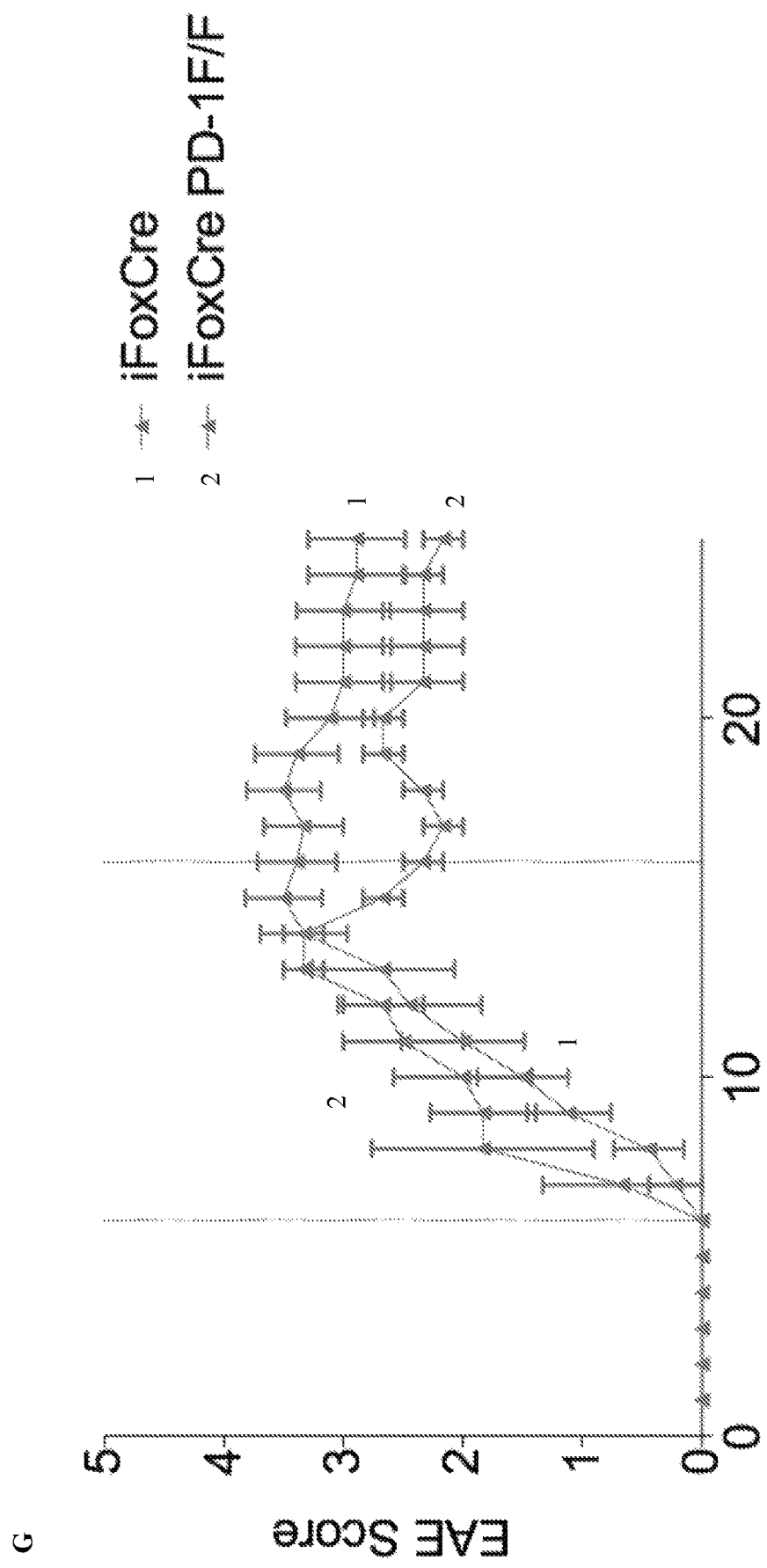

In order to further investigate the suppressive capacity of Tregs from iFoxP3Cre PD-1$^{fl/fl}$ mice, their ability to suppress T effector cells in vivo in the setting of experimental autoimmune encephalomyelitis (EAE) was tested. iFoxP3Cre PD-1$^{fl/fl}$ and iFoxP3Cre PD-1$^{+/+}$ mice were given tamoxifen to delete PD-1 in the floxed mice and then immunized with MOG$_{35-55}$/CFA in order to induce EAE. iFoxP3Cre PD-1$^{fl/fl}$ mice developed less severe EAE compared to iFoxP3Cre mice (FIG. 8A), in contrast to exacerbated EAE that develops in PD-1$^{-/-}$ mice (Wang et al. (2009) *Immunol.* 126:329-335). Tregs in the CNS of iFoxP3Cre PD-1$^{fl/fl}$ mice showed markedly reduced PD-1 expression, consistent with deletion of PD-1 (FIG. 4F). Interestingly, a decrease in PD-1 expression on CD4ToxP3$^-$ effector T cells in the CNS was observed, likely due to the reduced disease severity since PD-1 expression is induced by T cell activation (FIG. 8B). There was an increased frequency of Tregs (FIG. 8C) in the CNS of iFoxP3Cre PD-1$^{fl/fl}$ compared to iFoxP3Cre PD-1$^{wt/wt}$ mice despite similar Treg cell numbers (FIG. 8D). Furthermore, there were reduced frequencies of IFN-γ- and IL-17A-producing CD4$^+$ FoxP3$^-$ effector T cells in the CNS and cervical lymph nodes (cLN) of iFoxP3Cre PD-1$^{fl/fl}$ compared to iFoxP3Cre PD-1$^{wt/wt}$ mice (FIGS. 8E-8F). These findings indicate that attenuated EAE severity upon inducible PD-1 deletion in Tregs is likely due to increased Treg frequency in the CNS, and enhanced Treg function that limits effector T cell proinflammatory cytokine production.

Figure 9:
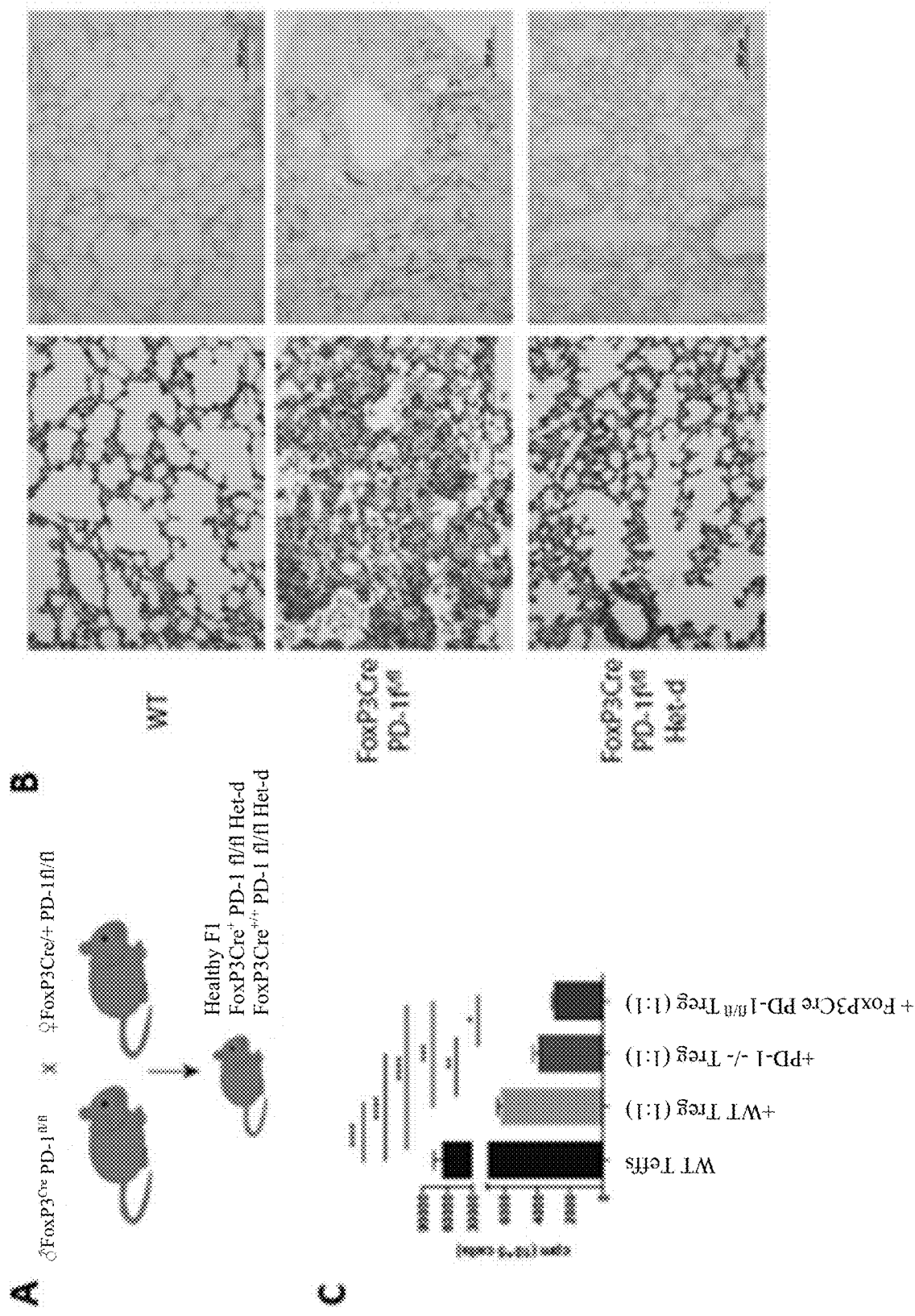
FIG. 9 includes 5 panels, identified as panels A, B, C, D, and E, which show that mice lacking PD-1 on Tregs generated from an F1 cross of a non-PD-1 deleted mother do not have *Pneumocystis* infection. Panel A shows a schematic of the mouse breeding strategy. Hemizygous FoxP3$^{Cre}$ PD-1$^{fl/fl}$ males were bred with heterozygous FoxP3$^{Cre/+}$ PD-1$^{fl/fl}$ females to generate F1 progeny, referred to as FoxP3Cre PD-1 fl/fl "Het-d." Panel B shows the results of 18 week-old mice from panel A examined by hematoxylin and eosin (H&E) staining and silver staining of the lung. The results are representative of n=12 FoxP3Cre PD-1 fl/fl "Het-d" mice and n=11 control mice. Mice born from crossing FoxP3$^{Cre}$ PD-1$^{fl/fl}$ mice and FoxP3$^{Cre/Cre}$ PD-1$^{fl/fl}$ mice as parents (FoxP3 Cre PD-1$^{fl/fl}$ mice) are shown as positive controls for *Pneumocystis* infection. Panel C shows the results of a suppression assay in which FoxP3$^+$ Tregs were sorted from FoxP3Cre PD-1 fl/fl "Het-d" mice or FoxCre control mice, and cultured with WT FoxP3$^-$ Teff cells (1:1) for 3 days in the presence of irradiated APC and anti-CD3. Cultures were analyzed for $^3$H-thymidine incorporation. Panel D shows the results of EAE in FoxP3Cre PD-1 fl/fl "Het-d" mice and WT control mice. Panel E shows maximum clinical scores from the results shown in panel D.
Figure 9:
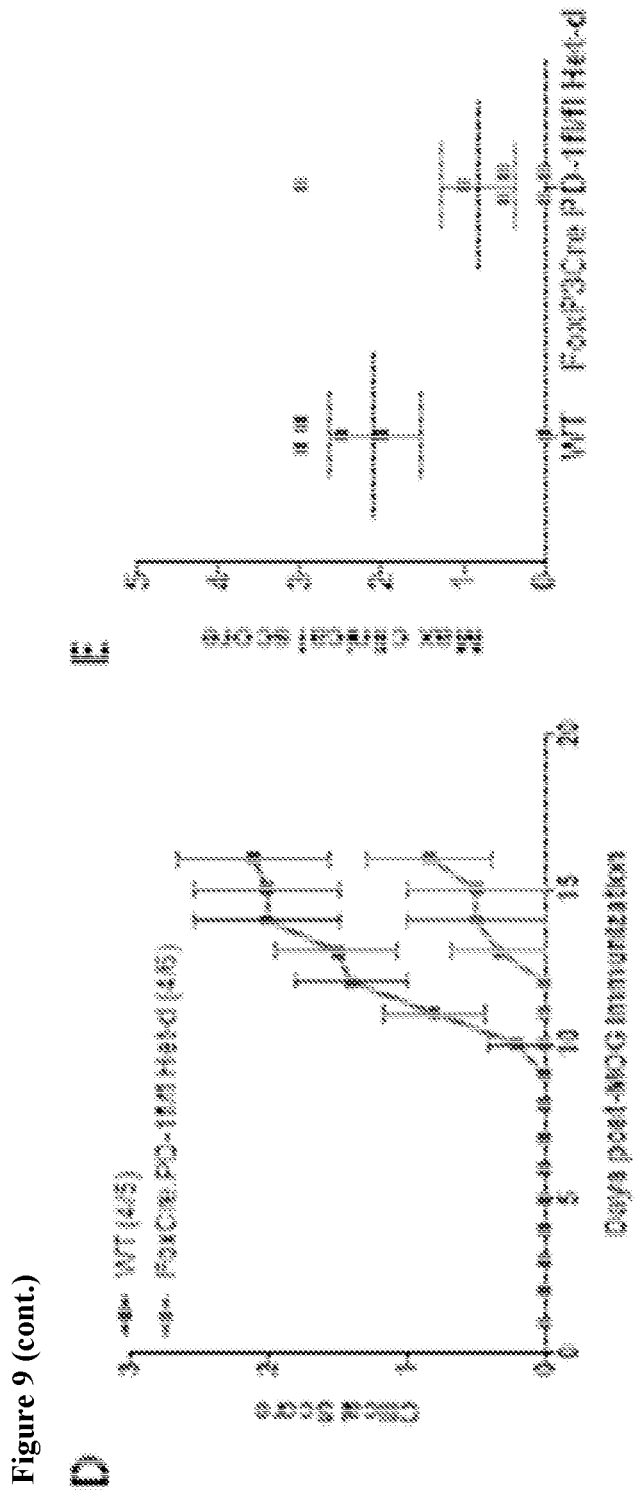

During the course of studies with the iFoxP3Cre PD-1$^{fl/fl}$ mice, the non-inducible FoxP3Cre PD-1$^{fl/fl}$ mice were re-derived and a *Pneumocystis*-free colony of FoxP3Cre PD-1$^{fl/fl}$ mice were generated with FoxP3Cre PD-1$^{fl/fl}$ mothers that are not susceptible to *Pneumocystis*. Similar to iFoxP3Cre PD-1$^{fl/fl}$ mice, Tregs from these FoxP3Cre PD-1$^{fl/fl}$ mice more potently suppressed Teff cells in vitro. In vivo, these FoxP3Cre PD-1$^{fl/fl}$ mice displayed delayed onset and reduced severity of EAE compared to FoxP3Cre control mice (FIG. 9). Together, these findings demonstrate that PD-1 loss solely on Tregs results in a more potent Treg population that can suppress EAE in vivo.

Example 7: Non-Obese Diabetic (NOD) Mice that Selectively Lack PD-1 in Tregs are Protected from Type 1 Diabetes In addition to suppressing EAE in vivo, PD-1 loss in Tregs is useful in protecting against other autoimmune disorders. For example, to further dissect the role of PD-1 in Tregs in tolerance and autoimmunity, PD-1 function in Tregs in a mouse model of spontaneous autoimmunity, the non-obese diabetic (NOD) mouse model of type 1 diabetes, was evaluated. The PD-1/PD-L1 pathway limits the initiation and progression of diabetes in NOD mice (Keir et al. (2006) *J. Exp. Med.* 203:883-895; Wang et al. (2005) *Proc. Natl. Acad. Sci. USA* 102:11823-11828; Ansari et al. (2003) *J. Exp. Med.* 198:63-69). Pdcd1$^{fl/fl}$ mice were crossed onto the NOD background and these were bred with NOD.FoxP3Cre mice (Zhou et al. (2008) *J. Exp. Med.* 205:1983-1991) to generate NOD.FoxP3CrePdcd1$^{fl/fl}$ mice. NOD females lacking PD-1 specifically in Tregs were protected from diabetes in two different animal facilities—0% vs. ~36% incidence in controls in an animal facility at Harvard (FIG. 10A) and 0% vs. ~60% incidence in controls in an animal facility at the University of Pittsburgh (FIG. 10B) by 30 weeks of age. In the Harvard mouse facility, control littermates began to develop diabetes at 14 weeks of age, whereas none of the 13 NOD.FoxP3CrePdcd1$^{fl/fl}$ mice developed hyperglycemia by 30 weeks of age. These findings indicate that PD-1 in Tregs has a critical role in limiting NOD diabetes regardless of environmental influences.

Figure 10:
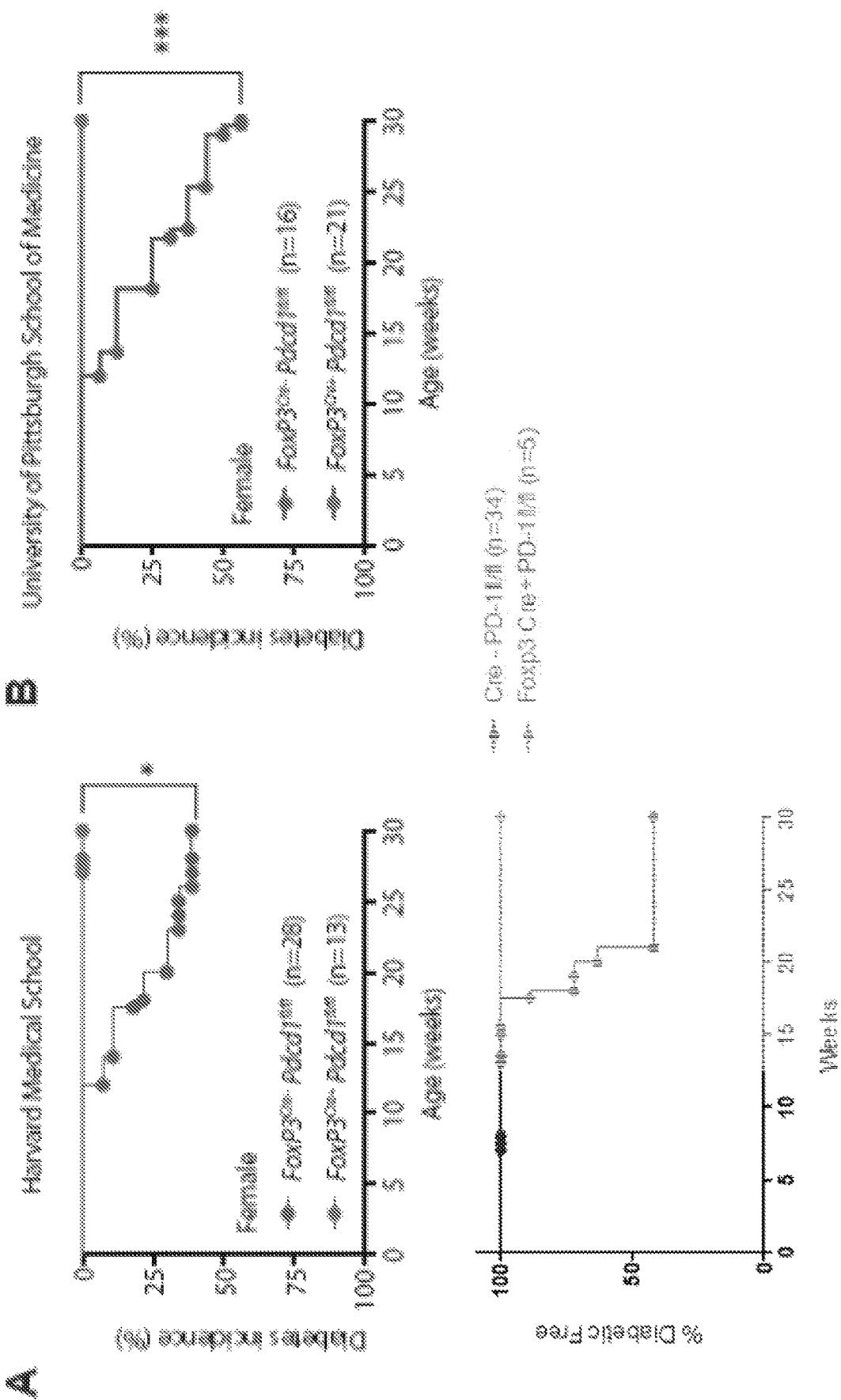
FIG. 10 includes 5 panels, identified as panels A, B, C, D, and E, which show that NOD mice lacking PD-1 selectively in Treg cells are protected from type 1 diabetes. Panel A shows the results of diabetes onset and incidence monitored in female NOD.FoxP3Cre+ Pdcd1$^{fl/fl}$ and NOD.FoxP3Cre− Pdcd1$^{fl/fl}$ littermates in an animal facility at Harvard Medical School for up to 30 weeks of age. Panel B shows the results of diabetes onset and incidence monitored in co-housed NOD.FoxP3Cre+ Pdcd1$^{fl/fl}$ and NOD.FoxP3Cre− Pdcd1$^{fl/fl}$ females in an animal facility at the University of Pittsburgh School of Medicine for up to 30 weeks of age. Panel C shows a representative H&E staining of an islet from NOD.FoxP3Cre+Pdcd1$^{fl/fl}$ and NOD.FoxP3Cre− Pdcd1$^{fl/fl}$ littermates at 14 weeks of age. Panel D shows insulitis scores from NOD.FoxP3Cre+ Pdcd1$^{fl/fl}$ and NOD.FoxP3Cre− Pdcd1$^{fl/fl}$ littermate controls at 14 weeks of age. Panel E shows a representative immunohistochemical staining of CD4 (left), FoxP3 (middle), and CD8 (right) expression in an islet from NOD.FoxP3Cre−Pdcd1$^{fl/fl}$ (top) or NOD.FoxP3Cre+Pdcd1$^{fl/fl}$ (bottom) littermates at 14 weeks of age taken at 400× magnification. The log-rank (Mantel-Cox) test was used for the data shown in Panels A and B. * p<0.05,  p<0.01, * p<0.001.
Figure 10:
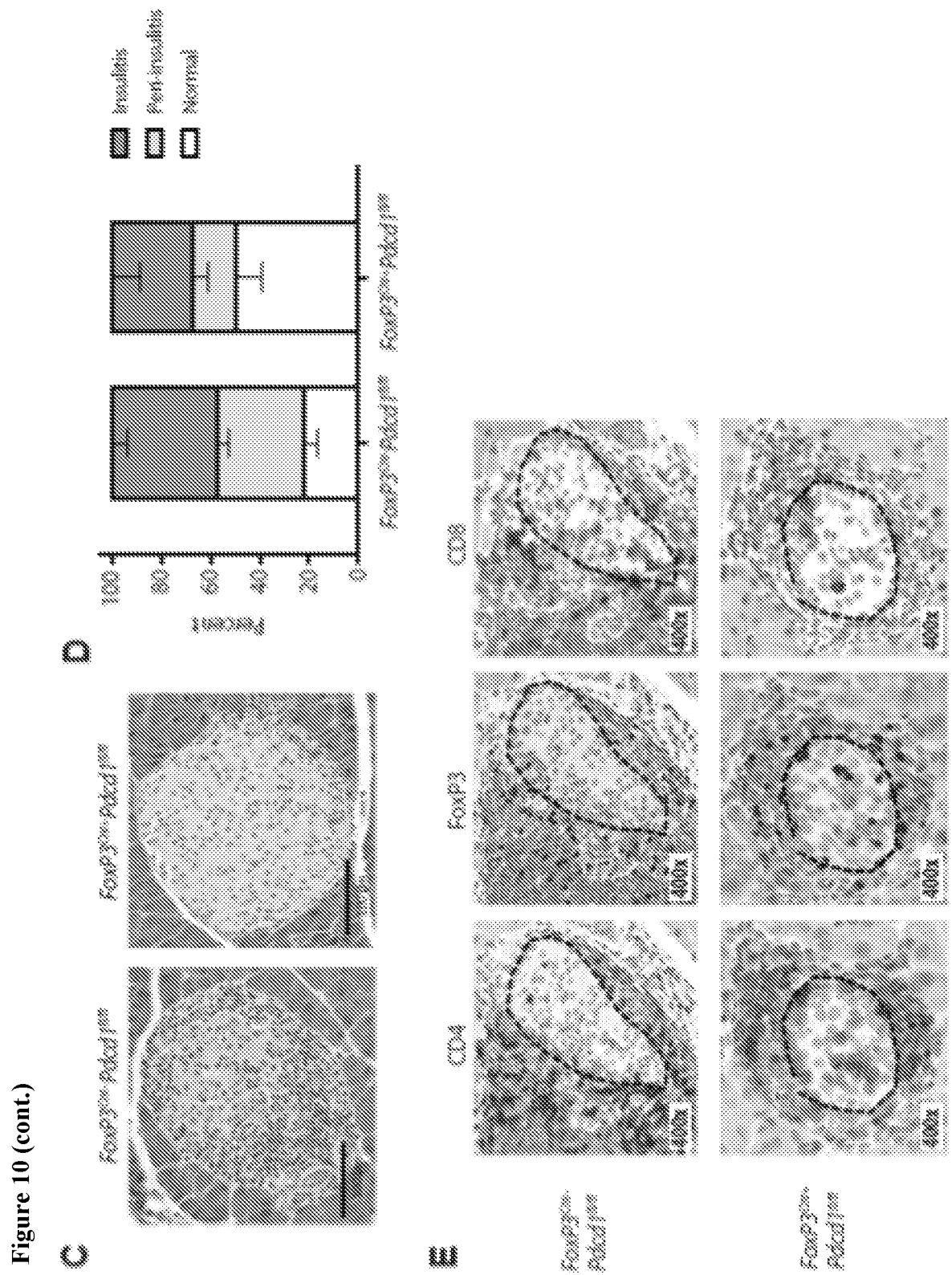

Certain hallmarks of diabetes pathology in NOD mice are well known, including development of peri-insulitis in pre-diabetic animals and progression to insulitis, where islets are infiltrated and eventually destroyed by leukocytes. Histopathologic comparison of NOD.FoxP3CrePdcd1$^{fl/fl}$ and control pancreata at 14 weeks of age, a time point prior to diabetes onset in the controls, revealed that NOD.FoxP3CrePdcd1$^{fl/fl}$ mice had significantly reduced peri-insulitis compared to NOD.FoxP3CrePdcd1$^{fl/fl}$ littermate controls (FIGS. 10C-10D). Immunohistochemical staining revealed an apparent increase in FoxP3$^+$ Tregs and decrease in CD8$^+$ T cells within adjacent sections of islets of NOD.FoxP3Cre Pdcd1$^{fl/fl}$ mice as compared to NOD.FoxP3CrePdcd1$^{fl/fl}$ littermate controls (FIG. 10E). The reduced number of islets with peri-insulitis and inflammatory cell infiltrates in NOD.FoxP3CrePdcd1$^{fl/fl}$ mice reflects a lack of clinical disease and suggests that the increased in Tregs within the islets may contribute to protection from clinical disease.

Figure 11:
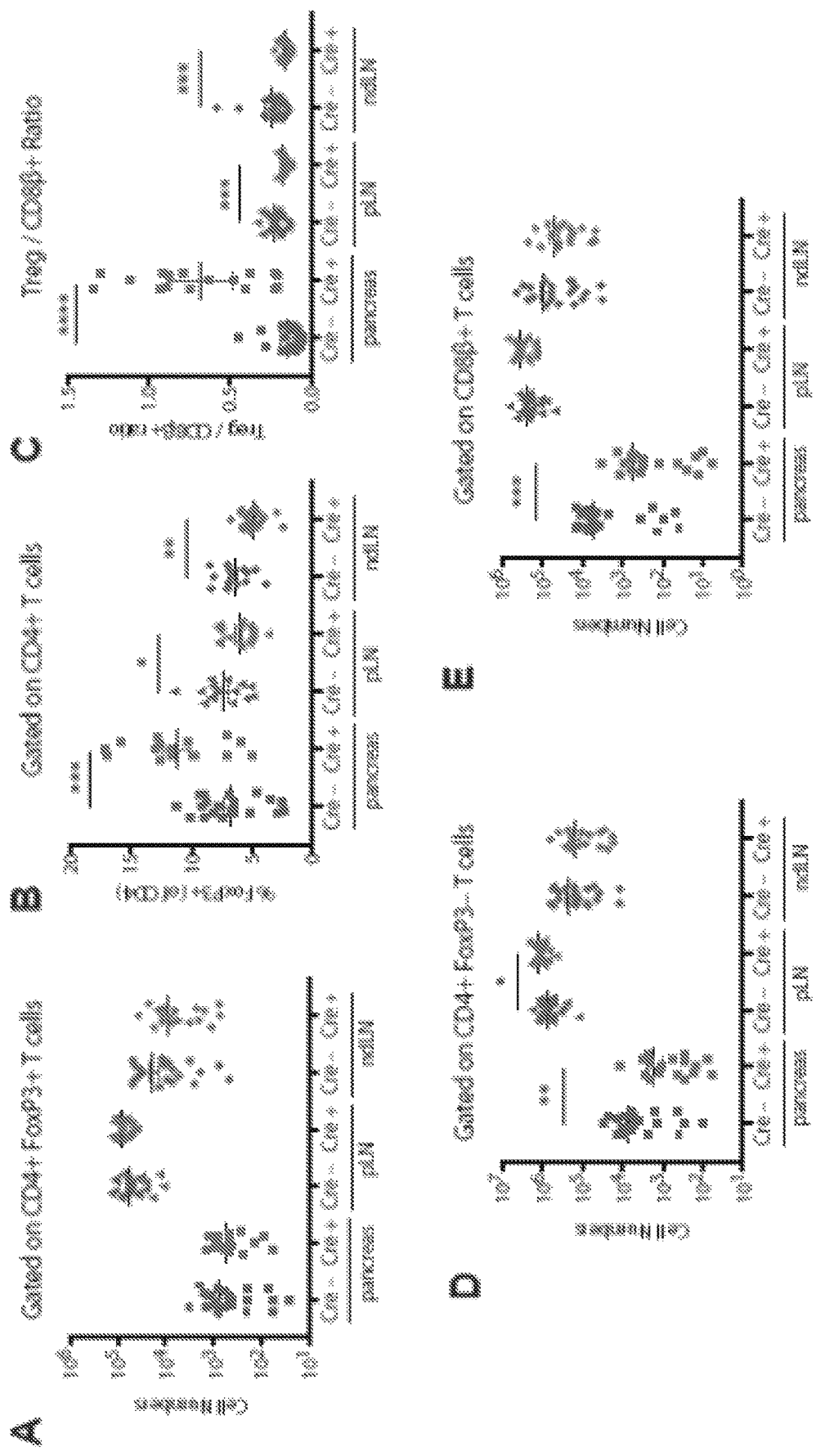
FIG. 11 includes 9 panels, identified as panels A, B, C, D, E, F, G, H, and I, which show that NOD.FoxP3 Cre+ Pdcd1$^{fl/fl}$ mice showed reduced effector T cells numbers and activation in the pancreas at 14 weeks of age. Panel A shows the numbers of CD4$^+$ FoxP3$^+$ Treg. Panel B shows the percentages of CD4$^+$ FoxP3$^+$ Tregs of total CD4$^+$ T cells. Panel C shows the ratio of CD4$^+$ FoxP3$^+$ Treg cells relative to CD8β$^+$ T cells in the pancreas, pancreatic lymph nodes (pLN), and inguinal lymph nodes (non-draining lymph node, ndLN) from FoxP3 Cre+ Pdcd1$^{fl/fl}$ (Cre+) and FoxP3 Cre− Pdcd1$^{fl/fl}$ (Cre−) littermate controls at 14 weeks of age. Panel D shows the numbers of CD4$^+$ FoxP3$^-$ T effector cells and Panel E shows CD8β$^+$ T cells from the pancreas, pLN and ndLN from Cre+ and Cre− littermate controls at 14 weeks of age. Panel F shows the percentages of Ki67 expressing-CD4$^+$ FoxP3$^-$ and Panel G shows CD8β$^+$ T cells from the pancreas, pLN, and ndLN. Panel H shows the percentages of Ki67-expressing CD4$^+$ FoxP3$^+$ Treg cells from the pancreas, pLN, and ndLN. Panel I shows a comparison of IL-10 production and surface LAP expression by CD4$^+$ FoxP3$^+$ T cells from pLN and ndLN of Cre+ and Cre− littermates. Data are pooled from 4 independent experiments for the data show in Panels A-E. Data are pooled from 2 independent experiments for the data shown in Panels F-H. Data are representative of 3 independent experiments for the data shown in Panel I. The Mann-Whitney nonparametric test was used for the data shown in Panels A-H. Student's t test was used for the data shown in Panel I. Data are represented as means±SEM. * p<0.05,  p<0.01, * p<0.001.
Figure 11:
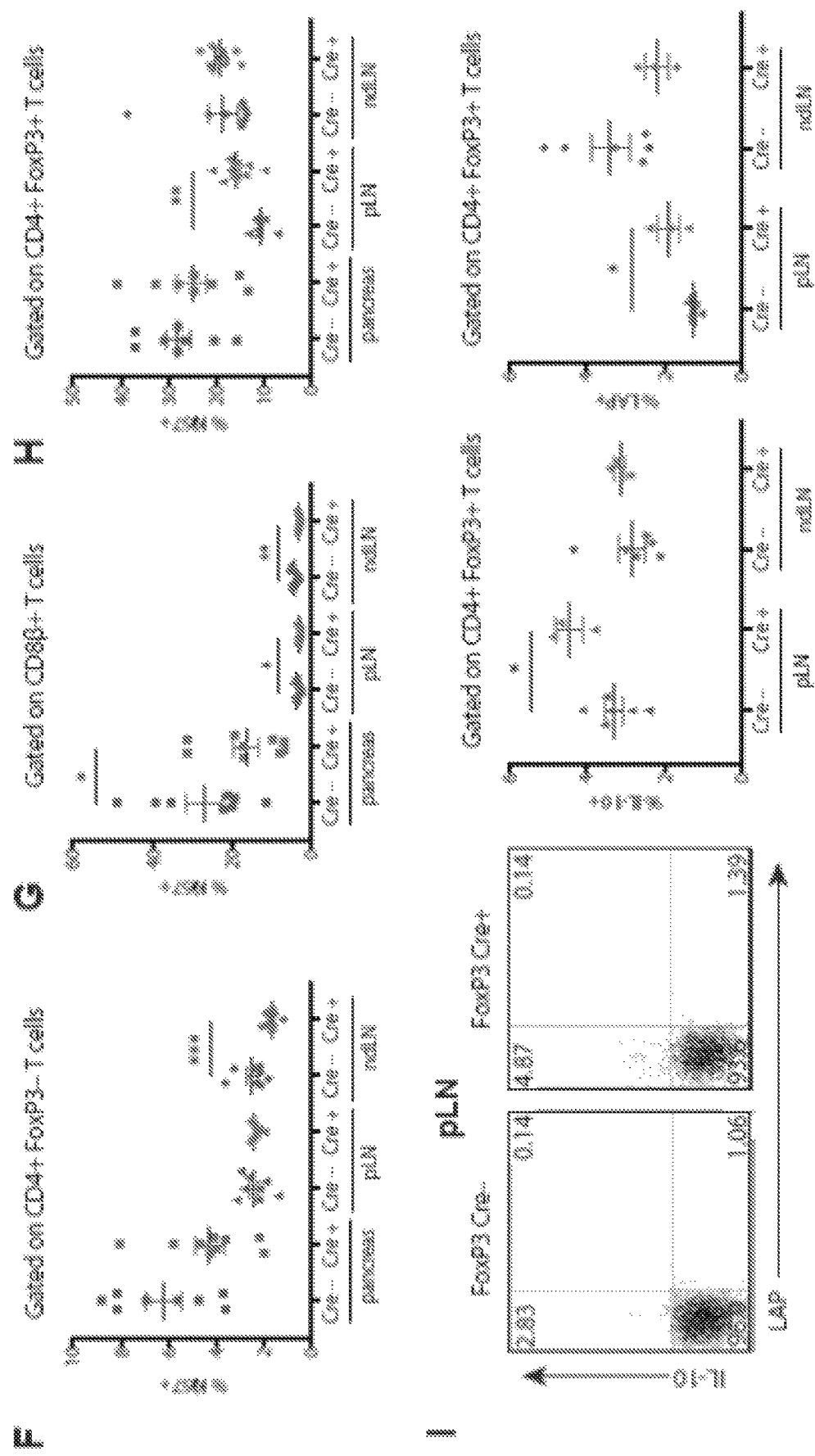

To determine the cellular mechanism by which NOD.FoxP3Cre Pdcd1$^{fl/fl}$ mice were protected from diabetes, Tregs, CD4$^+$ FoxP3$^-$ T cells and CD8$^+$ effector T cells in the pancreas, pancreatic lymph nodes (pLN), and non-draining inguinal lymph nodes (ndLN) of 14-week-old non-diabetic NOD.FoxP3Cre Pdcd1$^{fl/fl}$ mice and littermate controls were analyzed. Although there were comparable numbers of Tregs in the pancreas, pLN and ndLN of NOD.FoxP3CrePdcd1$^{fl/fl}$ mice and littermate controls (FIG. 11A), the frequency of Tregs relative to CD4$^+$ FoxP3$^-$ and CD8$^+$ effector T cells was significantly altered—higher in the pancreas, but lower in the pLN and ndLN (FIGS. 11B-11C) in the NOD.FoxP3Cre Pdcd1$^{fl/fl}$ mice as compared to controls. Moreover, there were significantly reduced numbers of CD4$^+$ FoxP3$^-$ effector T cells (FIG.

Figure 12:
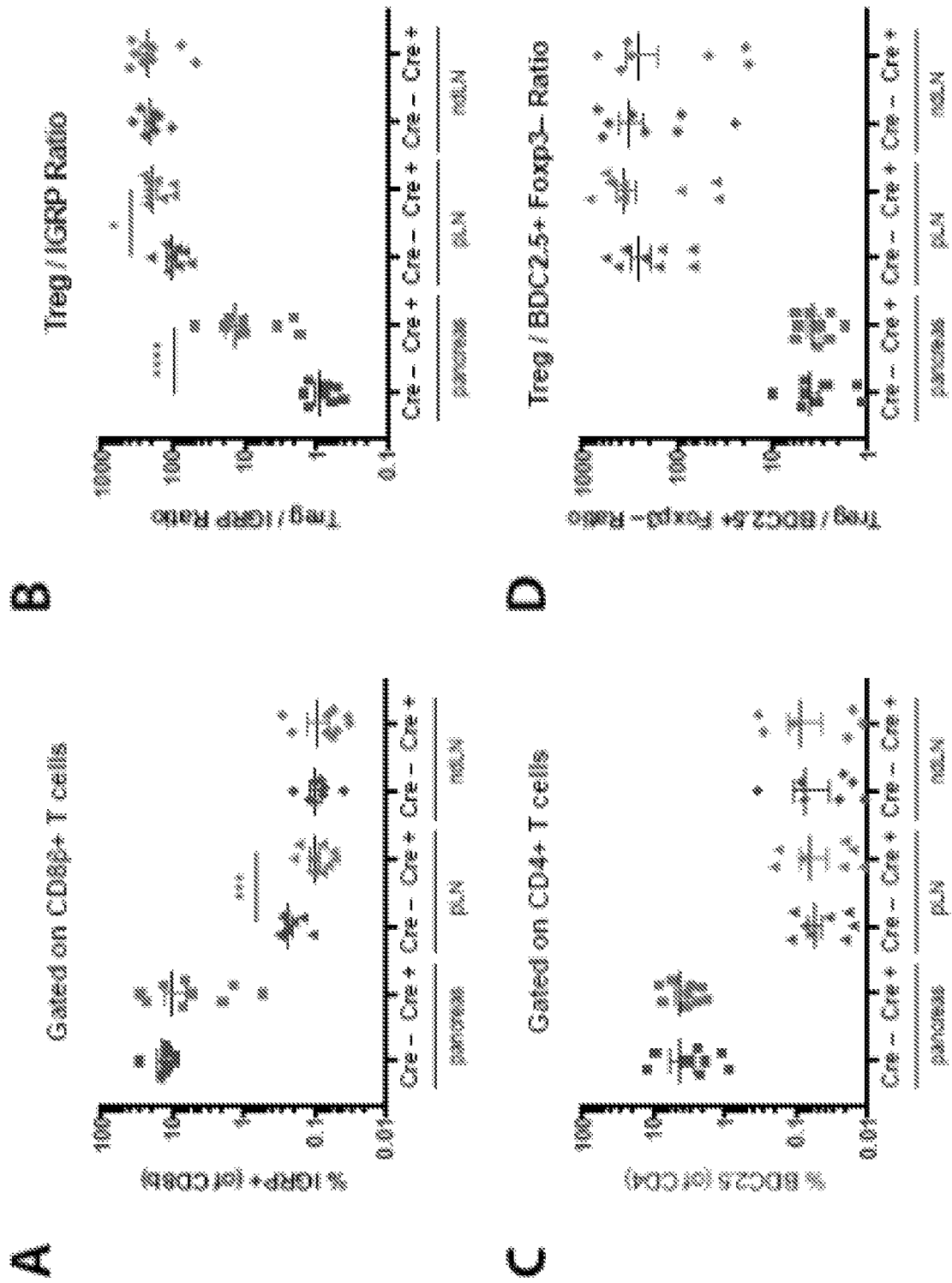
FIG. 12 includes 8 panels, identified as panels A, B, C, D, E, F, G, and H, which provides an immune characterization of NOD.FoxP3Cre Pdcd1$^{fl/fl}$ mice. Panel A shows the percentages of IGRP-specific CD8β$^+$ of total CD8β$^+$ T cells and Panel B shows the ratio of CD4$^+$ FoxP3$^+$ Tregs relative to IGRP-specific CD8β$^+$ from pancreas, pLN, and ndLN from pre-diabetic NOD.FoxP3Cre− Pdcd1$^{fl/fl}$ (Cre−) and NOD.FoxP3Cre+ Pdcd1$^{fl/fl}$ (Cre+) mice at 14 weeks of age. Panel C shows the percentages of BDC2.5$^+$ FoxP3$^-$ CD4$^+$ and Panel D shows ratio relative to FoxP3$^+$ Treg cells from pancreas, pLN, and ndLN of mice as described in Panel B. Panel E shows a comparison of Bcl-2 expression levels in Tregs from pancreas, pLN, and ndLN of mice described in Panel B. Panel F shows the percentages of CTLA-4$^+$ Tregs in pancreas, pLN, and ndLN of mice described in Panel B. Panel G shows FoxP3 expression levels in Tregs from pancreas, pLN, and ndLN of mice described in Panel B. Panel H shows the percentages of LAG3$^+$ Tregs in pancreas, pLN, and ndLN of mice described in Panel B. Data are representative of 2 independent experiments for data shown in Panels E and G. Data were pooled from 2 independent experiments for data shown in Panels A-D, F, and H. Student's t-test was used for the data shown in Panels E and G. The Mann-Whitney non-parametric test was used for the data shown in Panels A-D, F, and H. Data are represented as means±SEM. * p<0.05,  p<0.01, * p<0.001.
Figure 12:
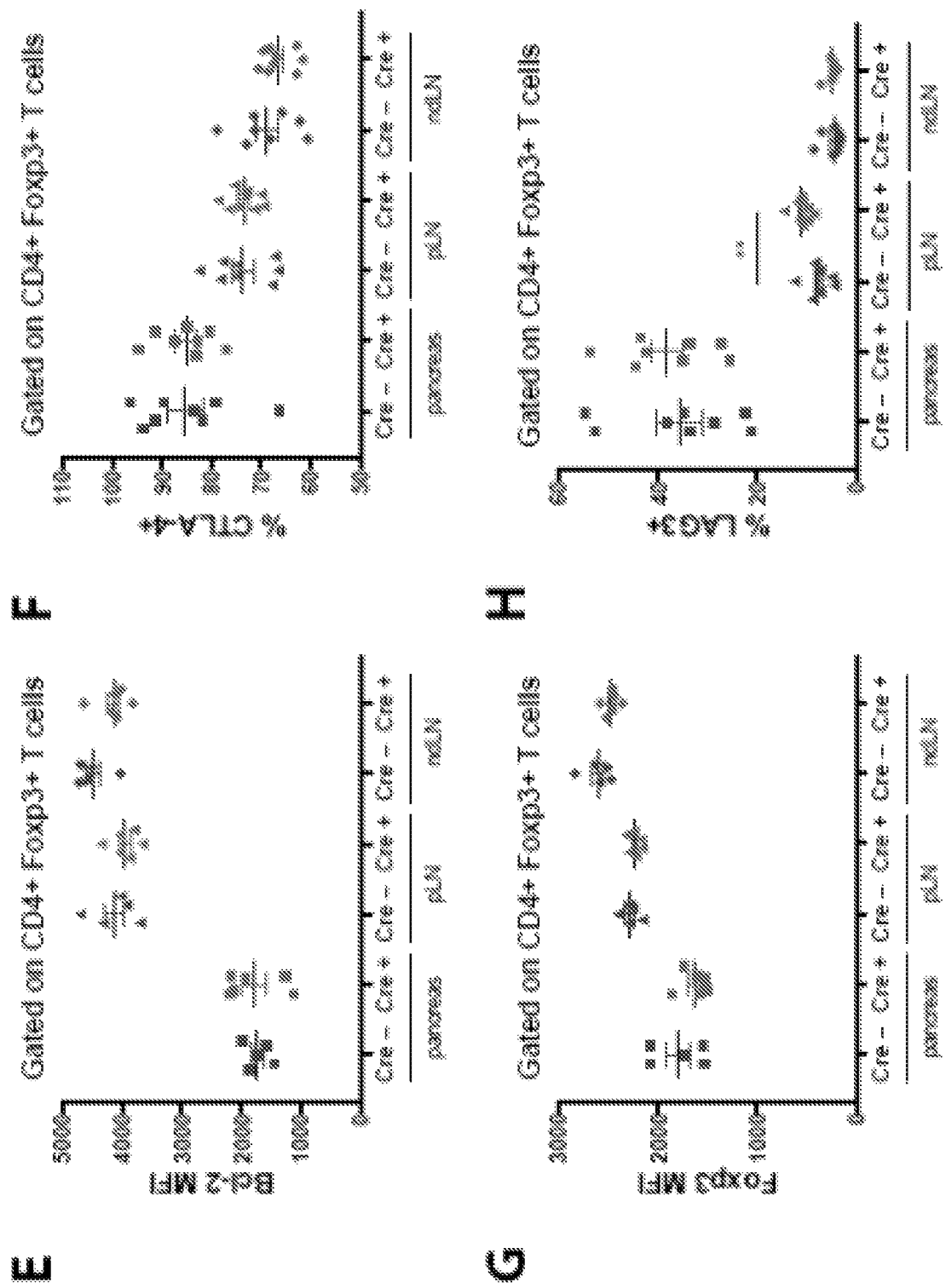

11D) and CD8$^+$ effector T cells (FIG. 11E) in the pancreas of NOD.FoxP3CrePdcd1$^{fl/fl}$ mice compared to littermate controls. Likewise, the frequency of islet specific glucose-6-phosphatase (IGRP)-specific CD8$^+$ T cells was reduced in the pLN and ratio of Tregs relative to IGRP-specific CD8$^+$ T cells was increased in the pancreas and pLN of NOD.FoxP3Cre Pdcd1$^{fl/fl}$ mice compared to littermate controls (FIGS. 12A-12B). The frequency of chromogranin A-specific (BDC2.5) CD4$^+$ T cells and the ratio of BDC2.5$^+$ CD4$^+$ Foxp3$^-$ T cells relative to Tregs were similar between NOD.FoxP3CrePdcd1$^{fl/fl}$ mice and littermate controls in the pancreas, pLN and ndLN (FIGS. 12C-12D). The increased ratio of Tregs relative to CD4$^+$ FoxP3$^-$ and CD8$^+$ effector T cells and reduced numbers of CD4$^+$ FoxP3$^-$ and CD8$^+$ effector T cells in the pancreas suggest that PD-1 deficient Tregs suppress the expansion and activation of diabetogenic effector T cells more potently than WT Tregs. Indeed, Ki67 expression was decreased in CD4$^+$ FoxP3$^-$ effector T cells (FIG. 11F) and CD8$^+$ T cells (FIG. 11G) in pancreata of NOD.FoxP3CrePdcd1$^{fl/fl}$ mice compared to littermate controls.

To understand the increased potency of PD-1-deficient Tregs in NOD mice, Tregs in the pancreas, pLN and ndLN from NOD.FoxP3Cre Pdcd1$^{fl/fl}$ mice and littermate controls were further analyzed. Although Tregs in the pancreas, pLN and ndLN from NOD.FoxP3CrePdcd1$^{fl/fl}$ mice and littermate controls expressed similar levels of Bcl-2 (FIG. 12E), CTLA-4 (FIG. 12F) and FoxP3 (FIG. 12G), there were higher frequencies of Ki67$^+$ (FIG. 12H) and LAG-3$^+$ (FIG. 12H) Tregs (FIG. 12I) in the pLN of NOD.FoxP3CrePdcd1$^{fl/fl}$ mice. These PD-1-deficient Tregs produced increased levels of IL-10 and surface LAP (FIG. 12I). These results indicate that increased Treg cell frequency, activation, and related suppressive function, result in protection of NOD.FoxP3CrePdcd1$^{fl/fl}$ mice from diabetes.

Figure 13:
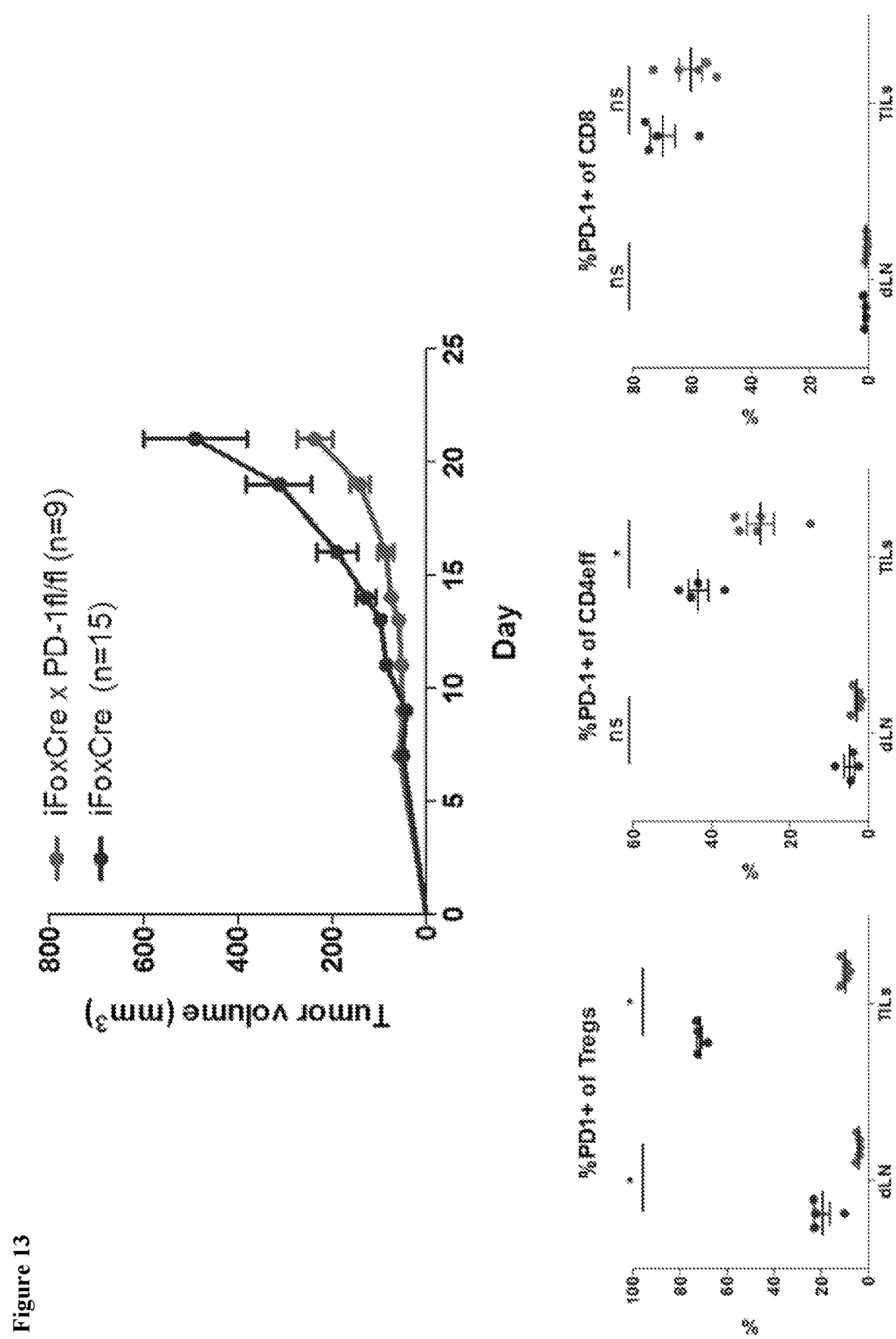
FIG. 13 shows that inducible deletion of PD-1 on Tregs before tumor challenge leads to enhanced anti-tumor immunity. The top panel shows the result of a tumor challenge with 100,000 MC38 colorectal adenocarcinoma cells subcutaneously (s.c.) 5 days after iFoxP3Cre and iFoxP3Cre PD-1$^{fl/fl}$ mice were treated with tamoxifen for 10 days. The bottom panels show the percentage of PD-1$^+$ cells from CD4$^+$ FoxP3$^+$ Tregs (left), CD4$^+$ FoxP3$^-$ Teffs (middle) and CD8$^+$ CTLs (right) from the tumor-draining lymph node (dLN) and tumor (TILs) isolated 24 days after tumor challenge. The results are representative of 2 independent experiments and p-values are as follows: *<0.05.

Moreover, inducible deletion of PD-1 on Tregs before tumor challenge leads to enhanced anti-tumor immunity (FIG. 13). Without being bound by theory, it is believed that overstimulation or overactivation of Tregs resulting from PD-1 deletion leads to Treg cell death or dysfunction such that Teff effector function is enhanced in mounting an immune response against a tumor challenge. In addition, the Tregs themselves may be converting to CD4+ Teffs and/or the deletion of PD-1 in Tregs modulates the Tregs versus Teffs cellular dynamics (e.g., impairs Tregs survival, promotes Treg plasticity and/or fragility, etc.) in order to increase immune responses against a tumor challenge. For example, PD-1 deletion on Tregs in the tumor may limit their interaction time with other cell subsets in the tumor and thereby decrease their net suppressive ability. PD-1 deletion on Tregs may also lead to production of pro-inflammatory cytokines by the Tregs themselves.

The PD-1 pathway has multifaceted roles in T cell tolerance, restraining the initial activation of naïve self-reactive T cells and/or responses of potentially pathogenic self-reactive effector T cells (Francisco et al. (2009) *Immunol. Rev.* 236:219-242). PD-L1 on non-hematopoietic cells can mediate tissue tolerance, protecting target organs from attack by self-reactive T cells and immune-mediated damage (Keir et al. (2006) *J. Exp. Med.* 203:883-895). The results described herein using mice lacking PD-1 only on Tregs indicate a new mechanism by which the PD-1 pathway regulates T cell tolerance. A recent study suggested a role for PD-1 mediated signals in Treg cell-mediated suppression (Zhang et al. (2016) *Proc. Natl. Acad. Sci. USA* 113:8490-8495). However, whether PD-1 signaling has a cell intrinsic role in Treg cell function has not previously been addressed. In our studies, using mice that selectively lack PD-1 in Tregs, we determined how PD-1 regulates Treg cell function in a cell intrinsic manner and discovered changes in PD-1-deficient Tregs that can explain their enhanced suppressive capacity.

The in vitro suppression assay results described herein demonstrated that PD-1-deficient Tregs could limit effector T cell proliferation better than WT Tregs at different ratios of effector T cells to Tregs, revealing that PD-1-deficient Tregs are more suppressive than WT Tregs on a per cell basis. The in vivo significance of the potent suppressive capacity of PD-1-deficient Tregs is demonstrated by ameliorated EAE in iFoxP3Cre Pdcd1$^{fl/fl}$ mice and protection of NOD.FoxP3CrePdcd1$^{fl/fl}$ mice from diabetes. Similar to the in vitro suppression assays, PD-1-deficient Tregs suppressed effector cells proliferation and activation and limit cytokine production better than WT Tregs in EAE and NOD diabetes. Indeed, though an increase in the number of PD-1-deficient Tregs in the target organ was not observed in either of these disease states, an increase in the ratio of PD-1-deficient Tregs relative to effector T cells was observed. Thus, PD-1-deficient Tregs suppress the activation, expansion and function of effector T cells more effectively than WT Tregs. Remarkably, selective deletion of PD-1 in Tregs in the PD-1 conditional knockout mice suppressed immune responses so potently that the mice became susceptible to *Pneumocystis*, an opportunistic infection. This finding indicates that the dysregulation of PD-1/PD-L1 signaling axis in Tregs can to lead to general immunosuppression. PD-1 immunotherapy inhibits PD-1 signals in all cell types but the integrated outcome is enhanced T cell functions. Development of agents, such as bi-specific antibodies that target PD-1 on effector T cells but not Tregs, might be even more effective.

Several reasons were identified for the enhanced potency of PD-1-deficient Tregs. PD-1-deficient Tregs expressed increased levels of CTLA-4 and TIGIT, and less LAG-3 (Durham et al. (2014) *PLoS One* 9:e109080), which may explain their enhanced suppressive capacity. CTLA-4 is a key mediator of Treg suppressive function (Wing et al. (2008) *Science* 322:271-275; Read et al. (2000) *J. Exp. Med.* 192:295-302), and TIGIT expression defines a Treg cell subset with activated phenotype, and contributes to selective Treg cell-mediated suppression of proinflammatory Th1 and Th17 cells by inducing secretion of the soluble effector molecule fibrinogen-like protein 2 (Fgl2) (Joller et al. (2014) *Immunity* 40:569-581). PD-1-deficient Tregs also expressed higher levels of IRF4, a transcription factor important for optimal suppressive ability of Tregs (Zheng et al. (2009) *Nature* 458:351-356; Levine et al. (2014) *Nat. Immunol.* 15:1070-1078). In addition, PD-1-deficient Tregs produced increased IL-10 and TGF-β, immunosuppressive cytokines made by Tregs to modulate the immune system (Rubtsov et al. (2008) *Immunity* 28:546-558; Uhlig et al. (2006) *J. Immunol.* 177:5852-5860; Green et al. (2003) *Proc. Natl. Acad. Sci. USA* 100:10878-10883; Nakamura et al. (2001) *J. Exp. Med.* 194:629-644). Thus, many alterations in PD-1-deficient Tregs can contribute to their increased potency.

The ameliorated EAE and diabetes in mice lacking PD-1 only in Tregs contrasts with the exacerbated EAE in Pdcd1-/- mice (Kroner et al. (2009) *Am. J. Pathol.* 174: 2290-2299; Wang et al. (2009) *Immunol.* 126:329-335) and the rapid diabetes in NOD.FoxP3Cre Pdcd1$^{fl/fl}$ mice (Keir et al. (2006) *J. Exp. Med.* 203:883-895; Wang et al. (2005) *Proc. Natl. Acad. Sci.* USA 102:11823-11828; Ansari et al. (2003) *J Exp. Med.* 198:63-69). The distinct outcomes of selective PD-1 deficiency in Tregs and global PD-1 deficiency point to distinct immunoregulatory functions for PD-1 on different cell types and underscore the importance of understanding the consequences of PD-1 inhibitory signals in different cell types and determining how these are integrated to regulate T cell activation and tolerance.

PD-1-mediated signals are essential for the proper control of regulatory T cell function. PD-1 inhibitory signals restrain Treg cell proliferation and suppressive capacity. Selective elimination of PD-1 in Tregs in PD-1 conditional knockout mice leads to enhanced immunosuppression, and results in increased susceptibility to infection and resistance to autoimmunity, demonstrating the key role for PD-1 on Tregs in controlling immune homeostasis, protective immunity and tolerance. The fact that CTLA-4 immunotherapy, which works in part by depleting Treg, synergizes so well with PD-1 blockade may be due to the role that PD-1 plays in inhibiting both Tregs and Tconv (Wolchok et al. (2013) *N. Engl. J Med.* 369:122-133; Selby et al. (2013) *Cancer Immunol. Res.* 1:32-42; Simpson et al. (2013)1 Exp. Med. 210:1695-1710). Anti-CTLA-4 may eliminate Tregs with enhanced function due to PD-1 blockade and thereby increase anti-tumor effector T cell responses due to CTLA-4 and PD-1 blockade. Given the clinical success of PD-1 pathway blockade in cancer immunotherapy (Topalian et al. (2014) *J Clin. Oncol.* 32:1020-1030; Pardoll (2012) *Nat. Immunol.* 13:1129-1132), a better understanding of how modulation of this pathway alters the delicate balance between tolerance and immunity is needed, considering the potential for autoimmune-mediated adverse events and susceptibility of cancer patients to acute infections. The results described herein demonstrate that PD-1 is an equal opportunity inhibitor of T cell activities. When PD-1 is lost on cells whose activity is to suppress immune responses, the consequence is a stronger suppressor cell.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for increasing suppression of effector T cells (Teffs) by regulatory T cells (Tregs), comprising a) inhibiting or blocking the expression of PD-1 in Tregs; and b) contacting the Tregs with Teffs, thereby increasing suppression of the Teffs by the Tregs.

2. The method of claim 1, wherein the Tregs are isolated from a subject, and the PD-1 expression is inhibited or blocked in the Tregs in vitro or ex vivo.

3. The method of claim 1, wherein the Tregs contact the Teffs in vitro or ex vivo, or in vivo.

4. The method of claim 3, wherein the Tregs and/or Teffs are administered to a subject.

5. The method of claim 1, wherein the Tregs are contacted with at least one agent that inhibits or blocks the expression of PD-1, wherein the at least one agent is a nucleic acid molecule that blocks PD-1 transcription or translation.

6. The method of claim 3, wherein the Tregs are administered to a subject having a disorder in need of increased suppression of Teffs by the Tregs, and the disorder is selected from the group consisting of autoimmune disorder, allergic disorder, hypersensitivity disorder, graft-versus-host disease (GVHD), solid organ transplantation rejection, vasculitis, systemic lupus erythematosus (SLE), type 1 diabetes (T1D), multiple sclerosis (MS), psoriasis, rheumatoid arthritis (RA), inflammatory bowel disease (IBD), and allergic asthma, ankylosing spondylitis (AS), and giant cell arteritis (GCA).

7. The method of claim 3, wherein the Tregs are administered to a subject receiving a therapy in need of increased suppression of Teffs by the Tregs, wherein the therapy is selected from the group consisting of adoptive cell therapy, solid organ transplantation, stem cell therapy, and gene therapy.

* * * * *

UNITED STATES PATENT AND TRADEMARK OFFICE
CERTIFICATE OF CORRECTION

PATENT NO. : 11,207,393 B2
APPLICATION NO. : 15/768077
DATED : December 28, 2021
INVENTOR(S) : Arlene H. Sharpe et al.

It is certified that error appears in the above-identified patent and that said Letters Patent is hereby corrected as shown below:

In the Specification

At Column 1, Lines 15-19, under the heading STATEMENT OF RIGHTS, please replace:
"This invention was made with government support under grant numbers P01 AI56299, R01 40614, R37 AI38310, R01 DK 089125, P01 AI108545, CA047904, and 1F31 DK105624-01A1 awarded by the National Institutes of Health. The government has certain rights in the invention."

With:
-- This invention was made with government support under AI040614 and AI056299 and AI038310 and HL007627 awarded by National Institutes of Health (NIH). The government has certain rights in this invention. --

Signed and Sealed this
Twenty-fifth Day of October, 2022

Katherine Kelly Vidal
*Director of the United States Patent and Trademark Office*